United States Patent
Chou et al.

(10) Patent No.: US 10,647,976 B2
(45) Date of Patent: May 12, 2020

(54) EXPRESSION OF POLYPEPTIDES INVOLVED IN LYSINE DECARBOXYLATION, AND METHODS AND APPLICATIONS THEREOF

(71) Applicants: CATHAY R&D CENTER CO., LTD., New District, Shanghai (CN); CATHAY INDUSTRIAL BIOTECH LTD., George Town, Grand Cayman (KY)

(72) Inventors: Howard Chou, Shanghai (CN); Naiqiang Li, Shanghai (CN); Xiucai Liu, Shanghai (CN)

(73) Assignees: Cathay Biotech Inc., Shanghai (CN); CIBT America Inc, Newark, DE (US)

( * ) Notice: Subject to any disclaimer, the term of this patent is extended or adjusted under 35 U.S.C. 154(b) by 34 days.

(21) Appl. No.: 15/321,800

(22) PCT Filed: Jun. 26, 2014

(86) PCT No.: PCT/CN2014/080873
§ 371 (c)(1),
(2) Date: Dec. 23, 2016

(87) PCT Pub. No.: WO2015/196430
PCT Pub. Date: Dec. 30, 2015

(65) Prior Publication Data
US 2017/0145403 A1    May 25, 2017

(51) Int. Cl.
| | | |
|---|---|---|
| C12N 9/88 | (2006.01) |
| C12N 15/00 | (2006.01) |
| C12N 1/20 | (2006.01) |
| C07H 21/04 | (2006.01) |
| C12P 13/00 | (2006.01) |
| C12N 15/52 | (2006.01) |

(52) U.S. Cl.
CPC .............. *C12N 9/88* (2013.01); *C12N 15/52* (2013.01); *C12P 13/001* (2013.01); *C12Y 401/01018* (2013.01)

(58) Field of Classification Search
None
See application file for complete search history.

(56) References Cited

U.S. PATENT DOCUMENTS

| | | | | |
|---|---|---|---|---|
| 8,541,208 B1 * | 9/2013 | Plesch | ................ | C07K 14/245 435/106 |
| 9,234,203 B2 * | 1/2016 | Pang | ..................... | C12N 15/74 |
| 2011/0039313 A1 | 2/2011 | Verseck et al. | | |
| 2012/0295317 A1 | 11/2012 | Schroder et al. | | |
| 2013/0309733 A1 * | 11/2013 | Pang | ..................... | C12N 15/74 435/128 |

FOREIGN PATENT DOCUMENTS

| | | |
|---|---|---|
| CN | 101240258 A | 8/2008 |
| CN | 102753682 A | 10/2012 |
| CN | 103789292 A | 5/2014 |
| EP | 1482055 A1 | 12/2004 |
| JP | 2004-208646 A | 7/2004 |

OTHER PUBLICATIONS

Stover. Complete genome sequence of Pseudomonas aeruginosa PAO1, an opportunistic pathogen. Nature. Aug. 31, 2000;406(6799):959-64.*
Studer. Residue mutations and their impact on protein structure and function: detecting beneficial and pathogenic changes. Residue mutations and their impact on protein structure and function: detecting beneficial and pathogenic changes. Biochem. J. (2013) 449, 581-594.*
Stover. Q9I2S7—UniProtKB. 2001.*
Stover. , AE004091—EMBL. 2006.*
Triscari-Barberi (Genome Sequence of the Polychlorinated-Biphenyl Degrader Pseudomonas pseudoalcaligenes KF707. J. Bacteriol. 194:4426-4427(2012).*
Triscari-Barberi. L8MQ24. UniProtKB database. Apr. 3, 2013.*
International Search Report dated Mar. 30, 2015 issued in PCT/CN2014/080873. (5 pages).
Puzio, P. et al. "unnamed protein product [Pseudomonas aeruginosa PAO1]", retrieved from NCBI Database accession No. CAV25800.1, Dec. 17, 2008, (2 pages).
Puzio, P. et al. "Sequence 91669 from Patent EP 2199304", retrieved from NCBI Database accession No. HD016404, Jul. 13, 2010 (2 pages).
Chinese Office Action with English Translation issued in Application No. 201480080136.6 dated Jan. 24, 2019, 12 pgs.
European Communication pursuant to Article 94(3) EPC issued in Application No. 14,895 982.8, dated Jun. 13, 2019, 5 pages.

* cited by examiner

*Primary Examiner* — Yong D Pak
(74) *Attorney, Agent, or Firm* — Rothwell, Figg, Ernst & Manbeck, P.C.

(57) ABSTRACT

The expression plasmid vectors comprise a polynucleotide sequence encoding Ldc2 polypeptide, a fragment, and/or a mutant. A backbone plasmid is capable of autonomous replication in a host cell. The host cell is not a *P. aeruginosa* cell. Transformants are transformed with expression plasmid vector. The transformants are not *P. aeruginosa*. Mutant host cells comprise a polynucleotide sequence encoding Ldc2 polypeptide, a fragment and/or a mutant that has been integrated into the host cell chromosome. A polypeptide, a fragment and/or a mutant comprise Ldc2. A non-naturally occurring polynucleotide, and/or a mutant encodes polypeptide comprising Ldc2. Biobased cadaverine is produced using the transformants and the biobased cadaverine is prepared by the method. Polyamides are formed using the biobased cadaverine and compositions.

24 Claims, 8 Drawing Sheets
Specification includes a Sequence Listing.

FIG. 3

| Gene | Purpose | Primer Sequence |
|---|---|---|
| *ldc1* | Amplify ldc1 from genome | ldc1-1: 5'-ggcgagctcacacaggaaacagaccatgccctacgaagccgatg-3' (SEQ ID NO: 25)<br>ldc1-2: 5'-ggctctagatcagtcccagttttccggc-3' (SEQ ID NO: 26) |
| *ldc2* | Amplify ldc2 from genome | ldc2-1: 5'-ggcgagctcacacaggaaacagaccatgtataaagacctcaaatttcccg-3' (SEQ ID NO: 27)<br>ldc2-2: 5'-ggctctagatcattcctttatgcattcaacgg-3' (SEQ ID NO: 28) |
| | Construct pUC18 with $P_{synthetic}+P_{lac}$ | psyn-1: 5'-ggcgaattcagtttattcttgacatgtagtgagggggctggtataatgagctcggtacccgggat-3' (SEQ ID NO: 29)<br>psyn-2: 5'-ggcagtactcaaccaagtcattctgagaatagtg-3' (SEQ ID NO: 30) |

FIG. 4
A.
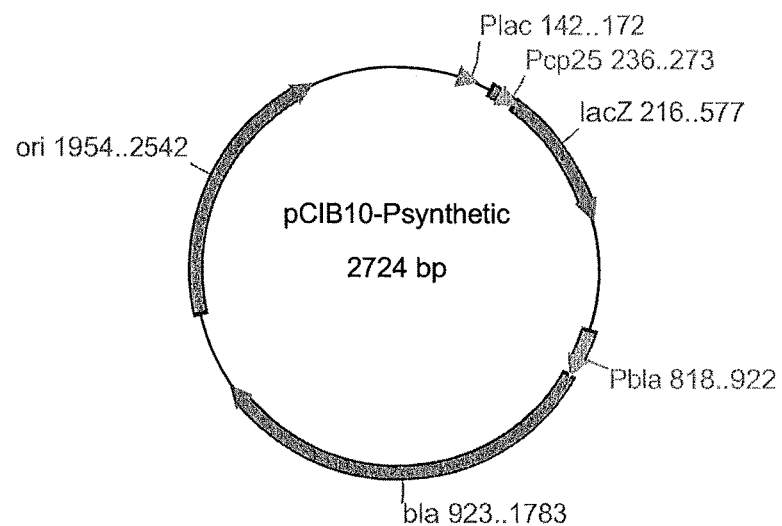
B.
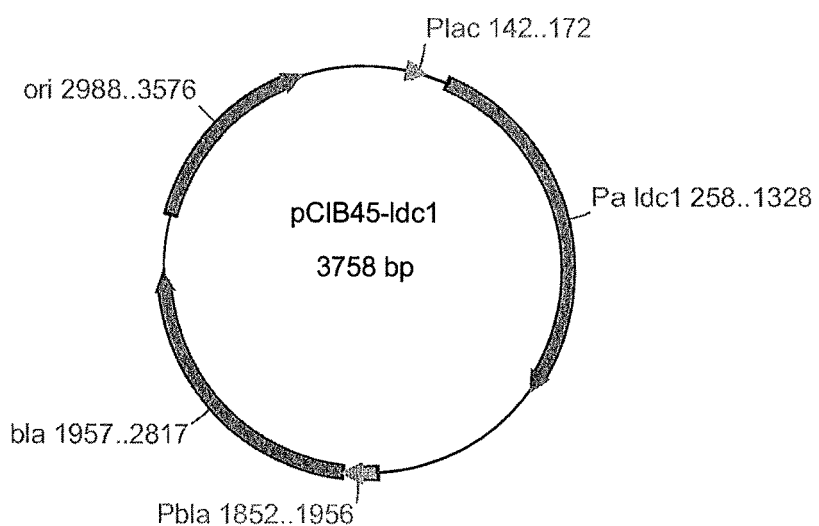

FIG. 4
C.
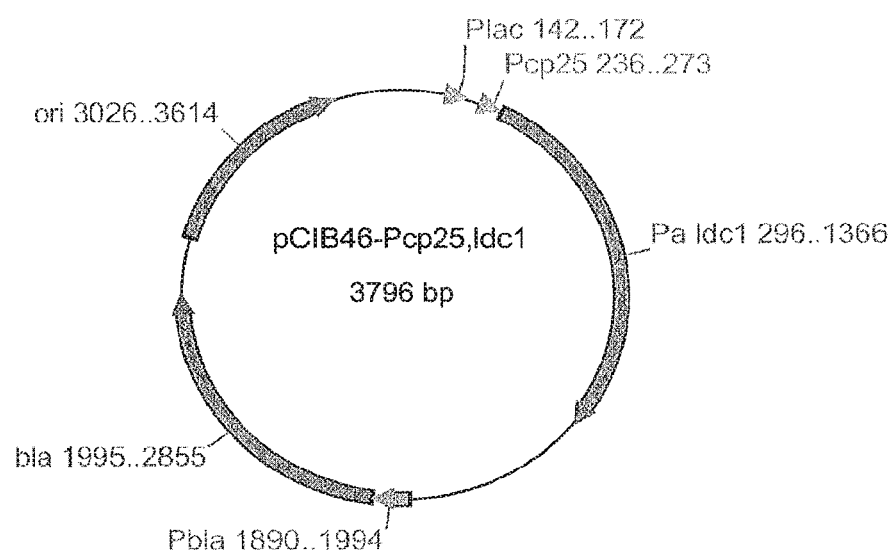
D.
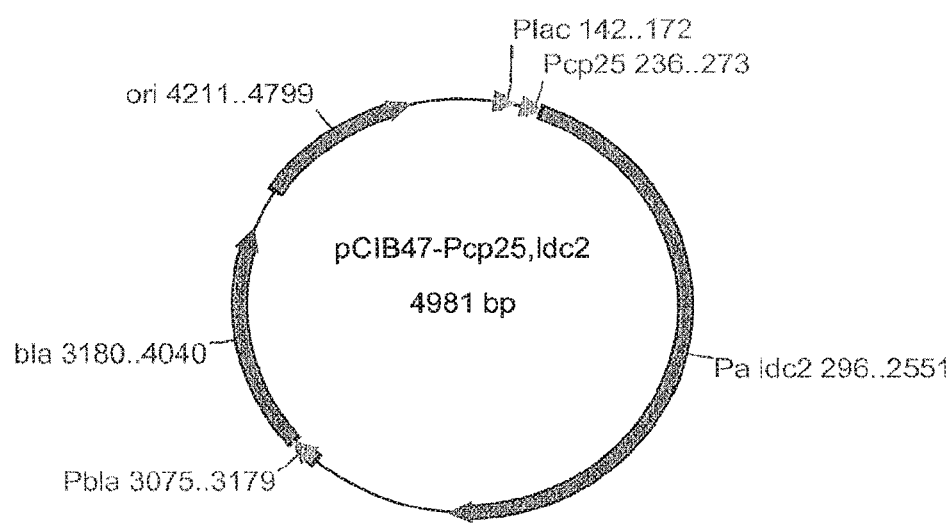

```
E_coli_AAB08613        -INTNSTMDVSVQGNRNALNYFEYALGQAEDIAIRMRQYDEYLDKYTFP 131   (SEQ ID NO: 31)
S_sonnei_WP_001021016  -INTNSTMDVSVQDNSKINFFEYALGQSEDIAIRMRQYNEYLDNYTPP 131   (SEQ ID NO: 32)
S_enterica_WP_001647872 -INTNSTLDVSVKGNRKALNFFEYALGLAEDIATRIKQYNEYLDRYTPP 131   (SEQ ID NO: 33)
E_coli_AAA23536        -ANTYSTLGVSAKTLALQISFFEYALGAAEDIANKIRQYTRYINFILPP 131   (SEQ ID NO: 34)
P_aeruginosa_ldc2      QVYIENAPASLHAOLRQLRGILYLFEDTVPFLARQVARAANYLACLLPP 136   (SEQ ID NO: 35)
```

FIG. 6

```
E_coli_AAB08615          APDGSTLLIQN...SLAHLIQNEDVVPVWLKPTRNALGILGGIPRREPT  281   (SEQ ID NO: 36)
S_sonnei_WP_001921016    APSGSTLLIDN...SLAHLISNDVVPVWLEPTRNALGILGGIPRREPT  281   (SEQ ID NO: 37)
S_enterica_WP_001647872  APAGSTLLIQN...SLAHLIQNEDVVPLWLKPTRNALGILGGIPRREPT 281   (SEQ ID NO: 38)
E_coli_AAA23538          APAGSPTLIDN...SLCHLNSNSDVTPIYFRPTRNAYGILGGIPQSKPQ  281   (SEQ ID NO: 39)
P_aeruginosa_lacZ        VGHEDLVLVQR...STLHSIIMTRKIPLKLTPERNELGIGPIPLSSFS  300   (SEQ ID NO: 40)
```

EXPRESSION OF POLYPEPTIDES INVOLVED IN LYSINE DECARBOXYLATION, AND METHODS AND APPLICATIONS THEREOF

CROSS-REFERENCE TO RELATED APPLICATIONS

The present application is a national stage filing under 35 U.S.C. § 371 of PCT/CN2014/080873, filed on 26 Jun. 2014. Each application is incorporated herein by reference in its entirety.

BACKGROUND

Cadaverine is a platform chemical involved in the production of various products. Cadaverine can be synthesized via decarboxylation of lysine in microorganisms. Lysine decarboxylases are the enzymes that catalyze production of cadaverine by removing the carboxyl group from lysine. For example, in *Escherichia coli* (*E. coli*), cadaverine is biosynthesized directly from L-lysine by two lysine decarboxylase polypeptides, CadA and LdcC.

Currently, biosynthesis of cadaverine is performed using two strategies: fermentative production or in vitro enzyme catalysis. In a fermentative production of L-lysine approach, a lysine decarboxylase, usually CadA or LdcC, is added to a lysine producing bacteria strain (e.g., *Corynebacterium glutamicum* and *E. coli*) to extend the lysine biosynthesis pathway to a cadaverine biosynthesis pathway. Alternatively, for in vitro enzyme catalysis, bacteria can be engineered or induced to produce lysine decarboxylases, usually CadA or LdcC, which can then be used in conversion of lysine to cadaverine by decarboxylation.

However, production of cadaverine is currently limited and results in low yields. Therefore, there is a need for a process to produce cadaverine with higher yields.

SUMMARY OF THE INVENTION

One aspect of the invention relates to a polypeptide comprising, consisting of, or consisting essentially of one or more mutants of *Pseudomonas aeruginosa* (*P. aeruginosa*) polypeptide Ldc2. As used herein, the *P. aeruginosa* polypeptide Ldc2 is referred to as "*P. aeruginosa* Ldc2," "Ldc2" or "Ldc2 polypeptide," and has the amino acid sequence of SEQ ID NO: 4.

Another aspect of the invention relates to a first polynucleotide encoding one or more first polypeptides comprising, consisting of, or consisting essentially of one or more second polypeptides selected from the group consisting of Ldc2, fragments of Ldc2, and mutants of Ldc2, wherein the first polynucleotide comprises one or more second polynucleotides encoding the one or more second polypeptides, respectively; when there are a plurality of the first polypeptides, each first polypeptides may be the same or different; when there are a plurality of the second polypeptides, each second polypeptide may be the same or different; when there are a plurality of the second polynucleotides, each second polynucleotide may be the same or different; the one or more first polypeptides may be expressed individually or as a fusion protein; and when a second polypeptide is Ldc2, at least one of the corresponding second polynucleotides encoding the second polypeptide comprises, consists of, or consists essentially of a mutant *P. aeruginosa* ldc2 gene. As used herein, the *P. aeruginosa* ldc2 gene is referred to as "*P. aeruginosa* ldc2" or "ldc2," and has the polynucleotide sequence of SEQ ID NO: 3. Examples of mutants of ldc2 encode Ldc2, and may be codon optimized ldc2 (e.g., ldc2-co1 (SEQ ID NO: 17)).

Another aspect of the invention relates to a third polynucleotide encoding one or more third polypeptides comprising, consisting of, or consisting essentially of one or more fourth polypeptides selected from the group consisting of Ldc2 (SEQ ID NO: 4), fragments of Ldc2, and mutants of Ldc2; wherein the third polynucleotide comprises one or more fourth polynucleotides encoding the one or more fourth polypeptides, respectively; when there are a plurality of the third polypeptides, each third polypeptides may be the same or different; when there are a plurality of the fourth polypeptides, each fourth polypeptide may be the same or different; when there are a plurality of the fourth polynucleotides, each fourth polynucleotide may be the same or different; and the one or more third polypeptides may be expressed individually or as a fusion protein. In certain embodiments, the polynucleotide comprises, consists of, or consists essentially of ldc2.

Another aspect of the invention relates to a first expression plasmid vector comprising, consisting of, or consisting essentially of a fifth polynucleotide encoding one or more fifth polypeptides comprising, consisting of, or consisting essentially of one or more sixth polypeptides selected from the group consisting of Ldc2, fragments of Ldc2, and mutants of Ldc2; and a backbone plasmid capable of autonomous replication in a host cell. In certain embodiments, the host cell is a *P. aeruginosa* cell.

Another aspect of the invention relates to a second expression plasmid vector comprising, consisting of, or consisting essentially of a seventh polynucleotide encoding one or more seventh polypeptides comprising, consisting of, or consisting essentially of one or more eighth polypeptides selected from the group consisting of Ldc2, fragments of Ldc2, and mutants of Ldc2; and a backbone plasmid capable of autonomous replication in a host cell. In certain embodiments, the host cell is not a *P. aeruginosa* cell.

Another aspect of the invention relates to a first transformant comprising the first expression plasmid vector in a host cell. In certain embodiments, the host cell is a *P. aeruginosa* cell.

Another aspect of the invention relates to a second transformant comprising the second expression plasmid vector in a host cell. In certain embodiments, the host cell is not a *P. aeruginosa* cell.

Another aspect of the invention relates to a first mutant host cell comprising a first or third polynucleotide as disclosed herein, wherein the first or third polynucleotide has been integrated into a chromosome of the host cell. In certain embodiments, the host cell is not a *P. aeruginosa* cell. In certain embodiments, the host cell is a *P. aeruginosa* cell.

Another aspect of the invention relates to a method for producing one or more ninth polypeptides selected from the group consisting of Ldc2, fragments of Ldc2, and mutants of Ldc2 comprising obtaining the first transformant, the second transformant or the first mutant host cell as described herein, culturing the first transformant, the second transformant, or the first mutant host cell under conditions effective for the expression of the one or more ninth polypeptides, and harvesting the one or more ninth polypeptides.

Another aspect of the invention relates to a method for producing cadaverine comprising cultivating the first transformant, the second transformant or the first mutant host cell as described herein, producing cadaverine using the culture obtained from cultivating the first transformant, the second transformant or the first mutant host cell to decarboxylate lysine, and extracting and purifying cadaverine.

Other aspects of the invention relate to polyamides and 1,5-diisocyanatopentane prepared from biobased cadaverine prepared as disclosed herein, and compositions and preparation methods thereof.

BRIEF DESCRIPTION OF THE DRAWINGS

FIG. 3: Polymerase chain reaction (PCR) primer sequences used to construct the recombinant expression plasmid vectors containing either a P. aeruginosa gene having the sequence of SEQ ID NO: 1 (hereinafter "ldc1") or ldc2 according to an embodiment of the invention, and primer sequences (psyn-1 and psyn-2) used to construct the promoter sequence of SEQ ID NO: 5.

FIG. 5: A sequence alignment of a portion of the sequences from lysine decarboxylase polypeptides from different species including E. coli LdcC, Shigella sonnei CadA, Salmonella enterica lysine decarboxylase, E. coli CadA, and P. aeruginosa Ldc2, with a conserved serine (the boxed region).

FIG. 6: A sequence alignment of a portion of the sequences from lysine decarboxylase polypeptides from different species including E. coli LdcC, Shigella sonnei CadA, Salmonella enterica lysine decarboxylase, E. coli CadA, and P. aeruginosa Ldc2, with a conserved asparagine and lysine (the boxed regions).

DETAILED DESCRIPTION OF THE INVENTION

Figure 1:
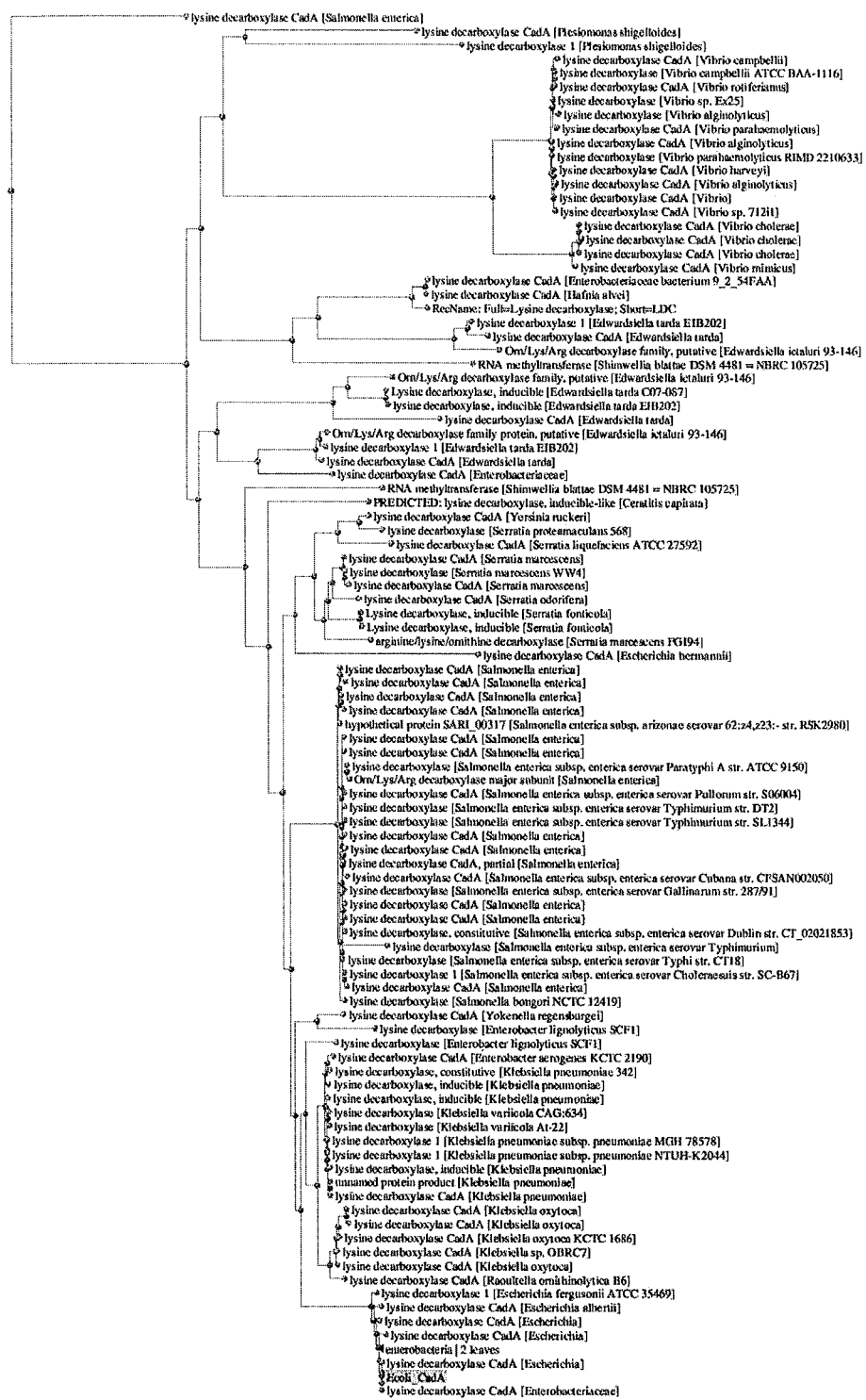
FIG. 1: A protein tree generated from a sequence similarity search for the E. coli protein CadA (highlighted) using the National Center for Biotechnology Information (NCBI) Basic Local Alignment Search Tool (BLAST).

The following description provides specific details for a thorough understanding of, and enabling description for, embodiments of the disclosure. However, one skilled in the art will understand that the disclosure may be practiced without these details. In other instances, well-known structures and functions have not been shown or described in detail to avoid unnecessarily obscuring the description of the embodiments of the disclosure.

P. aeruginosa Ldc2 (Accession: WP_014603046.1) was characterized as a beta-elimination lyase polypeptide in a BLAST search. P. aeruginosa Ldc2 has low sequence similarity with the known E. coli lysine decarboxylases, CadA and LdcC (39.44% and 38.71% sequence identity, respectively). The BLAST search results did not indicate that Ldc2 was a lysine decarboxylase.

Functional heterologous expression of Pseudomonas proteins in E. coli is challenging partially due to low gene expression and insoluble proteins (West, 1988). For example, heterologous expression of a previously characterized P. aeruginosa lysine decarboxylase, Ldc1 (SEQ ID NO: 2, Accession: EME94559.1), in an E. coli strain did not result in an increased cadaverine production, even though its BLAST result indicated that it was a putative member of the lysine decarboxylase family (the corresponding P. aeruginosa gene is ldc1 (SEQ ID NO: 1)).

As disclosed herein, it has unexpectedly been found that heterologous expression of P. aeruginosa Ldc2 has resulted in unexpectedly high yield cadaverine production, with E. coli expressing Ldc2 exhibiting higher cadaverine yields than E. coli expressing the E. coli lysine decarboxylase. CadA (see, e.g., Example 5). Expressions of P. aeruginosa Ldc2 in other host cells (e.g., Hafnia alvei (H. alvei)) have also resulted in an unexpectedly higher yield of cadaverine production compared to expression of E. coli CadA (see, e.g., Example 5). Furthermore, it has unexpectedly been found that expression of an Ldc2 mutant polypeptide disclosed herein has resulted in high cadaverine production.

One aspect of the invention relates to a polypeptide comprising, consisting of, or consisting essentially of one or more mutants of Ldc2. A mutant of Ldc2 may include deletion, substitution, addition, and/or insertion of one or more amino acids to the amino acid sequence of SEQ ID NO: 4, while the mutant of Ldc2 provides substantially the same function as Ldc2 (i.e., the mutant of Ldc2 has about 80% or higher lysine decarboxylase activity compared to that of Ldc2; about 90% or higher lysine decarboxylase activity compared to that of Ldc2; about 95% or higher lysine decarboxylase activity compared to that of Ldc2; about 97% or higher lysine decarboxylase activity compared to that of Ldc2; about 99% or higher lysine decarboxylase activity compared to that of Ldc2; or about 100% or higher lysine decarboxylase activity compared to that of Ldc2.)

Examples of mutants of Ldc2 include, without limitation, SEQ ID NO: 6 (Ldc2 S111C), SEQ ID NO: 11 (Ldc2 N262T), SEQ ID NO: 12 (Ldc2 K265N), SEQ ID NO: 13 (Ldc2 S111C/N262T), SEQ ID NO: 14 (Ldc2 S111C/K265N), SEQ ID NO: 15 (Ldc2 N262T/K265N), SEQ ID NO: 16 (Ldc2 S111C/N262T/K265N), homologous polypeptides of Ldc2, homologous polypeptides of Ldc2 S111C (e.g. Ldc2 S111X), homologous polypeptides of Ldc2 N262T (e.g. Ldc2 N262X'), homologous polypeptides of Ldc2 K265N (e.g. Ldc2 K265X'), homologous polypeptides of Ldc2 S111C/N262T (e.g. Ldc2 S111X/N262X'), homologous polypeptides of Ldc2 S111C/K265N (e.g. Ldc2 S111X/K265X"), homologous polypeptides of Ldc2 N262T/K265N (e.g. Ldc2 N262X'/K265X"), and homologous polypeptides of Ldc2 S111C/N262T/K265N (e.g. Ldc2 S111X/N262X'/K265X"). X is any amino acid that is not serine, X' is any amino acid that is not asparagine, and X" is any amino acid that is not lysine. As used herein, a homologous polypeptide is at least about 90%, at least about 95%, at least about 97%, at least about 98%, or at least about 99% homologous with the polypeptide. When a Ldc2 mutant has multiple mutations, each mutation may be the same or different.

As used herein, a polypeptide comprising a specific polypeptide sequence may include fragments, and/or mutants of the specific polypeptide sequence, while still providing substantially the same function as the whole original unmutated specific polypeptide sequence. A fragment of a polypeptide means a part of the polypeptide that provides substantially the same function as the whole polypeptide. Examples of mutants of a specific polypeptide sequence include deletions, substitutions, additions, and/or insertions of one or more amino acids to the specific polypeptide sequence. For example, a fragment or mutant of Ldc2 possesses substantially the same function of the Ldc2 polypeptide (e.g. lysine decarboxylase activity).

Another aspect of the invention relates to a first polynucleotide encoding one or more first polypeptides comprising, consisting of, or consisting essentially of one or more second polypeptides selected from the group consisting of Ldc2, fragments of Ldc2, and mutants of Ldc2; wherein the first polynucleotide comprises one or more second polynucleotides encoding the one or more second polypeptides, respectively; when there are a plurality of the first polypeptides, each first polypeptides may be the same or different; when there are a plurality of the second polypeptides, each second polypeptide may be the same or different; when there are a plurality of the second polynucleotides, each second polynucleotide may be the same or different; the one or more first polypeptides may be expressed individually or as a fusion protein; and when a second polypeptide is Ldc2, at least one of the corresponding second polynucleotides encoding the second polypeptide comprises, consists of, or consists essentially of a mutant ldc2. Examples of mutants of ldc2 encode Ldc2, and may be codon optimized ldc2 (e.g., ldc2-co1 (SEQ ID NO: 17)).

Mutants of Ldc2 are the same as described supra. For example, without limitation, mutants of Ldc2 comprise, consist, or consist essentially of Ldc2 with mutations at one or more amino acid positions selected from the group consisting of 111, 262, and 265 (as described supra, e.g. SEQ ID NO: 6 (Ldc2 S111C), SEQ ID NO: 11 (Ldc2 N262T), SEQ ID NO: 12 (Ldc2 K265N), SEQ ID NO: 13 (Ldc2 S111C/N262T), SEQ ID NO: 14 (Ldc2 S111C/K265N), SEQ ID NO: 15 (Ldc2 N262T/K265N), SEQ ID NO: 16 (Ldc2 S111C/N262T/K265N), Ldc2 S111X, Ldc2 N262X', Ldc2 K265X'', Ldc2 S111X/N262X', Ldc2 S111X/K265X'', Ldc2 N262X'/K265X'', and Ldc2 S111X/N262X'/K265X'').

In one embodiment, the second polypeptides are mutants of Ldc2, and the corresponding second polynucleotides encoding the second polypeptides are polynucleotides encoding Ldc2 (e.g. ldc2 (SEQ ID NO: 3)), a codon optimized ldc2 (e.g. ldc2-co1, SEQ ID NO: 17)) containing one or more suitable nucleotide mutations selected from the group consisting of a mutation at nucleotide position 331, a mutation at nucleotide position 332, a mutation at nucleotide position 333, a mutation at nucleotide position 784, a mutation at nucleotide position 785, a mutation at nucleotide position 786, a mutation at nucleotide position 793, a mutation at nucleotide position 794, and a mutation at nucleotide position 795.

In another embodiment, the second polypeptides are mutants of Ldc2, and the corresponding second polynucleotides encoding the second polypeptides are polynucleotides encoding Ldc2 (e.g. ldc2 (SEQ ID NO: 3), a codon optimized ldc2 (e.g. ldc2-co1, SEQ ID NO: 17)) containing one or more suitable nucleotide mutations selected from the group consisting of a mutation at nucleotide position 332, a mutation at nucleotide position 785, and a mutation at nucleotide position 795. In certain examples, without limitation, the nucleotide at position 332 may be mutated to G, the nucleotide at position 785 may be mutated to a C, and the nucleotide at position 795 may be mutated to a T or C.

In another embodiment, the second polypeptides are Ldc2, and the corresponding second polynucleotides are polynucleotides that are not ldc2 (SEQ ID NO: 3) and encode Ldc2. Examples of such second polynucleotides include, without limitation, codon optimized ldc2 (e.g. ldc2-co1, SEQ ID NO: 17).

In certain embodiments, examples of the second polynucleotides include, without limitation, SEQ ID NO: 17 (ldc2-co1), SEQ ID NO: 18 (ldc2-co1 C332G), SEQ ID NO: 19 (ldc2-co1 A785C), SEQ ID NO: 20 (ldc2-co1 A795C), SEQ ID NO: 21 (ldc2-co1 C332G/A785C), SEQ ID NO: 22 (ldc2-co1 C332G/A795C), SEQ ID NO: 23 (ldc2-co1 A785C/A795C), and SEQ ID NO: 24 (ldc2-co1 C332G/A785C/A795C).

In certain embodiments, the first and second polynucleotides may be recombinant or non-naturally occurring polynucleotides. In certain embodiments, the first and second polynucleotides may be cDNAs. In certain embodiments, the first and second polynucleotides are obtained by codon optimization for optimal polypeptide expression in a particular microorganism (e.g., *E. coli, H. alvei,* or *P. aeruginosa*).

Nucleotide sequences, polynucleotides, and DNA molecules as used herein are not limited to the functional region, and may include at least one of an expression suppression region, a coding region, a leader sequence, an exon, an intron, and an expression cassette (see, e.g. Papadakis et al., "Promoters and Control Elements: Designing Expression Cassettes for Gene Therapy," Current Gene Therapy (2004), 4, 89-113). Further, nucleotide sequences or polynucleotides may include double strand DNA or single strand DNA (i.e., a sense chain and an antisense chain constituting the double strand DNA), or RNA. A polynucleotide containing a specific polynucleotides sequence may include fragments, and/or mutants of the specific polynucleotides sequence. A fragment of a polynucleotide means a part of the polynucleotide that encodes a polypeptide which provides substantially the same function as the polypeptide encoded by the whole polynucleotide. Examples of mutants of a specific polynucleotides sequence include naturally occurring allelic mutants; artificial mutants; and polynucleotides sequences obtained by deletion, substitution, addition, and/or insertion of one or more nucleotides to the specific polynucleotides sequence. It should be understood that such fragments, and/or mutants of a specific polynucleotides sequence encode polypeptides having substantially the same function as the polypeptide encoded by the original, specific polynucleotides sequence. For example, a fragment and/or mutant of ldc2 encodes a polypeptide that possesses substantially the same function of Ldc2 (e.g. lysine decarboxylase activity).

Another aspect of the invention relates to a third polynucleotide encoding one or more third polypeptides comprising, consisting of, or consisting essentially of one or more fourth polypeptides selected from the group consisting of Ldc2, fragments of Ldc2, and mutants of Ldc2; wherein the third polynucleotide comprises one or more fourth polynucleotides encoding the one or more fourth polypeptides, respectively; when there are a plurality of the third polypeptides, each third polypeptides may be the same or different; when there are a plurality of the fourth polypeptides, each fourth polypeptide may be the same or different; when there are a plurality of the fourth polynucleotides, each fourth polynucleotide may be the same or different; and the one or more third polypeptides may be expressed individually or as a fusion protein. In certain embodiments, the third and the fourth polynucleotides are recombinant or non-naturally occurring polynucleotides. In certain embodiments, the third and the fourth polynucleotides are cDNAs. In certain embodiments, the third and the fourth polynucleotides may be obtained by codon optimization for optimal polypeptide expression in a particular microorganism (e.g., *E. coli, H. alvei,* or *P. aeruginosa*). An example of a codon optimized ldc2 encoding Ldc2 is SEQ ID NO: 17 (ldc2-co1). In certain embodiments, the third polynucleotide comprises, consists of, or consists essentially of *P. aeruginosa* ldc2 (SEQ ID NO: 3), a fragment thereof, and/or a mutant thereof. When the fourth polypeptides are mutants of Ldc2, they are the same as described supra; and the corresponding fourth polynucleotides are the same as described supra. Examples of the fourth polynucleotides further include, without limitation, polynucleotides encoding Ldc2 (e.g. ldc2, and mutants thereof, such as SEQ ID NO: 17 (ldc2-co1)).

Codon optimization is a technique that may be used to maximize the protein expression in an organism by increasing the translational efficiency of the gene of interest. Different organisms often show particular preferences for one of the several codons that encode the same amino acid due to mutational biases and natural selection. For example, in fast growing microorganisms such as *E. coli*, optimal codons reflect the composition of their respective genomic tRNA pool. Therefore, the codons of low frequency of an amino acid may be replaced with codons for the same amino acid but of high frequency in the fast growing microorganism. Accordingly, the expression of the optimized DNA sequence is improved in the fast growing microorganism. See, e.g. http://www.guptalab.org/shubhg/pdf/shubhra_codon.pdf for an overview of codon optimization technology, which is incorporated herein by reference in its entirety. As provided herein, polynucleotide sequences may be codon optimized for optimal polypeptide expression in a particular microorganism including, but not limited to, *E. coli, H. alvei*, and *P. aeruginosa*.

In certain embodiments, mutants of a polynucleotide can be obtained from codon optimization of the polynucleotide to decrease the guanine (G) and cytosine (C) polynucleotide content thereof for improved protein expression. A genome is considered GC-rich if about 50% or more of its bases are G or C. A high GC content in the polynucleotide sequence of interest may lead to the formation of secondary structure in the mRNA, which can result in interrupted translation and lower levels of expression. Thus, changing G and C residues in the coding sequence to A and T residues without changing the amino acids may provide higher expression levels.

*P. aeruginosa* ldc2 is considered GC-rich since more than 66% of its bases are G or C. In some embodiments, a polynucleotide may be optimized to comprise a guanine and cytosine polynucleotide content that comprises less than about 60%, less than about 55%, less than about 50%, less than about 45%, or less than about 40% of the total polynucleotide content of the polynucleotide. In some embodiments, the polynucleotide that is optimized to comprise a specific guanine and cytosine polynucleotide content may be *P. aeruginosa* ldc2.

As further shown herein, heterologous expression of an Ldc2 mutant Ldc2 S111C (SEQ ID NO: 6) has resulted in unexpectedly high cadaverine production, with *E. coli* expressing the Ldc2 S111C exhibiting higher cadaverine yields than *E. coli* expressing the *E. coli* lysine decarboxylase CadA or wild-type Ldc2 (e.g., see Table 3). Although the serine at amino acid position 111 in Ldc2 is conserved across lysine decarboxylases from various species (e.g., see FIG. 5), Ldc2 S111C contains a mutation at amino acid position 111 to cysteine. In certain embodiments, the serine at amino acid position 111 in Ldc2 may be mutated to any other amino acid (i.e. Ldc2 S111X). For example, without limitation, X may be alanine, arginine, asparagine, aspartic acid, cysteine, glutamine, glutamic acid, glycine, histidine, isoleucine, leucine, lysine, methionine, phenylalanine, proline, threonine, tryptophan, tyrosine, or valine; preferably, X is alanine, glycine, isoleucine, leucine, methionine, threonine, tyrosine, or valine; more preferably, X is methionine, threonine, or tyrosine.

In certain embodiments, the polynucleotide encoding Ldc2 S111C comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) having a mutation at nucleotide position 332. In certain embodiments, the nucleotide at position 332 may be mutated to G (e.g. ldc2-co1 C332G (SEQ ID NO: 18)).

In certain embodiments, the polynucleotide encoding Ldc2 S111C comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) with mutations at nucleotide positions 332 and 333. In certain embodiments, the nucleotide at position 332 may be mutated to a G and the nucleotide at position 333 may be mutated to a T or C.

In certain embodiments, a polynucleotide encoding Ldc2 S111X comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) having one or more suitable nucleotide mutations selected from the group consisting of a mutation at nucleotide position 331, a mutation at nucleotide position 332, and a mutation at nucleotide position 333.

In certain embodiments, a polynucleotide encoding Ldc2 S111C or Ldc2 S111X may undergo further codon optimization for optimal polypeptide expression in a particular microorganism (e.g., *E. coli, H. alvei*, or *P. aeruginosa*).

As further shown herein, heterologous expression of another Ldc2 mutant Ldc2 N262T (SEQ ID NO: 11) also resulted in unexpectedly high cadaverine production, with *E. coli* expressing the codon Ldc2 N262T exhibiting higher cadaverine yields than *E. coli* expressing the *E. coli* lysine decarboxylase wild-type Ldc2 (e.g., see Table 4). Although the asparagine at amino acid position 262 in Ldc2 is conserved across lysine decarboxylases from various species (e.g., see FIG. 6), Ldc2 N262T contains a mutation at amino acid position 262. In certain embodiments, the asparagine at amino acid position 262 in Ldc2 may be mutated to any other amino acid (i.e. Ldc2 N262X'). For example, without limitation, X' may be alanine, arginine, aspartic acid, cysteine, glutamine, glutamic acid, glycine, histidine, isoleucine, leucine, lysine, methionine, phenylalanine, proline, serine, threonine, tryptophan, tyrosine, or valine. In certain embodiments, X' is preferably an amino acid with a polar uncharged side chain such as, without limitation, serine, threonine, or glutamine.

In certain embodiments, the polynucleotide encoding Ldc2 N262T comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) with a mutation at nucleotide position 785. In certain embodiments, the nucleotide at position 785 may be mutated to a C (e.g. ldc2-co1 A785C (SEQ ID NO: 19)).

In certain embodiments, the polynucleotide encoding Ldc2 N262T comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) having mutations at nucleotide positions 785 and 786. In certain embodiments, the nucleotide at position 785 may be mutated to a C and the nucleotide at position 786 may be mutated to a T, C, A, or G.

In certain embodiments, a polynucleotide encoding Ldc2 N262X' comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) having one or more suitable nucleotide mutations selected from the group consisting of a mutation at nucleotide position 784, a mutation at nucleotide position 785, and a mutation at nucleotide position 786.

In certain embodiments, a polynucleotide encoding Ldc2 N262T or Ldc2 N262X' may undergo further codon optimization for optimal polypeptide expression in a particular microorganism (e.g., *E. coli, H. alvei,* or *P. aeruginosa*).

As further shown herein, heterologous expression of an Ldc2 mutant Ldc2 K265N (SEQ ID NO: 12) also resulted in unexpectedly high cadaverine production, with *E. coli* expressing the Ldc2 K265N exhibiting higher cadaverine yields than *E. coli* expressing the wild-type Ldc2 (e.g., see Table 5). Although the lysine at amino acid position 265 in Ldc2 is conserved across lysine decarboxylases from various species (e.g., see FIG. 6), Ldc2 K265N contains a mutation at position 265. In certain embodiments, the lysine at position 265 of Ldc2 may be mutated to any other amino acid (i.e. Ldc2 K265X"). For example, without limitation, X" may be alanine, arginine, asparagine, aspartic acid, cysteine, glutamine, glutamic acid, glycine, histidine, isoleucine, leucine, methionine, phenylalanine, proline, serine, threonine, tryptophan, tyrosine, or valine; preferably an amino acid with polar uncharged side chains such as serine, threonine, asparagine, or glutamine.

In certain embodiments, the polynucleotide encoding Ldc2 K265N comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) with a mutation at nucleotide position 795. In certain embodiments, the nucleotide at position 795 may be mutated to a T or C (e.g. ldc2-co1 A795C (SEQ ID NO: 20)).

In certain embodiments, a polynucleotide encoding Ldc2 K265X" comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) having one or more suitable nucleotide mutations selected from the group consisting of a mutation at nucleotide position 793, a mutation at nucleotide position 794, and a mutation at nucleotide position 795.

In certain embodiments, a polynucleotide encoding Ldc2 K265N or Ldc2 K265X" may undergo further codon optimization for optimal polypeptide expression in a particular microorganism (e.g., *E. coli, H. alvei,* or *P. aeruginosa*).

In certain embodiments, a mutant of Ldc2 (also may be referred to as a "Ldc2 mutant") may comprise a mutation at more than one amino acid in the sequence of SEQ ID NO: 4. In certain embodiments, the mutant of Ldc2 is a double mutant comprising SEQ ID NO: 13 (Ldc2 S111C/N262T), which has mutations at amino acid positions 111 and 262. In certain embodiments, the serine at amino acid position 111 and the asparagine at amino acid position 262 in Ldc2 may be mutated to any other amino acid (Ldc2 S111X/N262X'). X and X' can be the same or different, and are the same as described supra.

In certain embodiments, the polynucleotide encoding Ldc2 S111C/N262T comprises, consists of, or consists essentially of a polynucleotide encoding Ldc2 (e.g. ldc2 (SEQ ID NO: 3), a codon optimized ldc2 (e.g. SEQ ID NO: 17)) with mutations at nucleotide positions 332 and 785. In certain embodiments, the nucleotide at position 332 may be mutated to a G and the nucleotide at position 785 may be mutated to a C (e.g. ldc2-co1 C332G/A785C (SEQ ID NO: 21)).

In certain embodiments, the polynucleotide encoding Ldc2 S111C/N262T comprises, consists of, or consists essentially of a polynucleotide encoding Ldc2 (e.g. ldc2 (SEQ ID NO: 3), a codon optimized ldc2 (e.g. SEQ ID NO: 17)) containing one or more mutations as described supra for the polynucleotides encoding Ldc2 S111C and one or more mutations as described supra for the polynucleotides encoding Ldc2 N262T.

In certain embodiments, a polynucleotide encoding Ldc2 S111X/N262X' comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) containing one or more suitable nucleotide mutations selected from the group consisting of a mutation at nucleotide position 331, a mutation at nucleotide position 332, a mutation at nucleotide position 333, a mutation at nucleotide position 784, a mutation at nucleotide position 785, and a mutation at nucleotide position 786.

In certain embodiments, a polynucleotide encoding Ldc2 S111C/N262T or Ldc2 S111X/N262X' may undergo further codon optimization for optimal polypeptide expression in a particular microorganism (e.g., *E. coli, H. alvei,* or *P. aeruginosa*).

In certain embodiments, the mutant of Ldc2 is a double mutant comprising SEQ ID NO: 14 (Ldc2 S111C/K265N), which has mutations at amino acid positions 111 and 265. In certain embodiments, the serine at amino acid position 111 and the lysine at amino acid position 265 may be mutated to any other amino acid (Ldc2 S111X/N265X"). X and X" can be the same or different, and are the same as described supra.

In certain embodiments, the polynucleotide encoding Ldc2 S111C/K265N comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) with mutations at nucleotide positions 332 and 795.

In certain embodiments, the polynucleotide encoding Ldc2 S111C/K265N comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) containing one or more mutations as described supra for the polynucleotides encoding Ldc2 S111C and one or more mutations as described supra for the polynucleotides encoding Ldc2 K265N. In certain embodiments, the nucleotide at position 332 may be mutated to a G and the nucleotide at position 795 may be mutated to a T or C (e.g. ldc2-co1 C332G/A795C (SEQ ID NO: 22)).

In certain embodiments, a polynucleotide encoding Ldc2 S111X/K265X" comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) having one or more suitable nucleotide mutations selected from the group consisting of a mutation at nucleotide position 331, a mutation at nucleotide position 332, a mutation at nucleotide position 333, a mutation at nucleotide position 793, a mutation at nucleotide position 794, and a mutation at nucleotide position 795.

In certain embodiments, a polynucleotide encoding Ldc2 S111C/K265N or Ldc2 S111X/K265X" may undergo further codon optimization for optimal polypeptide expression in a particular microorganism (e.g., *E. coli, H. alvei,* or *P. aeruginosa*).

In certain embodiments, the mutant of Ldc2 is a double mutant comprising SEQ ID NO: 15 (Ldc2 N262T/K265N), which has mutations at amino acid positions 262 and 265. In certain embodiments, the asparagine at amino acid position 262 and the lysine at amino acid position 265 may be mutated to any other amino acid (Ldc2 N262X'/K265X"). X' and X" can be the same or different, and are the same as described supra.

In certain embodiments, the polynucleotide encoding Ldc2 N262T/K265N comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) with mutations at nucleotide positions 785 and 795. In certain embodiments, the nucleotide at position 785 may be mutated to a C, and the nucleotide at position 795 may be mutated to a T or C (e.g. ldc2-co1 A785C/ A795C (SEQ ID NO: 23)).

In certain embodiments, the polynucleotide encoding Ldc2 N262T/K265N comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) containing one or more mutations as described supra for the polynucleotides encoding Ldc2 N262T and one or more mutations as described supra for the polynucleotides encoding Ldc2 K265N.

In certain embodiments, a polynucleotide encoding Ldc2 N262X'/K265X" comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) containing one or more nucleotide mutations selected from the group consisting of a mutation at nucleotide position 784, a mutation at nucleotide position 785, a mutation at nucleotide position 786, a mutation at nucleotide position 793, a mutation at nucleotide position 794, and a mutation at nucleotide position 795.

In certain embodiments, a polynucleotide encoding Ldc2 N262T/K265N or Ldc2 N262X'/K265X" may undergo further codon optimization for optimal polypeptide expression in a particular microorganism (e.g., *E. coli, H. alvei*, or *P. aeruginosa*).

In certain embodiments, the mutant of Ldc2 is a triple mutant comprising SEQ ID NO: 16 (Ldc2 S111C/N262T/ K265N), which has mutations at amino acid positions 111, 262, and 265. In certain embodiments, the serine at amino acid position 111, the asparagine at amino acid position 262, and the lysine at amino acid position 265, may be mutated to any other amino acid (S111X/N262K/K265X"). X, X' and X" can be the same or different, and are the same as described supra.

In certain embodiments, the polynucleotide encoding Ldc2 S111C/N262T/K265N comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) with mutations at nucleotide positions 332, 785, and 795. In certain embodiments, the nucleotide at position 332 may be mutated to G, the nucleotide at position 785 may be mutated to a C, and the nucleotide at position 795 may be mutated to a T or C.

In certain embodiments, the polynucleotide encoding Ldc2 S111C/N262T/K265N comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) containing one or more mutations as described supra for the polynucleotides encoding Ldc2 S111C, one or more mutations as described supra for the polynucleotides encoding Ldc2 N262T, and one or more mutations as described supra for the polynucleotides encoding Ldc2 K265N (e.g. ldc2-co1 C332G/A785C/A795C (SEQ ID NO: 24)).

In certain embodiments, a polynucleotide encoding Ldc2 S111X/N262K/K265X" comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) containing one or more suitable nucleotide mutations selected from the group consisting of a mutation at nucleotide position 331, a mutation at nucleotide position 332, a mutation at nucleotide position 333, a mutation at nucleotide position 784, a mutation at nucleotide position 785, a mutation at nucleotide position 786, a mutation at nucleotide position 793, a mutation at nucleotide position 794, and a mutation at nucleotide position 795.

In certain embodiments, a polynucleotide encoding Ldc2 S111C/N262T/K265N or Ldc2 S111X/N262X'/K265X" may undergo further codon optimization for optimal polypeptide expression in a particular microorganism (e.g., *E. coli, H. alvei*, or *P. aeruginosa*).

In certain embodiments, the mutant of Ldc2 (SEQ ID NO: 4) comprises one or more mutations selected from the group consisting of a mutation at amino acid position 111 to X, a mutation at amino acid position 262 to X', and a mutation at amino acid position 265 to X" (i.e. "Ldc2 111/262/265"). In certain embodiments, X, X', and X" are independently selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine; and with the proviso that X is not serine, X' is not asparagine, and X" is not lysine.

Accordingly, the polynucleotide encoding Ldc2 111/262/ 265 comprises, consists of, or consists essentially of a polynucleotide encoding Ldc2 (e.g. ldc2 (SEQ ID NO: 3), a codon optimized ldc2 (e.g. ldc2-co1, SEQ ID NO: 17)) containing one or more suitable nucleotide mutations selected from the group consisting of a mutation at nucleotide position 331, a mutation at nucleotide position 332, a mutation at nucleotide position 333, a mutation at nucleotide position 784, a mutation at nucleotide position 785, a mutation at nucleotide position 786, a mutation at nucleotide position 793, a mutation at nucleotide position 794, and a mutation at nucleotide position 795.

In certain embodiments, the polynucleotide described herein may be a recombinant or non-naturally occurring polynucleotide sequence. In certain embodiments, the polynucleotide sequence may be a cDNA.

Another aspect of the invention relates to a first expression plasmid vector comprising, consisting of, or consisting essentially of a fifth polynucleotide encoding one or more fifth polypeptides comprising, consisting of, or consisting essentially of one or more sixth polypeptides selected from the group consisting of Ldc2, fragments of Ldc2, and mutants of Ldc2; and a backbone plasmid capable of autonomous replication in a host cell. A sixth polynucleotide encodes a sixth polypeptide. In certain embodiments, the fifth polynucleotides are the same as the first polynucleotide as described supra, the fifth polypeptides are the same as the first polypeptide as described supra, the sixth polynucleotides are the same as the second polypeptide as described supra, and the sixth polypeptides are the same as the second polynucleotide as described supra. In certain embodiments, the host cell is a *P. aeruginosa* cell. In certain embodiments, the host cell is not a *P. aeruginosa* cell.

In certain embodiments, the first expression plasmid vector further comprises an antitoxin polynucleotide that counteracts a toxin polypeptide that is harmful to the host cell, and optionally a toxin polynucleotide encoding the toxin polypeptide. The toxin and antitoxin polynucleotides, and the toxin polypeptide are the same as further described below.

Another aspect of the invention relates to a second expression plasmid vector comprising, consisting of, or consisting essentially of a seventh polynucleotide encoding one or more seventh polypeptides comprising, consisting of, or consisting essentially of one or more eighth polypeptides selected from the group consisting of Ldc2, fragments of Ldc2, and mutants of Ldc2; and a backbone plasmid capable of autonomous replication in a host cell. An eighth polynucleotide encodes an eighth polypeptide. In certain embodiments, the seventh polynucleotides are the same as the third polynucleotide as described supra, the seventh polypeptides are the same as the third polypeptide as described supra, the eighth polynucleotides are the same as the fourth polypeptide as described supra, and the eighth polypeptides are the same as the fourth polynucleotide as described supra. In certain embodiments, the host cell is a *P. aeruginosa* cell. In certain embodiments, the host cell is not a *P. aeruginosa* cell.

In certain embodiments, heterologous expression of Ldc2 using the second expression plasmid vector comprising a mutant ldc2 (e.g. ldc2-co1 (SEQ ID NO: 17)) results in the same or greater cadaverine production than heterologous expression of Ldc2 using the second expression plasmid vector comprising ldc2. In certain embodiments, a fragment or mutant of Ldc2 exhibits lysine decarboxylase activity and/or increases cadaverine production when expressed in a host cell. In certain embodiments, heterologous expression of the fragment or mutant of Ldc2 in a host cell results in the same or greater cadaverine production than heterologous expression of Ldc2.

In certain embodiments, the second expression plasmid vector further comprises an antitoxin polynucleotide that counteracts a toxin polypeptide that is harmful to the host cell, and optionally a toxin polynucleotide encoding the toxin polypeptide. The toxin and antitoxin polynucleotides, and the toxin polypeptide are the same as further described below.

As used herein, the term "host cell" refers to a microorganism cell that may be any cell that can be transformed with an expression plasmid vector (e.g., *Pseudomonas* (e.g., *P. aeruginosa*), *Escherichia* (e.g., *E. coli*), *Corynebacterium* (e.g., *Corynebacterium glutamicum*), *Bacilli*, *Hafnia* (e.g., *Hafnia alvei*), *Brevibacterium*, *Lactobacillus* (e.g., *Lactobacillus pentosus*, *Lactobacillus plantarum*, *Lactobacillus saerimneri*), *Lactococcus* (e.g., *Lactococcus lactis*, *Lactococcus lactis* ssp. *cremoris*, *Lactococcus lactis* ssp. *lactis*), and *Streptococcus* (e.g., *Streptococcus thermophilus*)). In certain embodiments, the host cell may be any cell that is not a *P. aeruginosa* cell.

An *E. coli* cell may be any of the *E. coli* strains derived from *E. coli* K12 (e.g., MG1655, W3110, DH10b, DH1, BW2952 and strains derived therefrom) or *E. coli* B, or strains derived therefrom.

In certain embodiments, the host cell may contain one or more endogenous plasmids. In certain embodiments, the host cell does not contain endogenous plasmids. The term "cure" as used herein means to remove one or more endogenous plasmids from a host cell. In certain embodiments, a host cell may be "cured" of all endogenous plasmids by removing all endogenous plasmids from the host cell. In certain embodiments, a host cell may be "cured" of one or more endogenous plasmids by removing only the one or more endogenous plasmids that is targeted for removal from the cell.

In certain embodiments, the host cell may be a prokaryotic cell (e.g. is, *H. alvei*) containing endogenous plasmids that encode specific toxin/antitoxin gene pairs. Such toxin/antitoxin gene pairs play a role in maintenance of the genetic information and response to stress. (See, Wertz et al. "Chimeric nature of two plasmids of *Hafnia alvei* encoding the bacteriocins alveicins A and B." Journal of Bacteriology, (2004) 186: 1598-1605.) As long as the cell has one or more plasmids comprising an antitoxin gene, the toxin is neutralized by the antitoxin that is continuously expressed by the one or more plasmids to keep the cells alive. In certain prokaryotes, the antitoxin protein degrades faster than the toxin protein. If the plasmid comprising the antitoxin gene is lost from the cell, the toxin protein will exist longer than the antitoxin protein in the cell and kill or inhibit the growth of the cell. Therefore, plasmids comprising the antitoxin or the toxin/antitoxin gene are preferably maintained to keep the host cell alive.

As used herein, a toxin/antitoxin gene pair has two genes, one is a toxin gene which expresses a polypeptide toxic to a host cell, and the other is an antitoxin gene which neutralizes the toxic polypeptide in the host cell. Examples of the toxin/antitoxin gene pair include, without limitation, abt/abi gene pair and aat/aai gene pair, fragments thereof, and mutants thereof. In some embodiments, the toxin polynucleotide sequence comprises, consists of, or consists essentially of the nucleotide sequence of SEQ ID NO: 7 or SEQ ID NO: 9, fragments thereof, or mutants thereof. In some embodiments, the antitoxin polynucleotide sequence comprises, consists of, or consists essentially of the nucleotide sequence of SEQ ID NO: 8 or SEQ ID NO: 10, fragments thereof, or mutants thereof.

In certain embodiments, the host cell may be any *H. alvei* strain, e.g., endogenous plasmid-free *H. alvei* strains or *H. alvei* strains containing endogenous plasmids. For example, the host cell may be an *H. alvei* strain containing one or more pAlvA plasmids or the cured strains thereof (pAlvA-strains), or an *H. alvei* strain containing one or more pAlvB plasmids and the cured strains thereof (pAlvB-strains).

In certain embodiments, the expression plasmid vector disclosed herein (e.g. the first or the second expression plasmid vector) may further comprise one or more antitoxin genes selected from the group consisting of abi gene, aai gene, mutations and fragments thereof, and/or one or more toxin/antitoxin gene pairs selected from the group consisting of abt/abi gene pair and aat/aai gene pair, and mutations and fragments thereof. For example, in certain embodiments, an expression plasmid vector (e.g. the first or the second expression plasmid vector) may further comprise an antitoxin polynucleotide that counteracts a toxin polypeptide that is harmful to the host cell, and a toxin polynucleotide sequence encoding the toxin polypeptide.

In certain embodiments, the host cell is an industrial strain suitable for use in industrial-scale or large-scale production. For example, industrial strains may be cultivated in a fermenter. The scale of culture may range from hundreds of liters to millions of liters. On the other hand, a laboratory strain is usually cultivated in a few liters or less. In certain embodiments, an industrial strain may grow in a simpler or more economical medium than laboratory strains.

A backbone plasmid capable of autonomous replication in a host cell may be any plasmid that can replicate in the host cell. In one embodiment, an expression plasmid vector comprises a backbone plasmid that can replicate in *E. coli*. In another embodiment, an expression plasmid vector comprises a backbone plasmid that can replicate in *H. alvei*. Examples of the backbone plasmids include, without limitation, backbone plasmids that can replicate in *E. coli* strains, e.g. pUC (e.g. pUC18 and pUC19 plasmids), pBR322, pSC101, p15a, pACYC, pET, and pSC101 plasmids, and plasmids derived therefrom.

In certain embodiments, the mutants of a polynucleotide can be obtained from codon optimization of the polynucleotide for a particular microorganism (e.g., *E. coli, H. alvei*, or *P. aeruginosa*) to enhance polypeptide expression.

A promoter is a region of DNA that initiates transcription of a particular gene. In certain embodiments, an expression plasmid vector may contain one or more promoter polynucleotide sequences. For example, a promoter polynucleotide sequence comprising, consisting of, or consisting essentially of the polynucleotide sequence of SEQ ID NO: 5 may be positioned upstream from the polynucleotide. In certain embodiments, the promoter sequence may be synthesized using the primers psyn-1 and psyn-2 (see FIG. 3) and further inserted into pUC18. In some embodiments, the expression plasmid vector may contain one or more lac promoter polynucleotide sequences and one or more synthetic promoter polynucleotide sequences. In some embodiments, the expression plasmid vector may contain only a lac promoter polynucleotide sequence or a synthetic promoter sequence.

Another aspect of the invention relates to a first transformant comprising the first expression plasmid vector disclosed herein in a host cell, wherein the first expression plasmid vector comprises, consists, or consists essentially of:

a fifth polynucleotide encoding one or more fifth polypeptide comprising, consisting of, or consisting essentially of one or more sixth polypeptides selected from the group consisting of Ldc2, fragments of Ldc2, and mutants of Ldc2; and a backbone plasmid capable of autonomous replication in the host cell.

A sixth polynucleotide encodes a sixth polypeptide. The host cell, the fifth polynucleotide, the fifth polypeptides, the sixth polynucleotides and the sixth polypeptides are the same as described supra.

As used herein, a transformant is a host cell that has been altered by introducing one or more expression plasmid vectors in the host cell. In certain embodiments, the transformant is obtained by introducing an expression plasmid vector through transformation into a host cell displaying competence to the plasmid vector.

In certain embodiments, the host cell is a *P. aeruginosa* cell. In one example, the sixth polypeptide is Ldc2, a sixth polynucleotide encodes the sixth polypeptide and is a mutant ldc2, e.g., a codon optimized ldc2 (e.g. ldc2-co1) for optimal polypeptide expression in a particular microorganism (e.g., *E. coli, H. alvei*).

In certain embodiments, the host cell is not a *P. aeruginosa* cell.

Another aspect of the invention relates to a second transformant comprising the second expression plasmid vector in a host cell, wherein the expression plasmid vector comprises, consists, or consists essentially of:

a seventh polynucleotide encoding one or more seventh polypeptides comprising, consisting of, or consisting essentially of one or more eighth polypeptides selected from the group consisting of Ldc2, fragments of Ldc2, and mutants of Ldc2.

An eighth polynucleotide encodes an eighth polypeptide. The host cell, the seventh polynucleotide, the seventh polypeptides, the seventh polynucleotides, and the eighth polypeptides are the same as described supra.

In certain embodiments, the host cell is a *P. aeruginosa* cell.

In certain embodiments, the host cell is not a *P. aeruginosa* cell, the eighth polypeptide is Ldc2, an eighth polynucleotide encodes the eight polypeptide and is not ldc2, e.g. a codon optimized ldc2 (e.g. ldc2-co1) for optimal polypeptide expression in a host cell (e.g., *E. coli, H. alvei*).

In certain embodiments, the expression plasmid vector (e.g., the first or the second expression plasmid vector) transformed into the transformant disclosed herein (e.g., the first or the second transformant) further comprises an antitoxin polynucleotide that counteracts a toxin polypeptide that is harmful to the host cell, and optionally a toxin polynucleotide sequence encoding the toxin polypeptide, and the transformant may be further altered by introducing an expression plasmid vector into the host cell comprising the toxin polynucleotide sequence encoding the toxin polypeptide, and optionally the antitoxin polynucleotide that counteracts the toxin polypeptide.

Another aspect of the invention relates to a first mutant host cell comprising a first or third polynucleotide as disclosed herein, wherein the first or third polynucleotide has been integrated into a chromosome of the host cell. The first or third polynucleotide is the same as described supra.

In certain embodiments, the first or third polynucleotide has been codon optimized as described supra. In certain embodiments, the first or third polynucleotide encodes one or more polypeptides comprising, consisting of, or consisting essentially of Ldc2 and/or one or more Ldc2 mutants selected from the group consisting of SEQ ID NO: 6 (Ldc2 S111C), SEQ ID NO: 11 (Ldc2 N262T), SEQ ID NO: 12 (Ldc2 K265N), SEQ ID NO: 13 (Ldc2 S111C/N262T), SEQ ID NO: 14 (Ldc2 S111C/K265N), SEQ ID NO: 15 (Ldc2 N262T/K265N), SEQ ID NO: 16 (Ldc2 S111C/N262T/K265N), and Ldc2 111/262/265.

In certain embodiments, the first or third polynucleotide may be integrated into the host cell chromosome according to the PCR-mediated gene replacement method (see, e.g. Datsenko, 2000 for an overview of the PCR-mediated gene replacement method, which is incorporated herein by reference in its entirety). Integrated chromosomes may also be produced by other suitable methods.

Another aspect of the invention relates to a method for producing *P. aeruginosa* Ldc2, a fragment of Ldc2, or a mutant of Ldc2 comprising:

obtaining the first transformant, the second transformant, and/or the first mutant host cell as disclosed herein (e.g. the first and/or the second transformant);

culturing the first transformant, the second transformant and/or the first mutant host cell under conditions effective for the expression of the polypeptide; and harvesting the polypeptide.

The first transformant, the second transformant and/or the first mutant host cell may be cultured using a medium containing carbon sources and non-carbon nutrient sources. Examples of carbon sources include, without limitation, sugar (e.g. carbohydrates such as glucose and fructose), oil and/or fat, fatty acid, and/or derivatives thereof. The oil and fat may contain saturated and/or unsaturated fatty acids having 10 or more carbon atoms, e.g. coconut oil, palm oil, palm kernel oil, and the like. The fatty acid may be a saturated and/or unsaturated fatty acid, e.g. hexanoic acid, octanoic acid, decanoic acid, lauric acid, oleic acid, palmitic acid, linoleic acid, linolenic acid, myristic acid, and the like. Examples of derivatives of a fatty acid include, without limitation, esters and salts thereof. Examples of non-carbon sources include, without limitation, nitrogen sources, inorganic salts, and other organic nutrient sources.

For example, a medium may contain a carbon source assimilable by the transformant and/or mutant host cell, optionally with one or more other source selected from the group consisting of a nitrogen source, an inorganic salt and another organic nutrient source. In certain embodiments, the weight percentage of the nitrogen source is about 0.01 to about 0.1% of the medium. Examples of the nitrogen source may comprise ammonia, ammonium salts (e.g. ammonium chloride, ammonium sulfate and ammonium phosphate), peptone, meat extract, yeast extract, and the like. Examples of the inorganic salts include, without limitation, potassium dihydrogen phosphate, dipotassium hydrogen phosphate, magnesium phosphate, magnesium sulfate, sodium chloride, and the like. Examples of the other organic nutrient source include, without limitation, amino acids (e.g. glycine, alanine, serine, threonine and proline), vitamins (e.g. vitamin B1, vitamin B12 and vitamin C), and the like.

The culture may be carried out at any temperature as long as the cells can grow, and preferably at about 20° C. to about 40° C., or about 35° C. The culture period may be about 1, about 2, about 3, about 4, about 5, about 6, about 7, about 8, about 9, or about 10 days.

In one embodiment, the first transformant, the second transformant and/or the first mutant host cell is cultured in a medium containing peptides, peptones, vitamins (e.g. B vitamins), trace elements (e.g. nitrogen, sulfur, magnesium), and minerals. Examples of such medium include, without limitation, commonly known Lysogeny broth (LB) mediums comprising tryptone, yeast extract and NaCl suspended in water (e.g. distilled or deionized).

Another aspect of the invention relates to a method for producing cadaverine (1,5-pentanediamine) comprising:

1a) cultivating the first transformant, the second transformant and/or the first mutant host cell as disclosed herein;

1b) producing cadaverine using culture obtained from step 1a to decarboxylate lysine; and 1c) extracting and purifying cadaverine using the culture obtained from step 1b.

Cultivating the first transformant, the second transformant and/or the first mutant host cell may comprise the steps of culturing the transformant or mutant host cell as described supra.

As used herein, "using the culture obtained from step 1a" may comprise further processes of the culture obtained from step 1a. For example, using a buffer solution to dilute the culture; centrifuging the culture to collect the cells; resuspending the cells in a buffer solution; or lysing the cells into cell lysate; or/and purifying lysine decarboxylase from the cell lysate.

In another embodiment, step 1c of the method further comprises the following steps:

1c1) separating the solid and liquid components of the reaction obtained from step 1b;

1c2) adjusting the pH of the liquid component obtained from step 1c1 to about 14 or higher;

1c3) removing water from the liquid component obtained from step 1c2; and

1c4) recovering cadaverine.

In step 1c1, the separation of the solid and liquid components of the reaction of step 1b may be accomplished by conventional centrifugation and/or filtration.

In step 1c2, the pH of the liquid component of step 1c1 may be adjusted by adding a base, e.g. NaOH. NaOH may be added as a solid and/or a solution (e.g. an aqueous solution).

In step 1c3, the water may be removed by distillation at ambient pressure or under vacuum.

In step 1c4, cadaverine may be recovered by distillation at ambient pressure or under vacuum.

Another aspect of the invention relates to biobased cadaverine prepared according to the method disclosed herein.

As used herein, a "biobased" compound means the compound is considered biobased under Standard ASTM D6866.

Another aspect of the invention relates to a polyamide having a structure of Structure 1:

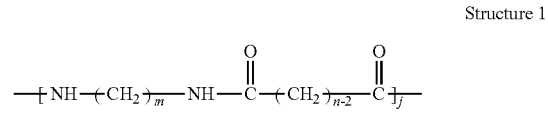

including stereoisomers thereof, wherein:

m=4, 5, 6, 7, 8, 9, 10, 11, 12, 13, 14, 15, 16, 17, 18, 19, 20, 21, or 22;

n=4, 5, 6, 7, 8, 9, 10, 11, 12, 13, 14, 15, 16, 17, 18, 19, 20, 21, or 22;

j=about 100~about 1,000,000; and the polyamide is prepared from one or more diamines having carbon numbers of m and one or more dicarboxylic acids having carbon numbers of n, at least one of the diamines and dicarboxylic acids comprises biobased carbon under Standard ASTM D6866, and the m or n of each diamine or dicarboxylic acid can be the same or different.

In one embodiment, the diamine is biobased cadaverine, more preferably biobased cadaverine prepared according to the method disclosed herein. Examples of the dicarboxylic acids include, without limitation, $C_{10}$dicarboxylic acid, $C_{11}$dicarboxylic acid, $C_{12}$dicarboxylic acid, $C_{13}$dicarboxylic acid, $C_{14}$dicarboxylic acid, $C_{16}$dicarboxylic acid, $C_{18}$dicarboxylic acid, and any combinations thereof. In certain embodiments, all or part of the $C_n$dicarboxylic acids are biobased.

In another embodiment, the polyamide has a structure described above, wherein:

the polyamide is formed by reacting biobased cadaverine with one or more dicarboxylic acids, more preferably the biobased cadaverine is prepared according to the method disclosed herein;

n=4, 5, 6, 7, 8, 9, 10, 11, 12, 13, 14, 15, 16, 17, 18, 19, 20, 21, or 22;

j=about 100 to about 1,000,000, about 1000 to about 100,000, or about 1000 to about 10,000; and the dicarboxylic acids comprise biobased carbon under Standard ASTM D6866.

Another aspect of the invention relates to a method for making the polyamides disclosed herein comprising preparing biobased cadaverine as the $C_m$diamine according to the method disclosed herein.

In one embodiment, the method further comprises preparing one or more biobased $C_n$dicarboxylic acids.

In another embodiment, the method further comprises preparing the polyamide by reacting biobased cadaverine with one or more biobased $C_n$dicarboxylic acids.

Another aspect of the invention relates to a composition comprising one or more polyamides disclosed herein.

In one embodiment, the diamine is biobased cadaverine, more preferably biobased cadaverine prepared according to the method disclosed herein. Examples of the dicarboxylic acids include, without limitation, $C_{10}$dicarboxylic acid, $C_{11}$dicarboxylic acid, $C_{12}$dicarboxylic acid, $C_{13}$dicarboxylic acid, $C_{14}$dicarboxylic acid, $C_{16}$dicarboxylic acid, $C_{18}$dicarboxylic acid, and any combinations thereof. In certain embodiments, all or part of the $C_n$dicarboxylic acids are biobased.

In another embodiment, the polyamide has a structure described above, wherein:
  the polyamide is formed by reacting biobased cadaverine with one or more dicarboxylic acids, more preferably the biobased cadaverine is prepared according to the method disclosed herein;
  n=4, 5, 6, 7, 8, 9, 10, 11, 12, 13, 14, 15, 16, 17, 18, 19, 20, 21, or 22;
  j=about 100 to about 1,000,000, about 1000 to about 100,000, or about 1000 to about 10,000; and
  the dicarboxylic acids comprise biobased carbon under Standard ASTM D6866.

Another aspect of the invention relates to a method for preparing 1,5-diisocyanatopentane comprising:
  2a) preparing biobased cadaverine as disclosed herein; and
  2b) converting biobased cadaverine obtained from step 2a to 1,5-diisocyanatopentane.

Step 2b may comprise using any known method to convert diamine into isocyanate. An example of said method is the traditional phosgene method, which includes one-step high temperature phosgene method (i.e. mixing phosgene with diamine at high temperature to obtain isocyanate), the improved two-step phosgene method, and the triphosgene method in which triphosgene is used instead of phosgene. There are also other methods that do not use phosgene as a raw material. An example of said method is hexanediamine carbonylation which uses $CO_2$ instead of phosgene: $CO_2$ is added into a solution of a primary amine and an organic base, then a proper amount of phosphorus electrophilic reagents is added into the reaction solution to start an exothermic dehydration reaction to obtain isocyanate. Another example is carbamate thermal decomposition method wherein a primary amine is converted to a carbamate, and then the carbamate is heated to decompose and generate isocyanate.

The abbreviations used for the amino acids, polypeptides, base sequences, and nucleic acids are based on the abbreviations specified in the IUPAC-IUB Communication on Biochemical Nomenclature, Eur. J. Biochem., 138:9 (1984), "Guideline for Preparing Specifications Including Base Sequences and Amino Acid Sequences" (United States Patent and Trademark Office), and those commonly used in this technical field.

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. The words "herein," "above," "below," "supra," and words of similar import; when used in this application, refer to this application as a whole and not to any particular portions of this application. Where the context permits, words in the above Detailed Description using the singular or plural number may also include the plural or singular number respectively. The words "or," and "and/or" in reference to a list of two or more items, covers all of the following interpretations of the word: any of the items in the list, all of the items in the list, and any combination of the items in the list.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1

Figure 2:
FIG. 2: A protein tree generated from a sequence similarity search for the E. coli protein LdcC (highlighted) using BLAST.

P. aeruginosa Polypeptide Sequences are not Similar to Escherichia coli CadA or LdcC Lysine Decarboxylase Sequences In order to identify novel lysine decarboxylases, E. coli lysine decarboxylase polypeptides CadA and LdcC were used as BLAST queries to identify similar protein sequences from organisms that were not E. coli. The non-redundant (nr) polypeptide sequence database was used, and E. coli (taxid: 562) was excluded from the search. The BLAST results showing polypeptides with similar sequences are displayed as protein trees in FIG. 1 for CadA and FIG. 2 for LdcC. Notably, lysine decarboxylases from pseudomonads (e.g. P. aeruginosa) did not show up in the BLAST search results as illustrated in FIGS. 1 and 2.

Example 2

Construction of P. aeruginosa ldc1 and ldc2 Expression Plasmid Vectors and E. coli Strains The genomic DNA of P. aeruginosa PAO1 (Accession: NC_002516) was purchased from DSMZ (Leibniz Institute DSMZ-German Collection of Microorganisms and Cell Cultures) (DSM No. 22644) and used as template DNA for PCR. PCR primers ldc1-1 and ldc1-2 (FIG. 3) were designed based on a gene from P. aeruginosa PA21_ST175 (Accession: EME94559.1), which was designated ldc1. The nucleotide sequence of ldc1 is provided in SEQ ID NO: 1 and the Ldc1 protein sequence is provided in SEQ ID NO: 2. Ldc1-1 and ldc1-2 primers were used to amplify ldc1 (SEQ ID NO: 1).

PCR primers ldc2-1 and ldc2-2 (FIG. 3) were designed based on a gene from P. aeruginosa RP73 (Accession: WP_014603046.1), which was designated ldc2. The nucleotide sequence for ldc2 is provided in SEQ ID NO: 3 and the Ldc2 protein sequence is provided in SEQ ID NO: 4. The primers ldc2-1 and ldc2-2 were used to amplify ldc2 (SEQ ID NO: 3).

Figure 4:
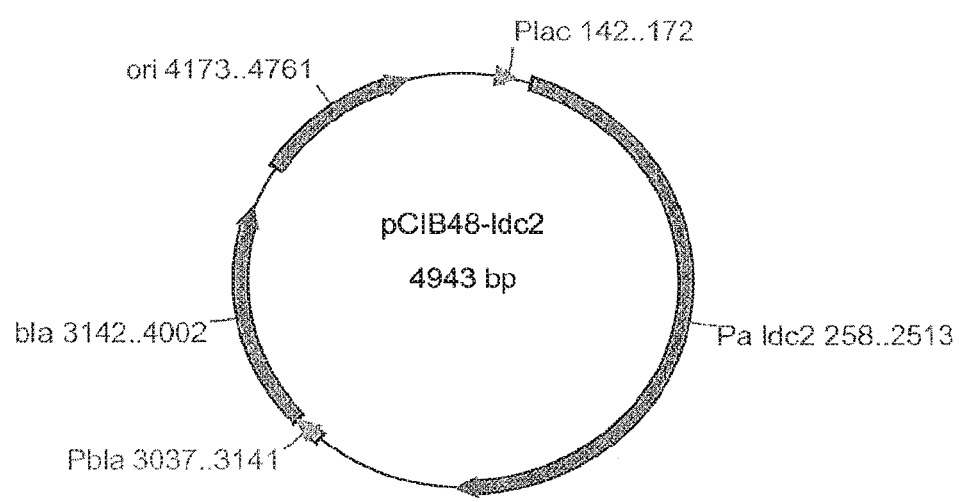
FIG. 4: Recombinant expression plasmid vector maps used to express a P. aeruginosa protein having the sequence of SEQ ID NO: 2 (hereinafter "Ldc1") and Ldc2 proteins according to an embodiment of the invention. A) a vector map for pCIB10; B) a vector map for pCIB45; C) a vector map for pCIB46; D) a vector map for pCIB47; and E) a vector map for pCIB48.

Recombinant expression plasmid vectors containing either ldc1 or ldc2 genes were constructed. The respective genes were inserted into either a pUC18 plasmid vector or a pUC18 plasmid vector containing a synthetic promoter (pCIB10) (FIG. 4A). The synthetic promoter sequence (SEQ ID NO: 5) was synthesized using the PCR primers psyn-1 and psyn-2 (FIG. 3). Primer psyn-1 contains the promoter sequence and a sequence homologous to pUC18, and primer psyn-2 contains a sequence homologous to pUC18. These two PCR primers were used to amplify a portion of pUC18 that includes the multi-cloning site from the plasmid inserted downstream of the synthetic promoter sequence. Restriction enzymes EcoRI and ScaI were used to digest the amplified DNA containing the synthetic promoter, which was further ligated into pUC18 to construct pCIB10 (FIG. 4A, the synthetic promoter is represented as "Pcp25"). The amplified DNA fragments of ldc1 and ldc2 were digested with the restrictions enzymes SacI and XbaI, and ligated into pUC18 to construct pCIB45 (FIG. 4B) and pCIB48 (FIG. 4E), or pCIB10 to construct pCIB46 (FIG. 4C) and pCIB47 (FIG. 4D).

Bacterial strains were constructed by transforming pCIB45-48 into *E. coli* MG1655 K12. pUC18 was transformed into *E. coli* MG1655 K12 as a negative control.

Example 3

Production of Cadaverine by Heterologous Expression of *P. aeruginosa* Ldc1 and Ldc2 in *E. coli*

A single colony of each *E. coli* strain containing either empty vector or a *P. aeruginosa* ldc1 or a ldc2 recombinant expression plasmid vector (strains CIB45-46 and CIB 47-48, respectively) was grown overnight in Lysogeny broth (LB) medium with ampicillin (100 µg/mL) in a 4 mL culture at 37° C. The following day, each culture was inoculated into 4 mL of fresh LB medium with ampicillin (100 µg/mL) to a final optical density (OD) of 0.05, measured at absorbance 600 nm ($OD_{600}$). Each culture was grown at 30° C. for 4 hours before adding lysine-HCl and pyridoxal-phosphate (PLP) to a final concentration of 20 g/L and 0.1 mM, respectively. Each culture was grown for an additional 24 hours before measuring the final $OD_{600}$ and cadaverine concentration. Cadaverine was identified and quantified using nuclear magnetic resonance (NMR) (Table 1).

TABLE 1

Production of cadaverine by heterologous expression of *P. aeruginosa* Ldc1 and Ldc2 in *E. coli*.

| Strain | Host | Promoter | Enzyme | Polynucleotide encoding the enzyme | Cadaverine* |
|---|---|---|---|---|---|
| +N.C. | *E. coli* | $P_{lac}$ | None | None | 0.50 |
| CIB45 | *E. coli* | $P_{lac}$ | Ldc1 | ldc1 | 0.05 |
| CIB46 | *E. coli* | $P_{synthetic}$ | Ldc1 | ldc1 | 0.40 |
| CIB47 | *E. coli* | $P_{synthetic}$ | Ldc2 | ldc2 | 1.07 |
| CIB48 | *E. coli* | $P_{lac}$ | Ldc2 | ldc2 | 1.32 |

+N.C.: negative control pUC18
*g/kg sample weight

As provided in Table 1, *E. coli* strains expressing *P. aeruginosa* Ldc2 (C11347 and 48) showed a higher yield of cadaverine produced compared with the *E. coli* strains expressing *P. aeruginosa* Ldc1 (CIB45 and CIB46). The strains expressing Ldc1 all showed a yield of cadaverine production less than that of the negative control (N.C.) (Table 1). Thus, these results demonstrate that heterologous expression of *P. aeruginosa* Ldc2 in *E. coli* affected the production of cadaverine.

Example 4

Construction of Codon-Optimized *P. aeruginosa* ldc2 Recombinant Expression Plasmid Vectors in *E. coli* and *H. alvei* Strains The nucleotide sequence of the ldc2 gene was codon optimized for expression in *E. coli* (ldc2-co1, SEQ ID NO: 17). The codon-optimized sequence was cloned into pUC18 and pCIB10 using the restriction enzymes SacI and XbaI to generate the plasmids pCIB65 and pCIB66, respectively. Positive controls were constructed by cloning wild-type *E. coli* cadA into pUC18 and pCIB10 to generate pCIB60 and pCIB61, respectively. Plasmids pCIB60 and pCIB65 were transformed into *E. coli* MG1655 K12 to generate strains CIB60 and CIB65. Plasmids pCIB61 and pCIB66 were transformed into *H. alvei* to generate strains CIB61 and CIB66.

Example 5

Production of Cadaverine by *P. aeruginosa* Ldc2 and *E. coli* CadA Expressed in *E. coli* and *H. alvei*

A single colony of each *E. coli* and *H. alvei* strain (strains CIB48, CIB60, CIB61, CIB65, and CIB66) was grown overnight in LB medium with ampicillin (100 µg/mL) in a 2.5 mL culture at 29° C. *E. coli* and *H. alvei* transformed with the empty vector pUC18 were used as negative controls. The following day, minimal medium with ampicillin (100 µg/mL), and lysine-HCl and PLP to a final concentration of 20 g/L and 0.1 mM, respectively. Each culture was incubated at 37° C. for 5 hours. One milliliter of sample was taken from each culture to quantify cadaverine production using NMR.

TABLE 2

Cadaverine produced by *P. aeruginosa* Ldc2 and *E. coli* CadA expressed in *E. coli* and *H. alvei*.

| Strain | Host | Enzyme | Polynucleotide encoding the enzyme | Cadaverine* |
|---|---|---|---|---|
| | *E. coli* | none | none | 0.20 |
| CIB60 | *E. coli* | CadA | cadA | 5.81 ± 1.5 |
| CIB48 | *E. coli* | Ldc2 | ldc2 | 6.02 ± 1.67 |
| CIB65 | *E. coli* | Ldc2 | ldc2-co1 | 6.54 ± 0.022 |
| | *H. alvei* | none | none | 1.27 |
| CIB61 | *H. alvei* | CadA | cadA | 6.62 ± 0.46 |
| CIB66 | *H. alvei* | Ldc2 | ldc2-co1 | 9.60 ± 1.7 |

*g/kg sample weight

As provided in Table 2, *E. coli* cells expressing the Ldc2 protein, produced from ldc2 or ldc2-co1 DNA, showed higher yields of cadaverine production (6.02 g/kg and 6.54 g/kg) compared to *E. coli* cells expressing the CadA protein (5.81 g/kg). Notably, *E. coli* cells expressing the Ldc2 protein produced from ldc2-co1 DNA showed higher yields of cadaverine production (6.54 g/kg) compared to *E. coli* cells expressing the Ldc2 protein produced from ldc2 DNA (6.02 g/kg). Additionally, *H. alvei* cells expressing the Ldc2 protein (produced from ldc2-co1 DNA) showed higher yields of cadaverine production (9.60 g/kg) compared to *H. alvei* cells expressing the CadA protein (6.62 g/kg).

Example 6

Construction and Expression of the *P. aeruginosa* Ldc2 S111C Mutant

The serine at amino acid position 111 in *P. aeruginosa* Ldc2 is conserved across lysine decarboxylases from various species, including *E. coli, Shigella sonnei*, and *Salmonella enterica* as indicated by the sequence alignment provided in FIG. 5. The codon optimized *P. aeruginosa* ldc2 gene (SEQ ID NO: 17) was mutated by generating a point mutation at nucleotide 332 (ldc2-co1 C332G (SEQ ID NO: 18)), which resulted in a substitution of serine at amino acid 111 with a cysteine (Ldc2 S111C) (SEQ ID NO: 6). ldc2-co1 C332G (SEQ ID NO: 18) was cloned into pUC18 and pCIB10 using the restriction enzymes SacI and XbaI to generate the plasmids pCIB67 and pCIB68, respectively. Plasmid pCIB67 was transformed into *E. coli* MG1655 K12 to generate strain CIB67, and pCIB68 was transformed into *H. alvei* to generate strain CIB68. Experiments to determine production were performed as described in Example 5. Briefly, a single colony of each strain was grown overnight in LB medium with ampicillin (100 µg/mL) in a 2.5 mL culture at 29° C. The following day, 2.5 mL minimal medium supplemented with ampicillin (100 µg/mL), and lysine-HCl and PLP to a final concentration of 20 g/L and 0.1 mM, respectively. Each culture was incubated at 37° C. for 5 hours. One milliliter of sample was taken from each culture to quantify cadaverine production using NMR.

TABLE 3

Cadaverine produced by *P. aeruginosa* Ldc2 S111C and *E. coli* CadA expressed in *E. coli* and *H. alvei*.

| Strain | Host | Enzyme | Polynucleotide encoding the enzyme | Cadaverine* |
|---|---|---|---|---|
|  | *E. coli* | none | none | 0.20 |
| CIB65 | *E. coli* | Ldc2 | ldc2-co1 | 6.54 ± 0.022 |
| CIB67 | *E. coli* | Ldc2 S111C | ldc2-co1 C332G | 9.88 ± 5.7 |
|  | *H. alvei* | none | none | 1.27 |
| CIB66 | *H. alvei* | Ldc2 | ldc2-co1 | 9.60 ± 1.7 |
| CIB68 | *H. alvei* | Ldc2 S111C | ldc2-co1 C332G | 8.58 ± 0.73 |

*g/kg sample weight

As indicated in Table 3, *E. coli* cells expressing the Ldc2 S111C mutant protein showed a much higher yield of cadaverine production (9.88 g/kg) as compared to *E. coli* cells expressing the wild-type Ldc2 protein (6.54 g/kg).

Example 7

Construction and Expression of the *P. aeruginosa* Ldc2 N262T Mutant

The asparagine at amino acid position 262 in *P. aeruginosa* Ldc2 is conserved across lysine decarboxylases from various species, including *E. coli, Shigella sonnei, Salmonella enterica* as indicated by the sequence alignment provided in FIG. 6. ldc2-co1 (SEQ ID NO: 17) was mutated by generating a point mutation at nucleotide 785 (ldc2-co1 A785C (SEQ ID NO: 19)), which resulted in a substitution of asparagine at amino acid 262 with threonine (Ldc2 N262T) (SEQ ID NO: 11). ldc2-co1 A785C (SEQ ID NO: 19) was cloned into pUC18 and pCIB10 using the restriction enzymes SacI and XbaI to generate the plasmids pCIB75. Plasmid pCIB75 was transformed into *E. coli* MG1655 K12 to generate strain CIB75.

Experiments to determine production were performed as described in Example 5. Briefly, a single colony of each strain was grown overnight in LB medium with ampicillin (100 µg/mL) in a 2.5 mL culture at 29° C. The following day, 2.5 mL minimal medium supplemented with 100 µg/mL ampicillin, and lysine-HCl and PLP to a final concentration of 20 g/L and 0.1 mM, respectively. Each culture was incubated at 37° C. for 5 hours. One milliliter of sample was taken from each culture to quantify cadaverine production using NMR.

TABLE 4

Cadaverine produced by *P. aeruginosa* Ldc2 N262T expressed in *E. coli*.

| Strain | Host | Enzyme | Polynucleotide encoding the enzyme | Cadaverine* |
|---|---|---|---|---|
|  | *E. coli* | none | none | 2.46 ± 1.4 |
| CIB65 | *E. coli* | Ldc2 | ldc2-co1 | 6.25 ± 0.87 |
| CIB75 | *E. coli* | Ldc2 N262T | ldc2-co1 A785C | 14.5 ± 4.2 |

*g/kg sample weight

As indicated in Table 4, *E. coli* strains expressing the Ldc2 N262T mutant protein showed a much higher yield of cadaverine production (14.5 g/kg) as compared to *E. coli* strains expressing the wild-type Ldc2 protein (6.25 g/kg).

Example 8

Construction and Expression of the *P. aeruginosa* Ldc2 K265N Mutant

The lysine at amino acid position 265 in *P. aeruginosa* Ldc2 is conserved across lysine decarboxylases from various species, including *E. coli, Shigella sonnei, Salmonella enterica* as indicated by the sequence alignment provided in FIG. 6. ldc2-co1 (SEQ ID NO: 17) was mutated by generating a point mutation at nucleotide 795 (ldc2-co1 A795C (SEQ ID NO: 20)), which resulted in a substitution of lysine at amino acid 265 with asparagine (Ldc2 K265N) (SEQ ID NO: 12). ldc2-co1 A795C (SEQ ID NO: 20) was cloned into pUC18 and pCIB10 using the restriction enzymes SacI and XbaI to generate the plasmids pCIB76. Plasmid pCIB76 was transformed into *E. coli* MG1655 K12 to generate strain CIB76.

Experiments to determine production were performed as described in Example 5. Briefly, a single colony of each strain was grown overnight in LB medium with ampicillin (100 µg/mL) in a 2.5 mL culture at 29° C. The following day, 2.5 mL minimal medium supplemented with 100 µg/mL ampicillin, and lysine-HCl and PLP to a final concentration of 20 g/L and 0.1 mM, respectively. Each culture was incubated at 37° C. for 5 hours. One milliliter of sample was taken from each culture to quantify cadaverine production using NMR.

TABLE 5

Cadaverine produced by *P. aeruginosa* Ldc2 K265N expressed in *E. coli*.

| Strain | Host | Enzyme | Polynucleotide encoding the enzyme | Cadaverine* |
|---|---|---|---|---|
|  | *E. coli* | none | none | 1.89 ± 0.74 |
| CIB65 | *E. coli* | Ldc2 | ldc2-co1 | 4.73 ± 0.94 |
| CIB76 | *E. coli* | Ldc2 K265N | ldc2-co1 A795C | 10.1 ± 6.5 |

*g/kg sample weight

As indicated in Table 5, *E. coli* cells expressing the Ldc2 K265N mutant protein showed a much higher yield of cadaverine production (10.1 g/kg) as compared to cells expressing the wild-type Ldc2 protein (4.73 g/kg).

Example 9

Integration of ldc2 into the *E. coli* Chromosome and Expression of Ldc2

Integration of ldc2 into the *E. coli* chromosome was performed according to the PCR-mediated gene replacement method as described in Datsenko et al, 2000. The ldc2-co1 gene of *P. aeruginosa* (SEQ ID NO: 17) was integrated into the *E. coli* MG1655 chromosome at the locus of the recA gene. This knock-out cassette was constructed by using sewing PCR to fuse four fragments together: 1) the 400 bp region upstream of recA, 2) ldc2 gene, 3) the cat gene that enables chloramphenicol resistance, and 4) the 400 bp region downstream of recA. The knockout cassette was transformed into MG1655 harboring the pKD46 Red recombinase expression plasmid. Transformants were grown on chloramphenicol plates to identify successful integrations, and gene disruptions were verified using colony PCR and sequencing. One clone that was isolated with the desired integration was labeled CIB96.

Experiments to verify integration and expression of Ldc2 from the chromosome demonstrating cadaverine production were performed as described in Example 5. Briefly, a single colony was grown overnight in LB medium with chloramphenicol (25 μg/mL) in a 2.5 mL culture at 29° C. The following day, 2.5 mL minimal medium supplemented with 25 μg/mL chloramphenicol, and lysine-HCl and PLP to a final concentration of 20 g/L and 0.1 mM, respectively. Each culture was incubated overnight at 37° C. One milliliter of sample was taken from each culture to quantify cadaverine production using NMR.

TABLE 6

Cadaverine produced by *P. aeruginosa* Ldc2 expressed in *E. coli*. with ldc2 integrated chromosome.

| Strain | Host | Enzyme | Polynucleotide encoding the enzyme | Cadaverine* |
|---|---|---|---|---|
|  | *E. coli* | none | none | 0.10 ± 0.09 |
| CIB96 | *E. coli* | Ldc2 | ldc2-co1 | 5.98 ± 0.05 |

*g/kg sample weight

As indicated in Table 6, *E. coli* cells containing ldc2-co1 integrated into the chromosome and expressing the Ldc2 protein showed a much higher yield of cadaverine production (5.98 g/kg) as compared to the negative control (*E. coli* cells with no integrated chromosome) (0.10 g/kg).

SEQUENCE LISTINGS

SEQ ID: NO 1 (Ldc1 DNA sequence)
ATGCCCTACGAAGCCGATGACTATCTTTCCCGGCACTTCCAGACCAGCGGCACCGACCTG
GCGCGGAAGGTCGACGAACTGGCGGCCCTTGCGGCTCCCGGCGACAGCCCCAATCTCGC
GCTCTACCGCGAGATGCTCTTCACCGTGACGCGCATGGCCCAGGCCGACCGCAACCGCT
GGGACGCCAAGATCATGCTGCAGACCCTGCGCGAGATGGAGCATGCCTTCAGCGTCCTC
GAGCAGTTCAAGCGGCGACGCAAGGTCACCGTGTTCGGCTCGGCGCGCACGCCGGTCGA
ACATCCGGTCTATGCCCTGGCGCGCAAGCTGGGCGAGGAACTGGCCCGCTACGACCTGA
TGGTGATCACCGGCGCCGGCGGCGGCATCATGGCCGCCGCCCACGAAGGCGCCGGGCT
GGAGAACAGCCTGGGCTTCAACATCACCCTGCCCTTCGAGCAGCACGCCAACCATACGGT
GGACGGCAGCGGCAACCTGCTGTCGTTCCACTTTTTCTTCCTGCGCAAGCTGTTCTTCGTC
AAGGAAGCCGACGCCCTGGTGCTCTGCCCCGGCGGCTTCGGCACCCTCGACGAGGCACT
GGAAGTGCTGACCCTGGTACAGACCGGCAAGAGTCCGCTGGTGCCGATCGTGCTGCTCG
ACCAGCCGGGCGGCCGCTACTGGGAACACGCCCTGGAGTTCATGCAGGAACAGTTGCTG
GAGAATCACTATATCCTGCCGGCCGACATGCGCCTGATGCGCCTGGTGCATTCGGCCGAA
GACGCGGTGAAGGAAATCGCCCAGTTCTACCGCAACTTCCACTCCAGCCGCTGGCTGAAA
GGCACTTTCGTGATTCGCCTGAACCACGCCCTGAACGAAGCCGCGCTGGCGCACCTGCAC
GAACACTTCGCCAGCCTCTGCCTGAGCGGCGGCTTCCAGCAGCAGGCCTACAGCGAGCA
GGAACAGGACGAACCGGAGTTCCGCAACCTGACCCGCCTCGCCTTCGTGTTCAACGGGC
GCGACCAGGGGCGGCTGCGGGAATTGCTGGACTACATCAACCTGCCGGAAAACTGGGAC
TGA SEQ ID: NO 2 (Ldc1 protein sequence)
MAALDELRQV APSIPLFLLF RQLRIEQLSS QLLDEVQGCF NLAAGPARFI AERIDSDLRE
WRAPAGPRRL RDYAPPVPRT PVSARYNGRA RLDLAPAKQW RIGSGSTAER LATPLNDLST
AYRKTSAGAP AAHAGDIAEA FRRALWEAAA RLAREDGDTW FFEILRGNPG PGIEAGRETP
AKRWHGLAET LDSSPRLDPL RVALSAPGLD SRGRPASFGV PAAVVCRYLR RHGIAPLRTG
DYRFLLLFPQ GARAEHAQPL VDRLCEFKRR HDDDAPLKQV LPELLDSSPL YRYIGLRELC
AMIHEASLRL HLTALADAAA RTAGHAALAP ATVYGHLVRD ETEAVAIDRL GGRVVASLVG
VHPAATPLLL PGERVAEESP ALIDYLLALQ AFGEHFPGFA PELQGIEIDE RGRYRVRCVR
PAALARGSVL RLATRRPD SEQ ID: NO 3 (Ldc2 DNA sequence)
ATGTATAAAGACCTCAAATTTCCCGTCCTCATCGTCCATCGCGACATCAAGGCCGACACCG
TTGCCGGCGAACGCGTGCGGGCATCGCCCACGAACTGGAGCAGGACGGCTTCAGCATT
CTCTCCACCGCCAGCTCCGCCGAGGGGCGCATCGTCGCTTCCACCCACCACGGCCTGGC
CTGCATTCTGGTCGCCGCCGAAGGTGCCGGGGAAAACCAGCGCCTGCTGCAGGATGTGG
TCGAACTGATCCGCGTGCCCGCGTGCGGGCGCCGCAATTGCCGATCTTCGCCCTCGGC
GAGCAGGTGACCATCGAGAACGCGCCGGCCGAGTCCATGGCCGACCTGCACCAGTTGCG
CGGCATCCTCTACCTGTTCGAAGACACCGTGCCGTTCCTCGCCCGCCAGGTCGCCCGGG
CGGCGCGCAACTACCTGGCCGGGCTGCTGCCGCCATTCTTCCGTGCGCTGGTCGAGCAC
ACCGCGCAGTCCAACTATTCCTGGCATACGCCGGGCCACGGCGGCGGTGTCGCCTATCG
CAAGAGTCCGGTGGGACAGGCGTTCCACCAGTTCTTCGGGGAGAACACGCTGCGTTCCG
ACCTGTCGGTCTCGGTCCCCGAGCTGGGATCGCTGCTGACCATACCGGCCCCCTGGCC
GAGGCCGAGGACCGTGCCGCGCGCAATTTCGGCGCCGACCATACCTTCTTCGTGATCAAT
GGCACTTCCACCGCGAACAAGATCGTCTGGCACTCCATGGTCGGTCGCGAAGACCTGGTG
CTGGTGGACCGCAACTGCCACAAGTCGATCCTCCACTCGATCATCATGACCGGGGCGATA
CCGCTCTACCTGACTCCGGAACGCAACGAACTGGGGATCATCGGGCCGATCCCGCTGAG
CGAATTCAGCAAGCAGTCGATCGCCGCGAAGATCGCCGCCAGCCCGCTGGCGCGCGCC
GCGAGCCGAAGGTGAAGCTGGCGTGGTGACTAACTCCACCTACGACGGCCTGTGCTAC
AACGCCGAGCTGATCAAGCAGACCCTCGGCGACAGCGTCGAGGTGTTGCACTTCGACGA
GGCTTGGTACGCCTATGCCGCGTTCCACGAGTTCTACGACGGACGCTATGGCATGGGCAC
CTCGCGCAGCGAGGAGGGACCCCTGGTGTTCGCCACCCACTCCACGCACAAGATGCTCG

```
CCGCCTTCAGCCAGGCCTCGATGATCCACGTGCAGGATGGCGGGACCCGGAAGCTGGAC
GTGGCGCGCTTCAACGAAGCCTTCATGATGCACATCTCGACCTCGCCGCAGTACGGCATC
ATCGCTTCGCTGGACGTGGCTTCGGCGATGATGGAAGGGCCCGCCGGGCGTTCGCTGAT
CCAGGAGACCTTCGACGAGGCCCTCAGCTTCCGCCGGGCCCTGGCCAACGTACGGCAGA
ACCTGGACCGGAACGACTGGTGGTTCGGCGTCTGGCAGCCGGAGCAGGTGGAGGGCAC
CGACCAGGTCGGCACCCATGACTGGGTGCTGGAGCCGAGCGCCGACTGGCACGGCTTCG
GCGATATCGCCGAAGACTACGTGCTGCTCGACCCGATCAAGGTCACCCTGACCACCCCGG
GCCTGAGCGCTGGCGGCAAGCTCAGCGAGCAGGGGATTCCGGCCGCCATCGTCAGCCG
CTTCCTCTGGGAGCGCGGGCTGGTGGTGGAGAAAACCGGTCTCTACTCCTTCCTGGTGCT
GTTCTCGATGGGCATCACCAAGGGCAAGTGGAGCACCCTGGTCACCGAACTGCTCGAATT
CAAGCGCTGTTACGACGCCAACCTGCCGCTGCTTGACGTCTTGCCCTCCGTGGCCCAGGC
CGGCGGCAAGCGCTACAACGGAGTGGGCCTGCGCGACCTCAGCGACGCCATGCACGCCA
GCTACCGCGACAACGCCACGGCGAAGGCCATGAAGCGCATGTACACGGTGCTGCCGGAG
GTCGCGATGCGGCCGTCCGAGGCCTACGACAAGCTGGTGCGCGGCGAGGTCGAGGCGG
TACCGATCGCTCGGTTGGAAGGGCGCATCGCGGCCGTCATGCTGGTACCCTATCCGCCG
GGTATCCCGCTGATCATGCCGGGTGAGCGCTTCACCGAGGCGACCCGCTCGATCCTCGA
CTATCTCGAGTTCGCGCGGACCTTCGAGCGCGCCTTCCCTGGTTTCGACTCCGATGTGCA
TGGCCTGCAGCATCAGGACGGACCGTCCGGGCGCTGCTATACCGTTGAATGCATAAAGGA
ATGA

SEQ ID: NO 4 (Ldc2 protein sequence)
MYKDLKFPVLIVHRDIKADTVAGERVRGIAHELEQDGFSILSTASSAEGRIVASTHHGLACILVAA
EGAGENQRLLQDVVELIRVARVRAPQLPIFALGEQVTIENAPAESMADLHQLRGILYLFEDTVPF
LARQVARAARNYLAGLLPPFFRALVEHTAQSNYSWHTPGHGGGVAYRKSPVGQAFHQFFGE
NTLRSDLSVSVPELGSLLDHTGPLAEAEDRAARNFGADHTFFVINGTSTANKIVWHSMVGRED
LVLVDRNCHKSILHSIIMTGAIPLYLTPERNELGIIGPIPLSEFSKQSIAAKIAASPLARGREPKVKL
AVVTNSTYDGLCYNAELIKQTLGDSVEVLHFDEAWYAYAAFHEFYDGRYGMGTSRSEEGPLVF
ATHSTHKMLAAFSQASMIHVQDGGTRKLDVARFNEAFMMHSTSPQYGIIASLDVASAMMEGP
AGRSLIQETFDEALSFRRALANVRQNLDRNDWWFGVWQPEQVEGTDQVGTHDWVLEPSAD
WHGFGDIAEDYVLLDPIKVTLTTPGLSAGGKLSEQGIPAAIVSRFLWERGLVVEKTGLYSFLVLF
SMGITKGKWSTLVTELLEFKRCYDANLPLLDVLPSVAQAGGKRYNGVGLRDLSDAMHASYRD
NATAKAMKRMYTVLPEVAMRPSEAYDKLVRGEVEAVPIARLEGRIAAVMLVPYPPGIPLIMPGE
RFTEATRSILDYLEFARTFERAFPGFDSDVHGLQHQDGPSGRCYTVECIKE SEQ ID: NO 5 (synthetic promoter)
agtttattcttgacatgtagtgaggggggctggtataat SEQ ID: NO 6 (Ldc2 S111C protein sequence)
MYKDLKFPVLIVHRDIKADTVAGERVRGIAHELEQDGFSILSTASSAEGRIVASTHHGLACILVAA
EGAGENCRLLQDVVELIRVARVRAPQLPIFALGEQVTIENAPAECMADLHQLRGILYLFEDTVPF
LARQVARAARNYLAGLLPPFFRALVEHTAQSNYSWHTPGHGGGVAYRKSPVGQAFHQFFGE
NTLRSDLSVSVPELGSLLDHTGPLAEAEDRAARNFGADHTFFVINGTSTANKIVWHSMVGRED
LVLVDRNCHKSILHSIIMTGAIPLYLTPERNELGIIGPIPLSEFSKQSIAAKIAASPLARGREPKVKL
AVVTNSTYDGLCYNAELIKQTLGDSVEVLHFDEAWYAYAAFHEFYDGRYGMGTSRSEEGPLVF
ATHSTHKMLAAFSQASMIHVQDGGTRKLDVARFNEAFMMHSTSPQYGIIASLDVASAMMEGP
AGRSLIQETFDEALSFRRALANVRQNLDRNDWWFGVWQPEQVEGTDQVGTHDWVLEPSAD
WHGFGDIAEDYVLLDPIKVTLTTPGLSAGGKLSEQGIPAAIVSRFLWERGLVVEKTGLYSFLVLF
SMGITKGKWSTLVTELLEFKRCYDANLPLLDVLPSVAQAGGKRYNGVGLRDLSDAMHASYRD
NATAKAMKRMYTVLPEVAMRPSEAYDKLVRGEVEAVPIARLEGRIAAVMLVPYPPGIPLIMPGE
RFTEATRSILDYLEFARTFERAFPGFDSDVHGLQHQDGPSGRCYTVECIKE SEQ ID NO: 7 (aat DNA sequence)
>gb|AY271828.1|: 385-1717 H. alvei plasmid pAlvA, complete sequence
    1 ttgactttgt taaaagtcag gcataagatc aaaatactgt atatataaca atgtatttat
   61 atacagtatt ttatactttt tatctaacgt cagagagggc aatattatga gtggtggaga
  121 tggcaagggt cacaatagtg gagcacatga ttccggtggc agcattaatg gaacttctgg
  181 gaaaggtggg ccatcaagcg gaggagcatc agataattct gggtggagtt cggaaaataa
  241 cccgtggggc ggtggtaact cgggagtgat tggtggcagt caaggaggta acggagctaa
  301 tcatggtggc gaaaatacat cttctaacta tgggaaagat gtatcacgcc aaatcggtga
  361 tgcgatagcc agaaaggaag gcatcaatcc gaaaatattc actgggtact ttatccgttc
  421 agatggatat ttgatcggaa taacgccact tgtcagtggt gatgcctttg gcgttaatct
  481 tggcctgttc aataacaat aaaatagtag tagtgaaaat aagggatgga atggaaggaa
  541 tggagatggc attaaaaata gtagccaagg tggatggaag attaaaacta atgaacttac
  601 ttcaaaccaa gtagctgctg ctaaatccgt tccagaacct aaaaaatagta aatattataa
  661 gtccatgaga gaagctagcg atgaggttat taattctaat ttaaaccaag ggcatggagt
  721 tggtgaggca gctagagctg aaagagatta cagagaaaaa gtaaagaacg caatcaatga
  781 taatagtccc aatgtgctac aggatgctat taaatttaca gcagatttt ataaggaagt
  841 ttttaacgct tacggagaaa aagccgaaaa actagccaag ttattagctg atcaagctaa
  901 aggtaaaaag atccgcaatg tagaaatgac attgaaatct tatgaaaaac acaaggctaa
  961 cattaacaaa aaaatcaatg cgaaagatcg cgaagctatc gccaaggctt tggagtctat
 1021 ggatgtagaa aaagccgcaa aaatatatc caagttcagc aaaggactag gttgggttgg
 1081 cccagctatc gatataactg attggttttac agaattatac aaagcagtga aaactgataa
 1141 ttggagatct cttttatgtta aaactgaaac tattgcagta gggctagctg caacccatgt
 1201 caccgcctta gcattcagtg ctgtcttggg tgggcctata ggtattttag gttatggttt
 1261 gattatggct ggggttgggg cgttagttaa cgagacaata gttgacgagg caaataaggt
 1321 cattgggatt taa
```

-continued

SEQUENCE LISTINGS

SEQ ID NO: 8 (aai DNA sequence)
>gb|AY271828.1|: 1734-2069 H. alvei plasmid pAlvA, complete sequence
```
   1 ctatatttta gcggtcacat tttttatttc aaaacaaaca gaaagaacac caataggaat
  61 tgatgtcata aaaataaaaa taaaatacaa agtcattaaa tatgttttg gcacaccatc
 121 cttaaaaaaa cctgttttcc aaaattcttt tttcgtatat ctaagcgctg ctttctctat
 181 tagaaaccga gagaaggaa atagaatagc gctagccaaa ccaaagattc tgagcgcaat
 241 tattttaggt tcgtcatcac cataactggc gtaaagaata caagcagcca taagtatcc
 301 ccaaaacata ttatgtatgt aatatttcct tgtcat
```

SEQ ID NO: 9 (abt DNA sequence)
>gb|AY271829.1|: 384-1566 H. alvei plasmid pAlvB, complete sequence
```
   1 atgagtggtg gagacggtaa aggtcacaat agtggagcac atgattccgg tggcagcatt
  61 aatggaactt cggggaaagg tggacctgat tctggtggcg gatattggga caaccatcca
 121 catattacaa tcaccggtgg acgggaagta ggtcaagggg gagctggtat caactgggt
 181 ggtggttctg tcatggtaa cggcggggc tcagttgcca tccaagaata taacacgagt
 241 aaatatccta acacgggagg atttcctcct cttggacaag ctagctggct gttaaatcct
 301 ccaaaatggt cggttattga agtaaaatca gaaaactcag catggcgctc ttatattact
 361 catgttcaag tcatgttta caattgact tttgatggta cgggtaagct cattgatacc
 421 gcgtatgtta attatgaacc cagtgatgat actcgttgga gcccgcttaa agttttaaa
 481 tataataaag gaaccgctga aaaacaggtt agggatgccgt ttaacaatga aaaagaagca
 541 gttaaggacg ctgttaaatt tactgcagac ttctataaag aggttttaa ggtttacgga
 601 gaaaagccg agaagctcgc taagttatta gcagatcaag ctaaaggcaa aaaggttcgc
 661 aacgtagaag atgccttgaa atcttatgaa aaatataaga ctaacattaa caaaaaaatc
 721 aatgcgaaag atcgcaagc tattgctaaa gccttggagt ctatggatgt aggaaagcc
 781 gcaaaaaata tagccaagtt cagtaaagga ctaggttggg ttggccctgc tatcgatata
 841 actgattggt ttacagaatt ataccaagca gtggaaactg ataattggag atcttttat
 901 gttaaaactg aaactattgc agtagggcta gctgcaaccc atgttgccgc cttggcattc
 961 agcgctgtct gggtgggcc tgtaggtatt ttggttatg gtttgattat ggctggggtt
1021 ggggcgttag ttaatgagac aatagttgac gaggcaaata aggttattgg gctttaa
```

SEQ ID NO: 10 (abi DNA sequence)
>gb|AY271829.1|: 1583-1918 H. alvei plasmid pAlvB, complete sequence
```
   1 ctataattta gcggtcacat tttttatttc aaaaaaaaca gaaataacac ctataggaat
  61 tgatgtcata aaaataaaaa ttaaatacaa agtcattaaa tatgttttg gcacgccatc
 121 cttaaaaaaa ccagtttccc aaaattcttt tttcgtatat ctaagcgcgg ttttctctat
 181 taaaaaccga gagaagggga ataggatagc actagccaaa ccaaagattc tgagcgcaat
 241 tattttaggt tcgttatccc cataactggc gtaaagaata caaacagcca taagtaccc
 301 ccaaaacata ttatgtatat aatatttcct tgtcat
```

SEQ ID: NO 11 (Ldc2 N262T protein sequence)
MYKDLKFPVLIVHRDIKADTVAGERVRGIAHELEQDGFSILSTASSAEGRIVASTHHGLACILVAA
EGAGENQRLLQDVVELIRVARVRAPQLPIFALGEQVTIENAPAESMADLHQLRGILYLFEDTVPF
LARQVARAARNYLAGLLPPFFRALVEHTAQSNYSWHTPGHGGGVAYRKSPVGQAFHQFFGE
NTLRSDLSVSVPELGSLLDHTGPLAEAEDRAARNFGADHTFFVINGTSTANKIVWHSMVGRED
LVLVDRTCHKSILHSIIMTGAIPLYLTPERNELGIIGPIPLSEFSKQSIAAKIAASPLARGREPKVKLA
VVTNSTYDGLCYNAELIKQTLGDSVEVLHFDEAWYAYAAFHEFYDGRYGMGTSRSEEGPLVFA
THSTHKMLAAFSQASMIHVQDGGTRKLDVARFNEAFMMHISTSPQYGIIASLDVASAMMEGPA
GRSLIQETFDEALSFRRALANVRQNLDRNDWWFGVWQPEQVEGTDQVGTHDWVLEPSADW
HGFGDIAEDYVLLDPIKVTLTTPGLSAGGKLSEQGIPAAIVSRFLWERGLVVEKTGLYSFLVLFS
MGITKGKWSTLVTELLEFKRCYDANLPLLDVLPSVAQAGGKRYNGVGLRDLSDAMHASYRDN
ATAKAMKRMYTVLPEVAMRPSEAYDKLVRGEVEAVPIARLEGRIAAVMLVPYPPGIPLIMPGER
FTEATRSILDYLEFARTFERAFPGFDSDVHGLQHQDGPSGRCYTVECIKE SEQ ID: NO 12 (Ldc2 K265N protein sequence)
MYKDLKFPVLIVHRDIKADTVAGERVRGIAHELEQDGFSILSTASSAEGRIVASTHHGLACILVAA
EGAGENQRLLQDVVELIRVARVRAPQLPIFALGEQVTIENAPAESMADLHQLRGILYLFEDTVPF
LARQVARAARNYLAGLLPPFFRALVEHTAQSNYSWHTPGHGGGVAYRKSPVGQAFHQFFGE
NTLRSDLSVSVPELGSLLDHTGPLAEAEDRAARNFGADHTFFVINGTSTANKIVWHSMVGRED
LVLVDRNCHNSILHSIIMTGAIPLYLTPERNELGIIGPIPLSEFSKQSIAAKIAASPLARGREPKVKL
AVVTNSTYDGLCYNAELIKQTLGDSVEVLHFDEAWYAYAAFHEFYDGRYGMGTSRSEEGPLVF
ATHSTHKMLAAFSQASMIHVQDGGTRKLDVARFNEAFMMHISTSPQYGIIASLDVASAMMEGP
AGRSLIQETFDEALSFRRALANVRQNLDRNDWWFGVWQPEQVEGTDQVGTHDWVLEPSAD
WHGFGDIAEDYVLLDPIKVTLTTPGLSAGGKLSEQGIPAAIVSRFLWERGLVVEKTGLYSFLVLF
SMGITKGKWSTLVTELLEFKRCYDANLPLLDVLPSVAQAGGKRYNGVGLRDLSDAMHASYRD
NATAKAMKRMYTVLPEVAMRPSEAYDKLVRGEVEAVPIARLEGRIAAVMLVPYPPGIPLIMPGE
RFTEATRSILDYLEFARTFERAFPGFDSDVHGLQHQDGPSGRCYTVECIKE SEQ ID: NO 13 (Ldc2 S111C/N262T protein sequence)
MYKDLKFPVLIVHRDIKADTVAGERVRGIAHELEQDGFSILSTASSAEGRIVASTHHGLACILVAA
EGAGENQRLLQDVVELIRVARVRAPQLPIFALGEQVTIENAPAECMADLHQLRGILYLFEDTVPF
LARQVARAARNYLAGLLPPFFRALVEHTAQSNYSWHTPGHGGGVAYRKSPVGQAFHQFFGE
NTLRSDLSVSVPELGSLLDHTGPLAEAEDRAARNFGADHTFFVINGTSTANKIVWHSMVGRED
LVLVDRTCHKSILHSIIMTGAIPLYLTPERNELGIIGPIPLSEFSKQSIAAKIAASPLARGREPKVKLA
VVTNSTYDGLCYNAELIKQTLGDSVEVLHFDEAWYAYAAFHEFYDGRYGMGTSRSEEGPLVFA
THSTHKMLAAFSQASMIHVQDGGTRKLDVARFNEAFMMHISTSPQYGIIASLDVASAMMEGPA
GRSLIQETFDEALSFRRALANVRQNLDRNDWWFGVWQPEQVEGTDQVGTHDWVLEPSADW
HGFGDIAEDYVLLDPIKVTLTTPGLSAGGKLSEQGIPAAIVSRFLWERGLVVEKTGLYSFLVLFS

```
MGITKGKWSTLVTELLEFKRCYDANLPLLDVLPSVAQAGGKRYNGVLRDLSDAMHASYRDN
ATAKAMKRMYTVLPEVAMRPSEAYDKLVRGEVEAVPIARLEGRIAAVMLVPYPPGIPLIMPGER
FTEATRSILDYLEFARTFERAFPGFDSDVHGLQHQDGPSGRCYTVECIKE

SEQ ID: NO 14 (Ldc2 S111C/K265N protein sequence)
MYKDLKFPVLIVHRDIKADTVAGERVRGIAHELEQDGFSILSTASSAEGRIVASTHHGLACILVAA
EGAGENQRLLQDVVELIRVARVRAPQLPIFALGEQVTIENAPAECMADLHQLRGILYLFEDTVPF
LARQVARAARNYLAGLLPPFFRALVEHTAQSNYSWHTPGHGGGVAYRKSPVGQAFHQFFGE
NTLRSDLSVSVPELGSLLDHTGPLAEAEDRAARNFGADHTFFVINGTSTANKIVWHSMVGRED
LVLVDRNCHNSILHSIIMTGAIPLYLTPERNELGIIGPIPLSEFSKQSIAAKIAASPLARGREPKVKL
AVVTNSTYDGLCYNAELIKQTLGDSVEVLHFDEAWYAYAAFHEFYDGRYGMGTSRSEEGPLVF
ATHSTHKMLAAFSQASMIHVQDGGTRKLDVARFNEAFMMHISTSPQYGIIASLDVASAMMEGP
AGRSLIQETFDEALSFRRALANVRQNLDRNDWWFGVWQPEQVEGTDQVGTHDWVLEPSAD
WHGFGDIAEDYVLLDPIKVTLTTPGLSAGGKLSEQGIPAAIVSRFLWERGLVVEKTGLYSFLVLF
SMGITKGKWSTLVTELLEFKRCYDANLPLLDVLPSVAQAGGKRYNGVLRDLSDAMHASYRD
NATAKAMKRMYTVLPEVAMRPSEAYDKLVRGEVEAVPIARLEGRIAAVMLVPYPPGIPLIMPGE
RFTEATRSILDYLEFARTFERAFPGFDSDVHGLQHQDGPSGRCYTVECIKE SEQ ID: NO 15 (Ldc2 N262T/K265N protein sequence)
MYKDLKFPVLIVHRDIKADTVAGERVRGIAHELEQDGFSILSTASSAEGRIVASTHHGLACILVAA
EGAGENQRLLQDVVELIRVARVRAPQLPIFALGEQVTIENAPAESMADLHQLRGILYLFEDTVPF
LARQVARAARNYLAGLLPPFFRALVEHTAQSNYSWHTPGHGGGVAYRKSPVGQAFHQFFGE
NTLRSDLSVSVPELGSLLDHTGPLAEAEDRAARNFGADHTFFVINGTSTANKIVWHSMVGRED
LVLVDRTCHNSILHSIIMTGAIPLYLTPERNELGIIGPIPLSEFSKQSIAAKIAASPLARGREPKVKL
AVVTNSTYDGLCYNAELIKQTLGDSVEVLHFDEAWYAYAAFHEFYDGRYGMGTSRSEEGPLVF
ATHSTHKMLAAFSQASMIHVQDGGTRKLDVARFNEAFMMHISTSPQYGIIASLDVASAMMEGP
AGRSLIQETFDEALSFRRALANVRQNLDRNDWWFGVWQPEQVEGTDQVGTHDWVLEPSAD
WHGFGDIAEDYVLLDPIKVTLTTPGLSAGGKLSEQGIPAAIVSRFLWEKTGLYSFLVLF
SMGITKGKWSTLVTELLEFKRCYDANLPLLDVLPSVAQAGGKRYNGVLRDLSDAMHASYRD
NATAKAMKRMYTVLPEVAMRPSEAYDKLVRGEVEAVPIARLEGRIAAVMLVPYPPGIPLIMPGE
RFTEATRSILDYLEFARTFERAFPGFDSDVHGLQHQDGPSGRCYTVECIKE SEQ ID: NO 16 (Ldc2 S111C/N262T/K265N protein sequence)
MYKDLKFPVLIVHRDIKADTVAGERVRGIAHELEQDGFSILSTASSAEGRIVASTHHGLACILVAA
EGAGENQRLLQDVVELIRVARVRAPQLPIFALGEQVTIENAPAECMADLHQLRGILYLFEDTVPF
LARQVARAARNYLAGLLPPFFRALVEHTAQSNYSWHTPGHGGGVAYRKSPVGQAFHQFFGE
NTLRSDLSVSVPELGSLLDHTGPLAEAEDRAARNFGADHTFFVINGTSTANKIVWHSMVGRED
LVLVDRTCHNSILHSIIMTGAIPLYLTPERNELGIIGPIPLSEFSKQSIAAKIAASPLARGREPKVKL
AVVTNSTYDGLCYNAELIKQTLGDSVEVLHFDEAWYAYAAFHEFYDGRYGMGTSRSEEGPLVF
ATHSTHKMLAAFSQASMIHVQDGGTRKLDVARFNEAFMMHISTSPQYGIIASLDVASAMMEGP
AGRSLIQETFDEALSFRRALANVRQNLDRNDWWFGVWQPEQVEGTDQVGTHDWVLEPSAD
WHGFGDIAEDYVLLDPIKVTLTTPGLSAGGKLSEQGIPAAIVSRFLWERGLVVEKTGLYSFLVLF
SMGITKGKWSTLVTELLEFKRCYDANLPLLDVLPSVAQAGGKRYNGVLRDLSDAMHASYRD
NATAKAMKRMYTVLPEVAMRPSEAYDKLVRGEVEAVPIARLEGRIAAVMLVPYPPGIPLIMPGE
RFTEATRSILDYLEFARTFERAFPGFDSDVHGLQHQDGPSGRCYTVECIKE SEQ ID: NO 17 (ldc2-co1 DNA sequence)
ATGTACAAAGATCTGAAATTCCCTGTTCTGATTGTACACCGCGATATCAAGGCGGACACGG
TAGCCGGCGAGCGTGTTCGCGGTATTGCCCACGAACTCGAACAAGACGGCTTTAGCATTC
TCTCTACGGCGTCTTCTGCGGAAGGCCGCATTGTGGCTAGCACGCACCACGGTCTCGCCT
GCATCCTCGTGGCAGCTGAGGGTGCGGGTGAGAATCAGCGTCTGCTCCAAGACGTGGTT
GAGCTGATCCGTGTAGCTCGCGTCCGTGCGCCACAGCTCCCGATCTTCGCGCTGGGCGA
ACAGGTGACTATTGAAAACGCGCCTGCCGAATCTATGGCCGACCTGCACCAGCTCCGCGG
CATTCTGTATCTCTTCGAGGATACTGTCCCCGTTCCTGGCACGTCAGGTTGCACGCGCAGC
GCGTAACTACCTCGCTGGCCTCCTCCCGCCATTCTTCCGTGCACTCGTGGAGCACACGGC
CCAAAGCAATTACTCTTGGCACACCCCGGGTCACGGTGGTGGTGTCGCTTACCGTAAATCT
CCGGTAGGTCAAGCTTTCCACCAGTTCTTTGGCGAGAATACCCTCCGGCTCTGACCTGTCTG
TTAGCGTTCCAGAGCTGGGCAGCCTGCTGGATCACACTGGCCCTCTCGCGGAAGCAGAG
GATCGTGCCGCTCGCAATTTCGGTGCGGACCACACCTTCTTTGTCATCAATGGTACCTCTA
CTGCGAACAAAATCGTTTGGCACTCTATGGTTGGTCGCGAGGACCTGGTGCTGGTCGATC
GTAACTGTCACAAATCTATTCTGCACTCCATTATCATGACGGGTGCTATCCCACTGTACCTG
ACTCCGGAACGCAACGAACTGGGTATTATCGGCCCTATTCCACTCTCCGAGTTTTCTAAAC
AATCTATCGCAGCAAAATTGCCGCCTCCCCACTCGCGCGTGGTCGTGAACCGAAAGTTAA
ACTGGCTGTCGTTACCAACTCTACCTATGACGGTCTGTGTTACAACGCGGAACTGATCAAA
CAAACCCTCGGCGACTCTGTCGAGGTACTGCATTTCGACGAGGCTTGGTATGCTTATGCG
GCGTTTCACGAGTTCTACGACGGCCGCTACGGTATGGGCACTTCTCGTTCCGAAGAGGGT
CCGCTGGTCTTTGCTACCCATTCTACCCACAAGATGCTCGCGGCTTTTTCCCAAGCTAGCA
TGATTCACGTTCAGGATGGTGGTACGCGCAAGCTGGACGTCGCCCGCTTTAACGAAGCCT
TTATGATGCACATCAGCACCTCTCCACAGTACGGCATCATTGCGTCTCTCGATGTCGCAAG
CGCTATGATGGAAGGTCCTGCCGGTCGTAGCCTGATCCAAGAGACGTTCGATGAGGCGCT
GTCCTTCCGTCGTGCTCTGGCGAATGTCCGTCAGAACCTGGACCGTAATGATTGGTGGTT
CGGTGTCTGGCAACCGGAGCAGGTTGAGGGCACCGACCAGGTAGGTACTCACGACTGGG
TTCTCGAGCCTAGCGCGGACTGGCATGGTTTGGTGACATTGCGGAGGATTACGTTCTCCT
CGATCCTATCAAGTTACCCTGACCACCCCAGGTCTGAGCGCTGGCGGTAAACTCTCTGAA
CAAGGCATCCCGGCAGCTATCGTTAGCCGTTTCCTGTGGGAACGTGGTCTGGTGGTCGAG
AAAACGGGTCTGTACTCTTTCCTGGTTCTGTTCTCCATGGGTATCACGAAAGGCAAATGGT
CTACTCTGGTTACCGAGCTGCTCGAATTCAAACGCTGTTACGACGCGAATCTGCCACTCCT
```

```
GGATGTGCTGCCTTCTGTAGCGCAGGCGGGTGGTAAACGCTATAACGGTGTAGGTCTGCG
TGATCTGTCCGATGCCATGCACGCTTCTTATCGTGACAATGCCACGGCGAAGGCCATGAA
GCGTATGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCGGCGGT
TATGCTGGTTCCGTACCCGCCAGGTATCCCGCTCATTATGCCGGGTGAACGTTTTACTGAA
GCTACCCGCTCCATTCTGGACTATCTGGAGTTTGCCCGTACCTTCGAGCGCGCGTTCCCG
GGCTTTGACTCTGATGTTCACGGCCTCCAACATCAAGATGGCCCGTCTGGCCGTTGTTATA
CCGTTGAATGCATCAAGGAATAA

SEQ ID: NO 18 (Idc2-co1 C332G DNA sequence)
ATGTACAAAGATCTGAAATTCCCTGTTCTGATTGTACACCGCGATATCAAGGCGGACACGG
TAGCCGGCGAGCGTGTTCGCGGTATTGCCCACGAACTCGAACAAGACGGCTTTAGCATTC
TCTCTACGGCGTCTTCTGCGGAAGGCCGCATTGTGGCTAGCACGCACCACGGTCTCGCCT
GCATCCTCGTGGCAGCTGAGGGTGCGGGTGAGAATCAGCGTCTGCTCCAAGACGTGGTT
GAGCTGATCCGTGTAGCTCGCGTCCGTGCGCCACAGCTCCCGATCTTCGCGCTGGGCGA
ACAGGTGACTATTGAAAACGCGCCTGCCGAATGTATGGCCGACCTGCACCAGCTCCGCGG
CATTCTGTATCTCTTCGAGGATACTGTCCCGTTCCTGGCACGTCAGGTTGCACGCGCAGC
GCGTAACTACCTCGCTGGCCTCCTCCCGCCATTCTTCCGTGCACTCGTGGAGCACACGGC
CCAAAGCAATTACTCTTGGCACACCCCGGGTCACGGTGGTGGTGTCGCTTACCGTAAATCT
CCGGTAGGTCAAGCTTTCCACCAGTTCTTTGGCGAGAATACCCTCCGCTCTGACCTGTCTG
TTAGCGTTCCAGAGCTGGGCAGCCTGCTGGATCACACTGGCCCTCTCGCGGAAGCAGAG
GATCGTGCCGCTCGCAATTTCGGTGCGGACCACACCTTCTTTGTCATCAATGGTACCTCTA
CTGCGAACAAAATCGTTTGGCACTCTATGGTTGGTCGCGAGGACCTGGTGCTGGTCGATC
GTAACTGTCACAAATCTATTCTGCACTCCATTATCATGACGGGTGCTATCCCACTGTACCTG
ACTCCGGAACGCAACGAACTGGGTATTATCGGCCCTATTCCACTCTCCGAGTTTTCTAAAC
AATCTATCGCAGCAAAAATTGCCGCCTCCCCACTCGCGCGTGGTCGTGAACCGAAAGTTAA
ACTGGCTGTCGTTACCAACTCTACCTATGACGGTCTGTGTTACAACGCGAACTGATCAAA
CAAACCCTCGGCGACTCTGTCGAGGTACTGCATTTCGACGAGGCTTGGTATGCTTATGCG
GCGTTTCACGAGTTCTACGACGGCCGCTACGGTATGGGCACTTCTCGTTCCGAAGAGGGT
CCGCTGGTCTTTGCTACCCATTCTACCCACAAGATGCTCGCGGCTTTTTCCCAAGCTAGCA
TGATTCACGTTCAGGATGGTGGTACGCGCAAGCTGGACGTCGCCCGCTTTAACGAAGCCT
TTATGATGCACATCAGCACCTCTCCACAGTACGGCATCATTGCGTCTCTCGATGTCGCAAG
CGCTATGATGGAAGGTCCTGCCGGTCGTAGCCTGATCCAAGAGACGTTCGATGAGGCGCT
GTCCTTCCGTCGTGCTCTGGCGAATGTCCGTCAGAACCTGGACCGTAATGATTGGTGGTT
CGGTGTCTGGCAACCGGAGCAGGTTGAGGGCACCGACCAGGTAGGTACTCACGACTGGG
TTCTCGAGCCTAGCGCGGACTGGCATGGTTTTGGTGACATTGCGGAGGATTACGTTCTCCT
CGATCCTATCAAAGTTACCCTGACCACCCCAGGTCTGAGCGCTGGCGGTAAACTCTCTGAA
CAAGGCATCCCGGCAGCTATCGTTAGCCGTTTCCTGTGGGAACGTGGTCTGGTGGTCGAG
AAAACGGGTCTGTACTCTTTCCTGGTTCTGTTCTCCATGGGTATCACGAAAGGCAAATGGT
CTACTCTGGTTACCGAGCTGCTCGAATTCAAACGCTGTTACGACGCGAATCTGCCACTCCT
GGATGTGCTGCCTTCTGTAGCGCAGGCGGGTGGTAAACGCTATAACGGTGTAGGTCTGCG
TGATCTGTCCGATGCCATGCACGCTTCTTATCGTGACAATGCCACGGCGAAGGCCATGAA
GCGTATGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCGGCGGT
TATGCTGGTTCCGTACCCGCCAGGTATCCCGCTCATTATGCCGGGTGAACGTTTTACTGAA
GCTACCCGCTCCATTCTGGACTATCTGGAGTTTGCCCGTACCTTCGAGCGCGCGTTCCCG
GGCTTTGACTCTGATGTTCACGGCCTCCAACATCAAGATGGCCCGTCTGGCCGTTGTTATA
CCGTTGAATGCATCAAGGAATAA SEQ ID: NO 19 (Idc2-co1A785C DNA sequence)
ATGTACAAAGATCTGAAATTCCCTGTTCTGATTGTACACCGCGATATCAAGGCGGACACGG
TAGCCGGCGAGCGTGTTCGCGGTATTGCCCACGAACTCGAACAAGACGGCTTTAGCATTC
TCTCTACGGCGTCTTCTGCGGAAGGCCGCATTGTGGCTAGCACGCACCACGGTCTCGCCT
GCATCCTCGTGGCAGCTGAGGGTGCGGGTGAGAATCAGCGTCTGCTCCAAGACGTGGTT
GAGCTGATCCGTGTAGCTCGCGTCCGTGCGCCACAGCTCCCGATCTTCGCGCTGGGCGA
ACAGGTGACTATTGAAAACGCGCCTGCCGAATCTATGGCCGACCTGCACCAGCTCCGCGG
CATTCTGTATCTCTTCGAGGATACTGTCCCGTTCCTGGCACGTCAGGTTGCACGCGCAGC
GCGTAACTACCTCGCTGGCCTCCTCCCGCCATTCTTCCGTGCACTCGTGGAGCACACGGC
CCAAAGCAATTACTCTTGGCACACCCCGGGTCACGGTGGTGGTGTCGCTTACCGTAAATCT
CCGGTAGGTCAAGCTTTCCACCAGTTCTTTGGCGAGAATACCCTCCGCTCTGACCTGTCTG
TTAGCGTTCCAGAGCTGGGCAGCCTGCTGGATCACACTGGCCCTCTCGCGGAAGCAGAG
GATCGTGCCGCTCGCAATTTCGGTGCGGACCACACCTTCTTTGTCATCAATGGTACCTCTA
CTGCGAACAAAATCGTTTGGCACTCTATGGTTGGTCGCGAGGACCTGGTGCTGGTCGATC
GTAACCGTCACAAATCTATTCTGCACTCCATTATCATGACGGGTGCTATCCCACTGTACCTG
ACTCCGGAACGCAACGAACTGGGTATTATCGGCCCTATTCCACTCTCCGAGTTTTCTAAAC
AATCTATCGCAGCAAAAATTGCCGCCTCCCCACTCGCGCGTGGTCGTGAACCGAAAGTTAA
ACTGGCTGTCGTTACCAACTCTACCTATGACGGTCTGTGTTACAACGCGGAACTGATCAAA
CAAACCCTCGGCGACTCTGTCGAGGTACTGCATTTCGACGAGGCTTGGTATGCTTATGCG
GCGTTTCACGAGTTCTACGACGGCCGCTACGGTATGGGCACTTCTCGTTCCGAAGAGGGT
CCGCTGGTCTTTGCTACCCATTCTACCCACAAGATGCTCGCGGCTTTTTCCCAAGCTAGCA
TGATTCACGTTCAGGATGGTGGTACGCGCAAGCTGGACGTCGCCCGCTTTAACGAAGCCT
TTATGATGCACATCAGCACCTCTCCACAGTACGGCATCATTGCGTCTCTCGATGTCGCAAG
CGCTATGATGGAAGGTCCTGCCGGTCGTAGCCTGATCCAAGAGACGTTCGATGAGGCGCT
GTCCTTCCGTCGTGCTCTGGCGAATGTCCGTCAGAACCTGGACCGTAATGATTGGTGGTT
CGGTGTCTGGCAACCGGAGCAGGTTGAGGGCACCGACCAGGTAGGTACTCACGACTGGG
TTCTCGAGCCTAGCGCGGACTGGCATGGTTTTGGTGACATTGCGGAGGATTACGTTCTCCT
CGATCCTATCAAAGTTACCCTGACCACCCCAGGTCTGAGCGCTGGCGGTAAACTCTCTGAA
```

```
CAAGGCATCCCGGCAGCTATCGTTAGCCGTTTCCTGTGGGAACGTGGTCTGGTGGTCGAG
AAAACGGGTCTGTACTCTTTCCTGGTTCTGTTCTCCATGGGTATCACGAAAGGCAAATGGT
CTACTCTGGTTACCGAGCTGCTCGAATTCAAACGCTGTTACGACGCGAATCTGCCACTCCT
GGATGTGCTGCCTTCTGTAGCGCAGGCGGGTGGTAAACGCTATAACGGTGTAGGTCTGCG
TGATCTGTCCGATGCCATGCACGCTTCTTATCGTGACAATGCCACGGCGAAGGCCATGAA
GCGTATGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCGGCGGT
TATGCTGGTTCCGTACCCGCCAGGTATCCCGCTCATTATGCCGGGTGAACGTTTTACTGAA
GCTACCCGCTCCATTCTGGACTATCTGGAGTTTGCCCGTACCTTCGAGCGCGCGTTCCCG
GGCTTTGACTCTGATGTTCACGGCCTCCAACATCAAGATGGCCCGTCTGGCCGTTGTTATA
CCGTTGAATGCATCAAGGAATAA

SEQ ID: NO 20 (Idc2-col A795C DNA sequence)
ATGTACAAAGATCTGAAATTCCCTGTTCTGATTGTACACCGCGATATCAAGGCGGACACGG
TAGCCGGCGAGCGTGTTCGCGGTATTGCCCACGAACTCGAACAAGACGGCTTTAGCATTC
TCTCTACGGCGTCTTCTGCGGAAGGCCGCATTGTGGCTAGCACGCACCACGGTCTCGCCT
GCATCCTCGTGGCAGCTGAGGGTGCGGGTGAGAATCAGCGTCTGCTCCAAGACGTGGTT
GAGCTGATCCGTGTAGCTCGCGTCCGTGCGCCACAGCTCCCGATCTTCGCGCTGGGCGA
ACAGGTGACTATTGAAAACGCGCCTGCCGAATCTATGGCCGACCTGCACCAGCTCCGCGG
CATTCTGTATCTCTTCGAGGATACTGTCCCGTTCCTGGCACGTCAGGTTGCACGCGCAGC
GCGTAACTACCTCGCTGGCCTCCTCCCGCCATTCTTCCGTGCACTCGTGGAGCACACGGC
CCAAAGCAATTACTCTTGGCACACCCCGGGTCACGGTGGTGGTGTCGCTTACCGTAAATCT
CCGGTAGGTCAAGCTTTCCACCAGTTCTTTGGCGAGAATACCCTCCGCTCTGACCTGTCTG
TTAGCGTTCCAGAGCTGGGCAGCCTGCTGGATCACACTGGCCCTCTCGCGGAAGCAGAG
GATCGTGCCGCTCGCAATTTCGGTGCGGACCACACCTTCTTTGTCATCAATGGTACCTCTA
CTGCGAACAAAATCGTTTGGCACTCTATGGTTGGTCGCGAGGACCTGGTGCTGGTCGATC
GTAACTGTCACAACTCTATTCTGCACTCCATTATCATGACGGGTGCTATCCCACTGTACCTG
ACTCCGGAACGCAACGAACTGGGTATTATCGGCCCTATTCCACTCTCCGAGTTTTCTAAAC
AATCTATCGCAGCAAAAATTGCCGCCTCCCCACTCGCGCGTGGTCGTGAACCGAAAGTTAA
ACTGGCTGTCGTTACCAACTCTACCTATGACGGTCTGTGTTACAACGCGGAACTGATCAAA
CAAACCCTCGGCGACTCTGTCGAGGTACTGCATTTCGACGAGGCTTGGTATGCTTATGCG
GCGTTTCACGAGTTCTACGACGGCCGCTACGGTATGGGCACTTTCTCGTTCCGAAGAGGGT
CCGCTGGTCTTTGCTACCCATTCTACCCACAAGATGCTCGCGGCTTTTTCCCAAGCTAGCA
TGATTCACGTTCAGGATGGTGGTACGCGCAAGCTGGACGTCGCCCGCTTTAACGAAGCCT
TTATGATGCACATCAGCACCTCTCCACAGTACGGCATCATTGCGTCTCTCGATGTCGCAAG
CGCTATGATGGAAGGTCCTGCCGGTCGTAGCCTGATCCAAGAGACGTTCGATGAGGCGCT
GTCCTTCCGTCGTGCTCTGGCGAATGTCCGTCAGAACCTGGACCGTAATGATTGGTGGTT
CGGTGTCTGGCAACCGGAGCAGGTTGAGGGCACCGACCAGGTAGGTACTCACGACTGGG
TTCTCGAGCCTAGCGCGGACTGGCATGGTTTTGGTGACATTGCGGAGGATTACGTTCTCCT
CGATCCTATCAAAGTTACCCTGACCACCCCAGGTCTGAGCGCTGGCGGTAAATCTCTGAA
CAAGGCATCCCGGCAGCTATCGTTAGCCGTTTCCTGTGGGAACGTGGTCTGGTGGTCGAG
AAAACGGGTCTGTACTCTTTCCTGGTTCTGTTCTCCATGGGTATCACGAAAGGCAAATGGT
CTACTCTGGTTACCGAGCTGCTCGAATTCAAACGCTGTTACGACGCGAATCTGCCACTCCT
GGATGTGCTGCCTTCTGTAGCGCAGGCGGGTGGTAAACGCTATAACGGTGTAGGTCTGCG
TGATCTGTCCGATGCCATGCACGCTTCTTATCGTGACAATGCCACGGCGAAGGCCATGAA
GCGTATGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCGGCGGT
TATGCTGGTTCCGTACCCGCCAGGTATCCCGCTCATTATGCCGGGTGAACGTTTTACTGAA
GCTACCCGCTCCATTCTGGACTATCTGGAGTTTGCCCGTACCTTCGAGCGCGCGTTCCCG
GGCTTTGACTCTGATGTTCACGGCCTCCAACATCAAGATGGCCCGTCTGGCCGTTGTTATA
CCGTTGAATGCATCAAGGAATAA SEQ ID: NO 21 (Idc2-col C332G/A785C DNA sequence)
ATGTACAAAGATCTGAAATTCCCTGTTCTGATTGTACACCGCGATATCAAGGCGGACACGG
TAGCCGGCGAGCGTGTTCGCGGTATTGCCCACGAACTCGAACAAGACGGCTTTAGCATTC
TCTCTACGGCGTCTTCTGCGGAAGGCCGCATTGTGGCTAGCACGCACCACGGTCTCGCCT
GCATCCTCGTGGCAGCTGAGGGTGCGGGTGAGAATCAGCGTCTGCTCCAAGACGTGGTT
GAGCTGATCCGTGTAGCTCGCGTCCGTGCGCCACAGCTCCCGATCTTCGCGCTGGGCGA
ACAGGTGACTATTGAAAACGCGCCTGCCGAATGTATGGCCGACCTGCACCAGCTCCGCGG
CATTCTGTATCTCTTCGAGGATACTGTCCCGTTCCTGGCACGTCAGGTTGCACGCGCAGC
GCGTAACTACCTCGCTGGCCTCCTCCCGCCATTCTTCCGTGCACTCGTGGAGCACACGGC
CCAAAGCAATTACTCTTGGCACACCCCGGGTCACGGTGGTGGTGTCGCTTACCGTAAATCT
CCGGTAGGTCAAGCTTTCCACCAGTTCTTTGGCGAGAATACCCTCCGCTCTGACCTGTCTG
TTAGCGTTCCAGAGCTGGGCAGCCTGCTGGATCACACTGGCCCTCTCGCGGAAGCAGAG
GATCGTGCCGCTCGCAATTTCGGTGCGGACCACACCTTCTTTGTCATCAATGGTACCTCTA
CTGCGAACAAAATCGTTTGGCACTCTATGGTTGGTCGCGAGGACCTGGTGCTGGTCGATC
GTACCTGTCACAAATCTATTCTGCACTCCATTATCATGACGGGTGCTATCCCACTGTACCTG
ACTCCGGAACGCAACGAACTGGGTATTATCGGCCCTATTCCACTCTCCGAGTTTTCTAAAC
AATCTATCGCAGCAAAAATTGCCGCCTCCCCACTCGCGCGTGGTCGTGAACCGAAAGTTAA
ACTGGCTGTCGTTACCAACTCTACCTATGACGGTCTGTGTTACAACGCGGAACTGATCAAA
CAAACCCTCGGCGACTCTGTCGAGGTACTGCATTTCGACGAGGCTTGGTATGCTTATGCG
GCGTTTCACGAGTTCTACGACGGCCGCTACGGTATGGGCACTTTCTCGTTCCGAAGAGGGT
CCGCTGGTCTTTGCTACCCATTCTACCCACAAGATGCTCGCGGCTTTTTCCCAAGCTAGCA
TGATTCACGTTCAGGATGGTGGTACGCGCAAGCTGGACGTCGCCCGCTTTAACGAAGCCT
TTATGATGCACATCAGCACCTCTCCACAGTACGGCATCATTGCGTCTCTCGATGTCGCAAG
CGCTATGATGGAAGGTCCTGCCGGTCGTAGCCTGATCCAAGAGACGTTCGATGAGGCGCT
GTCCTTCCGTCGTGCTCTGGCGAATGTCCGTCAGAACCTGGACCGTAATGATTGGTGGTT
```

CGGTGTCTGGCAACCGGAGCAGGTTGAGGGCACCGACCAGGTAGGTACTCACGACTGGG
TTCTCGAGCCTAGCGCGGACTGGCATGGTTTTGGTGACATTGCGGAGGATTACGTTCTCCT
CGATCCTATCAAAGTTACCCTGACCACCCCAGGTCTGAGCGCTGGCGGTAAACTCTCTGAA
CAAGGCATCCCGGCAGCTATCGTTAGCCGTTTCCTGTGGGAACGTGGTCTGGTGGTCGAG
AAAACGGGTCTGTACTCTTTCCTGGTTCTGTTCTCCATGGGTATCACGAAAGGCAAATGGT
CTACTCTGGTTACCGAGCTGCTCGAATTCAAACGCTGTTACGACGCGAATCTGCCACTCCT
GGATGTGCTGCCTTCTGTAGCGCAGGCGGGTGGTAAACGCTATAACGGTGTAGGTCTGCG
TGATCTGTCCGATGCCATGCACGCTTCTTATCGTGACAATGCCACGGCGAAGGCCATGAA
GCGTATGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCGGCGGT
TATGCTGGTTCCGTACCCGCCAGGTATCCCGCTCATTATGCCGGGTGAACGTTTTACTGAA
GCTACCCGCTCCATTCTGGACTATCTGGAGTTTGCCCGTACCTTCGAGCGCGCGTTCCCG
GGCTTTGACTCTGATGTTCACGGCCTCCAACATCAAGATGGCCCGTCTGGCCGTTGTTATA
CCGTTGAATGCATCAAGGAATAA

SEQ ID: NO 22 (Idc2-col C332G/A795C DNA sequence)
ATGTACAAAGATCTGAAATTCCCTGTTCTGATTGTACACCGCGATATCAAGGCGGACACGG
TAGCCGGCGAGCGTGTTCGCGGTATTGCCCACGAACTCGAACAAGACGGCTTTAGCATTC
TCTCTACGGCGTCTTCTGCGGAAGGCCGCATTGTGGCTAGCACGCACCACGGTCTCGCCT
GCATCCTCGTGGCAGCTGAGGGTGCGGGTGAGAATCAGCGTCTGCTCCAAGACGTGGTT
GAGCTGATCCGTGTAGCTCGCGTCCGTGCGCCACAGCTCCCGATCTTCGCGCTGGGCGA
ACAGGTGACTATTGAAAACGCGCCTGCCGAATGTATGGCCGACCTGCACCAGCTCCGCGG
CATTCTGTATCTCTTCGAGGATACTGTCCCGTTCCTGGCACGTCAGGTTGCACGCGCAGC
GCGTAACTACCTCGCTGGCCTCCTCCCGCCATTCTTCCGTGCACTCGTGGAGCACACGGC
CCAAAGCAATTACTCTTGGCACACCCCGGGTCACGGTGGTGGTGTCGCTTACCGTAAATCT
CCGGTAGGTCAAGCTTTCCACCAGTTCTTTGGCGAGAATACCCTCCGCTCTGACCTGTCTG
TTAGCGTTCCAGAGCTGGGCAGCCTGCTGGATCACACTGGCCCTCTCGCGGAAGCAGAG
GATCGTGCCGCTCGCAATTTCGGTGCGGACCACACCTTCTTTGTCATCAATGGTACCTCTA
CTGCGAACAAAATCGTTTGGCACTCTATGGTTGGTCGCGAGGACCTGGTGCTGGTCGATC
GTAACTGTCACAACTCTATTCTGCACTCCATTATCATGACGGGTGCTATCCCACTGTACCTG
ACTCCGGAACGCAACGAACTGGGTATTATCGGCCCTATTCCACTCTCCGAGTTTTCTAAAC
AATCTATCGCAGCAAAAATTGCCGCCTCCCACTCGCGTGGTCGTGAACCGAAAGTTAA
ACTGGCTGTCGTTACCAACTCTACCTATGACGGTCTGTGTTACAACGCGGAACTGATCAAA
CAAACCCTCGGCGACTCTGTCGAGGTACTGCATTTCGACGAGGCTTGGTATGCTTATGCG
GCGTTTCACGAGTTCTACGACGGCCGCTACGGTATGGGCACTTCTCGTTCCGAAGAGGGT
CCGCTGGTCTTTGCTACCCATTCTACCCACAAGATGCTCGCGGCTTTTTCCCAAGCTAGCA
TGATTCACGTTCAGGATGGTGGTACGCGCAAGCTGGACGTCGCCCGCTTTAACGAAGCCT
TTATGATGCACATCAGCACCTCTCCACAGTACGGCATCATTGCGTCTCTCGATGTCGCAAG
CGCTATGATGGAAGGTCCTGCCGGTCGTAGCCTGATCCAAGAGACGTTCGATGAGGCGCT
GTCCTTCCGTCGTGCTCTGGCGAATGTCCGTCAGAACCTGGACCGTAATGATTGGTGGTT
CGGTGTCTGGCAACCGGAGCAGGTTGAGGGCACCGACCAGGTAGGTACTCACGACTGGG
TTCTCGAGCCTAGCGCGGACTGGCATGGTTTTGGTGACATTGCGGAGGATTACGTTCTCCT
CGATCCTATCAAAGTTACCCTGACCACCCCAGGTCTGAGCGCTGGCGGTAAACTCTCTGAA
CAAGGCATCCCGGCAGCTATCGTTAGCCGTTTCCTGTGGGAACGTGGTCTGGTGGTCGAG
AAAACGGGTCTGTACTCTTTCCTGGTTCTGTTCTCCATGGGTATCACGAAAGGCAAATGGT
CTACTCTGGTTACCGAGCTGCTCGAATTCAAACGCTGTTACGACGCGAATCTGCCACTCCT
GGATGTGCTGCCTTCTGTAGCGCAGGCGGGTGGTAAACGCTATAACGGTGTAGGTCTGCG
TGATCTGTCCGATGCCATGCACGCTTCTTATCGTGACAATGCCACGGCGAAGGCCATGAA
GCGTATGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCGGCGGT
TATGCTGGTTCCGTACCCGCCAGGTATCCCGCTCATTATGCCGGGTGAACGTTTTACTGAA
GCTACCCGCTCCATTCTGGACTATCTGGAGTTTGCCCGTACCTTCGAGCGCGCGTTCCCG
GGCTTTGACTCTGATGTTCACGGCCTCCAACATCAAGATGGCCCGTCTGGCCGTTGTTATA
CCGTTGAATGCATCAAGGAATAA SEQ ID: NO 23 (Idc2-col A785C/A795C DNA sequence)
ATGTACAAAGATCTGAAATTCCCTGTTCTGATTGTACACCGCGATATCAAGGCGGACACGG
TAGCCGGCGAGCGTGTTCGCGGTATTGCCCACGAACTCGAACAAGACGGCTTTAGCATTC
TCTCTACGGCGTCTTCTGCGGAAGGCCGCATTGTGGCTAGCACGCACCACGGTCTCGCCT
GCATCCTCGTGGCAGCTGAGGGTGCGGGTGAGAATCAGCGTCTGCTCCAAGACGTGGTT
GAGCTGATCCGTGTAGCTCGCGTCCGTGCGCCACAGCTCCCGATCTTCGCGCTGGGCGA
ACAGGTGACTATTGAAAACGCGCCTGCCGAATCTATGGCCGACCTGCACCAGCTCCGCGG
CATTCTGTATCTCTTCGAGGATACTGTCCCGTTCCTGGCACGTCAGGTTGCACGCGCAGC
GCGTAACTACCTCGCTGGCCTCCTCCCGCCATTCTTCCGTGCACTCGTGGAGCACACGGC
CCAAAGCAATTACTCTTGGCACACCCCGGGTCACGGTGGTGGTGTCGCTTACCGTAAATCT
CCGGTAGGTCAAGCTTTCCACCAGTTCTTTGGCGAGAATACCCTCCGCTCTGACCTGTCTG
TTAGCGTTCCAGAGCTGGGCAGCCTGCTGGATCACACTGGCCCTCTCGCGGAAGCAGAG
GATCGTGCCGCTCGCAATTTCGGTGCGGACCACACCTTCTTTGTCATCAATGGTACCTCTA
CTGCGAACAAAATCGTTTGGCACTCTATGGTTGGTCGCGAGGACCTGGTGCTGGTCGATC
GTACCTGTCACAACTCTATTCTGCACTCCATTATCATGACGGGTGCTATCCCACTGTACCTG
ACTCCGGAACGCAACGAACTGGGTATTATCGGCCCTATTCCACTCTCCGAGTTTTCTAAAC
AATCTATCGCAGCAAAAATTGCCGCCTCCCACTCGCGTGGTCGTGAACCGAAAGTTAA
ACTGGCTGTCGTTACCAACTCTACCTATGACGGTCTGTGTTACAACGCGGAACTGATCAAA
CAAACCCTCGGCGACTCTGTCGAGGTACTGCATTTCGACGAGGCTTGGTATGCTTATGCG
GCGTTTCACGAGTTCTACGACGGCCGCTACGGTATGGGCACTTCTCGTTCCGAAGAGGGT
CCGCTGGTCTTTGCTACCCATTCTACCCACAAGATGCTCGCGGCTTTTTCCCAAGCTAGCA
TGATTCACGTTCAGGATGGTGGTACGCGCAAGCTGGACGTCGCCCGCTTTAACGAAGCCT

SEQUENCE LISTINGS

```
TTATGATGCACATCAGCACCTCTCCACAGTACGGCATCATTGCGTCTCTCGATGTCGCAAG
CGCTATGATGGAAGGTCCTGCCGGTCGTAGCCTGATCCAAGAGACGTTCGATGAGGCGCT
GTCCTTCCGTCGTGCTCTGGCGAATGTCCGTCAGAACCTGGACCGTAATGATTGGTGGTT
CGGTGTCTGGCAACCGGAGCAGGTTGAGGGCACCGACCAGGTAGGTACTCACGACTGGG
TTCTCGAGCCTAGCGCGGACTGGCATGGTTTTGGTGACATTGCGGAGGATTACGTTCTCCT
CGATCCTATCAAAGTTACCCTGACCACCCCAGGTCTGAGCGCTGGCGGTAAACTCTCTGAA
CAAGGCATCCCGGCAGCTATCGTTAGCCGTTTCCTGTGGGAACGTGGTCTGGTGGTCGAG
AAAACGGGTCTGTACTCTTTCCTGGTTCTGTTCTCCATGGGTATCACGAAAGGCAAATGGT
CTACTCTGGTTACCGAGCTGCTCGAATTCAAACGCTGTTACGACGCGAATCTGCCACTCCT
GGATGTGCTGCCTTCTGTAGCGCAGGCGGGTGGTAAACGCTATAACGGTGTAGGTCTGCG
TGATCTGTCCGATGCCATGCACGCTTCTTATCGTGACAATGCCACGGCGAAGGCCATGAA
GCGTATGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCGGCGGT
TATGCTGGTTCCGTACCCGCCAGGTATCCCGCTCATTATGCCGGGTGAACGTTTTACTGAA
GCTACCCGCTCCATTCTGGACTATCTGGAGTTTGCCCGTACCTTCGAGCGCGCGTTCCCG
GGCTTTGACTCTGATGTTCACGGCCTCCAACATCAAGATGGCCCGTCTGGCCGTTGTTATA
CCGTTGAATGCATCAAGGAATAA

SEQ ID: NO 24 (Idc2-col C332G/A785C/A795C DNA sequence)
ATGTACAAAGATCTGAAATTCCCTGTTCTGATTGTACACCGCGATATCAAGGCGGACACGG
TAGCCGGCGAGCGTGTTCGCGGTATTGCCCACGAACTCGAACAAGACGGCTTTAGCATTC
TCTCTACGGCGTCTTCTGCGGAAGGCCGCATTGTGGCTAGCACGCACCACGGTCTCGCCT
GCATCCTCGTGGCAGCTGAGGGTGCGGGTGAGAATCAGCGTCTGCTCCAAGACGTGGTT
GAGCTGATCCGTGTAGCTCGCGTCCGTGCGCCACAGCTCCCGATCTTCGCGCTGGGCGA
ACAGGTGACTATTGAAAACGCGCCTGCCGAATGTATGGCCGACCTGCACCAGCTCCGCGG
CATTCTGTATCTCTTCGAGGATACTGTCCCGTTCCTGGCACGTCAGGTTGCACGCGCAGC
GCGTAACTACCTCGCTGGCCTCCTCCCGCCATTCTTCCGTGCACTCGTGGAGCACACGGC
CCAAAGCAATTACTCTTGGCACACCCCGGGTCACGGTGGTGGTGTCGCTTACCGTAAATCT
CCGGTAGGTCAAGCTTTCCACCAGTTCTTTGGCGAGAATACCCTCCGCTCTGACCTGTCTG
TTAGCGTTCCAGAGCTGGGCAGCCTGCTGGATCACACTGGCCCTCTCGCGGAAGCAGAG
GATCGTGCCGCTCGCAATTTCGGTGCGGACCACACCTTCTTTGTCATCAATGGTACCTCTA
CTGCGAACAAAATCGTTTGGCACTCTATGGTTGGTCGCGAGGACCTGGTGCTGGTCGATC
GTACCTGTCACAACTCTATTCTGCACTCCATTATCATGACGGGTGCTATCCCACTGTACCTG
ACTCCGGAACGCAACGAACTGGGTATTATCGGCCCTATTCCACTCTCCGAGTTTTCTAAAC
AATCTATCGCAGCAAAAATTGCCGCCTCCCCACTCGCGCGTGGTCGTGAACCGAAAGTTAA
ACTGGCTGTCGTTACCAACTCTACCTATGACGGTCTGTGTTACAACGCGGAACTGATCAAA
CAAACCCTCGGCGACTCTGTCGAGGTACTGCATTTCGACGAGGCTTGGTATGCTTATGCG
GCGTTTCACGAGTTCTACGACGGCCGCTACGGTATGGGCACTTCTCGTTCCGAAGAGGGT
CCGCTGGTCTTTGCTACCCATTCTACCCACAAGATGCTCGCGGCTTTTTCCCAAGCTAGCA
TGATTCACGTTCAGGATGGTGGTACGCGCAAGCTGGACGTCGCCCGCTTTAACGAAGCCT
TTATGATGCACATCAGCACCTCTCCACAGTACGGCATCATTGCGTCTCTCGATGTCGCAAG
CGCTATGATGGAAGGTCCTGCCGGTCGTAGCCTGATCCAAGAGACGTTCGATGAGGCGCT
GTCCTTCCGTCGTGCTCTGGCGAATGTCCGTCAGAACCTGGACCGTAATGATTGGTGGTT
CGGTGTCTGGCAACCGGAGCAGGTTGAGGGCACCGACCAGGTAGGTACTCACGACTGGG
TTCTCGAGCCTAGCGCGGACTGGCATGGTTTTGGTGACATTGCGGAGGATTACGTTCTCCT
CGATCCTATCAAAGTTACCCTGACCACCCCAGGTCTGAGCGCTGGCGGTAAACTCTCTGAA
CAAGGCATCCCGGCAGCTATCGTTAGCCGTTTCCTGTGGGAACGTGGTCTGGTGGTCGAG
AAAACGGGTCTGTACTCTTTCCTGGTTCTGTTCTCCATGGGTATCACGAAAGGCAAATGGT
CTACTCTGGTTACCGAGCTGCTCGAATTCAAACGCTGTTACGACGCGAATCTGCCACTCCT
GGATGTGCTGCCTTCTGTAGCGCAGGCGGGTGGTAAACGCTATAACGGTGTAGGTCTGCG
TGATCTGTCCGATGCCATGCACGCTTCTTATCGTGACAATGCCACGGCGAAGGCCATGAA
GCGTATGTATACGGTGCTCCCGGAAGTAGCCATGCGCCCGTCCGAAGCTTATGATAAGCT
CGTACGCGGTGAAGTCGAAGCTGTTCCTATTGCACGTCTCGAGGGTCGTATTGCGGCGGT
TATGCTGGTTCCGTACCCGCCAGGTATCCCGCTCATTATGCCGGGTGAACGTTTTACTGAA
GCTACCCGCTCCATTCTGGACTATCTGGAGTTTGCCCGTACCTTCGAGCGCGCGTTCCCG
GGCTTTGACTCTGATGTTCACGGCCTCCAACATCAAGATGGCCCGTCTGGCCGTTGTTATA
CCGTTGAATGCATCAAGGAATAA
```

REFERENCES

The references, patents and published patent applications listed below, and all references cited in the specification above are hereby incorporated by reference in their entirety, as if fully set forth herein.

1. West S E and Iglewski B H (1988). Codon usage in *Pseudomonas aeruginosa*. Nucleic Acids Res 16: 9323-9335.

2. Wertz et al. Chimeric nature of two plasmids of *H. alvei* encoding the bacteriocins alveicins A and B. Journal of Bacteriology, (2004) 186: 1598-1605.

3. Datsenko K A & Wanner B L (2000). One-step inactivation of chromosomal genes in *Escherichia coli* K-12 using PCR products. PNAS: 6640-6645.

4. Papadakis et al., Promoters and Control Elements: Designing Expression Cassettes for Gene Therapy. Current Gene Therapy (2004), 4, 89-113.

What is claimed is:

1. A product, selected from the group consisting of:
   I) a transformant comprising an expression plasmid vector in a host cell that is not a *Pseudomonas aeruginosa* (*P. aeruginosa*) cell, the expression plasmid vector comprising: a polynucleotide encoding one or more polypeptides, each polypeptide consisting of the amino acid sequence of a mutant of SEQ ID NO: 4 (lysine decarboxylase (Ldc2)); and a backbone plasmid capable of autonomous replication in the host cell,
   wherein the mutant of SEQ ID NO:4 (Ldc2) is selected from the group consisting of the amino acid sequences of SEQ ID NO: 6 (Ldc2 S111C), SEQ ID NO: 11 (Ldc2 N262T), SEQ ID NO: 12 (Ldc2 K265N), SEQ ID NO: 13 (Ldc2 S111C/N262T), SEQ ID NO: 14 (Ldc2 S111C/K265N), SEQ ID NO: 15 (Ldc2 N262T/K265N), and SEQ ID NO: 16 (Ldc2 S111C/N262T/K265N);
   II) an expression plasmid vector comprising: a polynucleotide encoding one or more polypeptides, each polypeptide consisting of the amino acid sequence of a mutant of SEQ ID NO: 4 (Ldc2); and a backbone plasmid capable of autonomous replication in a host cell, wherein the host cell is not a *P. aeruginosa* cell,
   wherein the mutant of SEQ ID NO:4 (Ldc2) is selected from the group consisting of the amino acid sequences of SEQ ID NO: 6 (Ldc2 S111C), SEQ ID NO: 11 (Ldc2 N262T), SEQ ID NO: 12 (Ldc2 K265N), SEQ ID NO: 13 (Ldc2 S111C/N262T), SEQ ID NO: 14 (Ldc2 S111C/K265N), SEQ ID NO: 15 (Ldc2 N262T/K265N), and SEQ ID NO: 16 (Ldc2 S111C/N262T/K265N);
   III) a first mutant host cell comprising a polynucleotide integrated into a chromosome of the host cell, wherein the polynucleotide encodes one or more polypeptides, each polypeptide consisting of the amino acid sequence of a mutant of SEQ ID NO: 4 (Ldc2),
   wherein the mutant of SEQ ID NO:4 (Ldc2) is selected from the group consisting of the amino acid sequences of SEQ ID NO: 6 (Ldc2 S111C), SEQ ID NO: 11 (Ldc2 N262T), SEQ ID NO: 12 (Ldc2 K265N), SEQ ID NO: 13 (Ldc2 S111C/N262T), SEQ ID NO: 14 (Ldc2 S111C/K265N), SEQ ID NO: 15 (Ldc2 N262T/K265N), and SEQ ID NO: 16 (Ldc2 S111C/N262T/K265N);
   IV) a non-naturally occurring polynucleotide encoding a polypeptide consisting of the amino acid sequence of a mutant of SEQ ID NO: 4, wherein the mutant of SEQ ID NO: 4 is selected from the group consisting of the amino acid sequences of SEQ ID NO: 6 (Ldc2 S111C), SEQ ID NO: 11 (Ldc2 N262T), SEQ ID NO: 12 (Ldc2 K265N), SEQ ID NO: 13 (Ldc2 S111C/N262T), SEQ ID NO: 14 (Ldc2 S111C/K265N), SEQ ID NO: 15 (Ldc2 N262T/K265N), and SEQ ID NO: 16 (Ldc2 S111C/N262T/K265N); and
   V) a non-naturally occurring polynucleotide comprising the polynucleotide sequence of a mutant of SEQ ID NO: 17.

2. A product of claim 1, which is I) the transformant, wherein the polynucleotide sequence comprises the polynucleotide sequence of a mutant of SEQ ID NO: 3, wherein the mutant of SEQ ID NO:3 encodes one of the mutants of SEQ ID NO:4 (Ldc2).

3. A product of claim 1, which is I) the transformant, wherein the host cell is an *Escherichia coli* (*E. coli*) cell.

4. A product of claim 3, wherein the polynucleotide sequence has been codon optimized for optimal polypeptide expression in the *E. coli* cell.

5. A product of claim 3, wherein the backbone plasmid is an *E. coli* expression plasmid vector.

6. A product of claim 5, wherein the backbone plasmid is selected from the group consisting of pUC18, pUC19, pBR322, pACYC, pET, pSC101, and any derived plasmids thereof.

7. A product of claim 5, wherein the expression plasmid vector further comprises a promoter polynucleotide sequence comprising the polynucleotide sequence of SEQ ID NO: 5, which is positioned upstream from the polynucleotide sequence.

8. A product of claim 1, which is I) the transformant, wherein the host cell is a *Hafnia alvei* (*H. alvei*) cell.

9. A product of claim 1, which is II) the expression plasmid vector, wherein the host cell is an *E. coli* cell.

10. A product of claim 9, wherein the polynucleotide sequence is a codon optimized polynucleotide for optimal polypeptide expression in the *E. coli* cell.

11. A product of claim 9, wherein the backbone plasmid is an *E. coli* expression plasmid vector.

12. A product of claim 11, wherein the backbone plasmid is selected from the group consisting of pUC18, pUC19, pBR322, pACYC, pET, pSC101, and any derived plasmids thereof.

13. A product of claim 12, wherein the expression plasmid vector further comprises a promoter polynucleotide sequence comprising the polynucleotide sequence of SEQ ID NO: 5, which is positioned upstream from the polynucleotide sequence.

14. A product of claim 1, which is II) the expression plasmid vector, wherein the host cell is a *H. alvei* cell.

15. A product of claim 1, which is III) the first mutant host cell, wherein the host cell is an *E. coli* cell.

16. A product of claim 1, which is IV) the non-naturally occurring polynucleotide, comprising a polynucleotide sequence encoding Ldc2 further comprising one or more mutations selected from the group consisting of a mutation at nucleotide position 331, a mutation at nucleotide position 332, a mutation at nucleotide position 333, a mutation at nucleotide position 784, a mutation at nucleotide position 785, a mutation at nucleotide position 786, a mutation at nucleotide position 793, a mutation at nucleotide position 794, and a mutation at nucleotide position 795.

17. A product of claim 16, wherein the mutation at the nucleotide position 332 is mutated to G, the mutation at the nucleotide position 785 is mutated to a C, and the mutation at the nucleotide position 795 is mutated to a T or C.

18. A product of claim 16, wherein the polynucleotide sequence encoding Ldc2 is the polynucleotide sequence of SEQ ID NO: 3 or a codon-optimized polynucleotide thereof.

19. A product of claim 18, wherein the codon-optimized polynucleotide is the polynucleotide sequence of SEQ ID NO: 17.

20. A product of claim 16, selected from the group consisting of SEQ ID NO: 18, SEQ ID NO: 19, SEQ ID NO: 20, SEQ ID NO: 21, SEQ ID NO: 22, SEQ ID NO: 23, and SEQ ID NO: 24.

21. A product of claim 1, which is IV) the non-naturally occurring polynucleotide, wherein the polynucleotide sequence has been codon optimized for optimal polypeptide expression in an *E. coli* cell.

22. A product of claim 1, which is VI) the non-naturally occurring polynucleotide, wherein the polynucleotide sequence has been codon optimized for optimal polypeptide expression in an *E. coli* cell.

23. A method for producing a polypeptide comprising the amino acid sequence of a mutant of SEQ ID NO: 4 (Ldc2), comprising:

obtaining the first mutant host cell of claim 1 III) and/or the transformant of claim 1 I);

culturing the first mutant host cell and/or the transformant under conditions effective for the expression of the polypeptide; and harvesting the polypeptide.

24. A method for producing cadaverine (1,5-pentanediamine) comprising:

1a) cultivating the first mutant host cell of claim 1 III) and/or the transformant of claim 1 I);

1b) producing cadaverine using the culture obtained from step 1a) to decarboxylate lysine; and 1c) extracting and purifying cadaverine using the culture obtained from step 1b).

* * * * *

UNITED STATES PATENT AND TRADEMARK OFFICE
CERTIFICATE OF CORRECTION

PATENT NO. : 10,647,976 B2
APPLICATION NO. : 15/321800
DATED : May 12, 2020
INVENTOR(S) : Howard Chou et al.

Page 1 of 1

It is certified that error appears in the above-identified patent and that said Letters Patent is hereby corrected as shown below:

On the Title Page

In Item (71), delete "CATHAY R&D CENTER CO., LTD., New District, Shanghai (CN); CATHAY INDUSTRIAL BIOTECH LTD., George Town, Grand Cayman (KY)" and insert --CATHAY BIOTECH INC., Shanghai (CN); CIBT America Inc., Newark, DE (US)--.

Signed and Sealed this
Twenty-first Day of July, 2020

Andrei Iancu
*Director of the United States Patent and Trademark Office*

SEQUENCE LISTING

<160> NUMBER OF SEQ ID NOS: 40

<210> SEQ ID NO 1
<211> LENGTH: 1071
<212> TYPE: DNA
<213> ORGANISM: Pseudomonas aeruginosa

<400> SEQUENCE: 1

| | | | | | |
|---|---|---|---|---|---|
| atgccctacg | aagccgatga | ctatctttcc | cggcacttcc | agaccagcgg | caccgacctg | 60 |
| gcgcggaagg | tcgacgaact | ggcggcccct | gcggctcccg | gcgacagccc | caatctcgcg | 120 |
| ctctaccgcg | agatgctctt | caccgtgacg | cgcatggccc | aggccgaccg | caaccgctgg | 180 |
| gacgccaaga | tcatgctgca | gaccctgcgc | gagatggagc | atgccttcag | cgtcctcgag | 240 |
| cagttcaagc | ggcgacgcaa | ggtcaccgtg | ttcggctcgg | cgcgcacgcc | ggtcgaacat | 300 |
| ccggtctatg | ccctggcgcg | caagctgggc | gaggaactgg | cccgctacga | cctgatggtg | 360 |
| atcaccggcg | ccggcggcgg | catcatggcc | gccgcccacg | aaggcgccgg | gctggagaac | 420 |
| agcctgggct | tcaacatcac | cctgcccttc | gagcagcacg | ccaaccatac | ggtggacggc | 480 |
| agcggcaacc | tgctgtcgtt | ccacttttc | ttcctgcgca | agctgttctt | cgtcaaggaa | 540 |
| gccgacgccc | tggtgctctg | ccccggcggc | ttcggcaccc | tcgacgaggc | actggaagtg | 600 |
| ctgaccctgg | tacagaccgg | caagagtccg | ctggtgccga | tcgtgctgct | cgaccagccg | 660 |
| ggcggccgct | actgggaaca | cgccctggag | ttcatgcagg | aacagttgct | ggagaatcac | 720 |
| tatatcctgc | cggccgacat | cgccctgatg | cgcctggtgc | attcggccga | agacgcggtg | 780 |
| aaggaaatcg | cccagttcta | ccgcaacttc | cactccagcc | gctggctgaa | aggcactttc | 840 |
| gtgattcgcc | tgaaccacgc | cctgaacgaa | gccgcgctgg | cgcacctgca | cgaacacttc | 900 |
| gccagcctct | gcctgagcgg | cggcttccag | cagcaggcct | acagcgagca | ggaacaggac | 960 |
| gaaccggagt | tccgcaacct | gacccgcctc | gccttcgtgt | tcaacgggcg | cgaccagggg | 1020 |
| cggctgcggg | aattgctgga | ctacatcaac | ctgccggaaa | actgggactg | a | 1071 |

<210> SEQ ID NO 2
<211> LENGTH: 438
<212> TYPE: PRT
<213> ORGANISM: Pseudomonas aeruginosa

<400> SEQUENCE: 2

Met Ala Ala Leu Asp Glu Leu Arg Gln Val Ala Pro Ser Ile Pro Leu
1               5                   10                  15

Phe Leu Leu Phe Arg Gln Leu Arg Ile Glu Gln Leu Ser Ser Gln Leu
            20                  25                  30

Leu Asp Glu Val Gln Gly Cys Phe Asn Leu Ala Ala Gly Pro Ala Arg
        35                  40                  45

Phe Ile Ala Glu Arg Ile Asp Ser Asp Leu Arg Glu Trp Arg Ala Pro
    50                  55                  60

Ala Gly Pro Arg Arg Leu Arg Asp Tyr Ala Pro Val Pro Arg Thr
65                  70                  75                  80

Pro Val Ser Ala Arg Tyr Asn Gly Arg Ala Arg Leu Asp Leu Ala Pro
                85                  90                  95

Ala Lys Gln Trp Arg Ile Gly Ser Gly Ser Thr Ala Glu Arg Leu Ala
            100                 105                 110

Thr Pro Leu Asn Asp Leu Ser Thr Ala Tyr Arg Lys Thr Ser Ala Gly
        115                 120                 125

Ala Pro Ala Ala His Ala Gly Asp Ile Ala Glu Ala Phe Arg Arg Ala

```
            130                 135                 140
Leu Trp Glu Ala Ala Ala Arg Leu Ala Arg Glu Asp Gly Asp Thr Trp
145                 150                 155                 160

Phe Phe Glu Ile Leu Arg Gly Asn Pro Gly Pro Gly Ile Glu Ala Gly
                165                 170                 175

Arg Glu Thr Pro Ala Lys Arg Trp His Gly Leu Ala Glu Thr Leu Asp
            180                 185                 190

Ser Ser Pro Arg Leu Asp Pro Leu Arg Val Ala Leu Ser Ala Pro Gly
                195                 200                 205

Leu Asp Ser Arg Gly Arg Pro Ala Ser Phe Gly Val Pro Ala Ala Val
210                 215                 220

Val Cys Arg Tyr Leu Arg Arg His Gly Ile Ala Pro Leu Arg Thr Gly
225                 230                 235                 240

Asp Tyr Arg Phe Leu Leu Leu Phe Pro Gln Gly Ala Arg Ala Glu His
                245                 250                 255

Ala Gln Pro Leu Val Asp Arg Leu Cys Glu Phe Lys Arg Arg His Asp
            260                 265                 270

Asp Asp Ala Pro Leu Lys Gln Val Leu Pro Glu Leu Leu Asp Ser Ser
        275                 280                 285

Pro Leu Tyr Arg Tyr Ile Gly Leu Arg Glu Leu Cys Ala Met Ile His
    290                 295                 300

Glu Ala Ser Leu Arg Leu His Leu Thr Ala Leu Ala Asp Ala Ala Ala
305                 310                 315                 320

Arg Thr Ala Gly His Ala Ala Leu Ala Pro Ala Thr Val Tyr Gly His
                325                 330                 335

Leu Val Arg Asp Glu Thr Glu Ala Val Ala Ile Asp Arg Leu Gly Gly
            340                 345                 350

Arg Val Val Ala Ser Leu Val Gly Val His Pro Ala Ala Thr Pro Leu
        355                 360                 365

Leu Leu Pro Gly Glu Arg Val Ala Glu Ser Pro Ala Leu Ile Asp
    370                 375                 380

Tyr Leu Leu Ala Leu Gln Ala Phe Gly Glu His Phe Pro Gly Phe Ala
385                 390                 395                 400

Pro Glu Leu Gln Gly Ile Glu Ile Asp Glu Arg Gly Arg Tyr Arg Val
                405                 410                 415

Arg Cys Val Arg Pro Ala Ala Leu Ala Arg Gly Ser Val Leu Arg Leu
            420                 425                 430

Ala Thr Arg Arg Pro Asp
        435

<210> SEQ ID NO 3
<211> LENGTH: 2256
<212> TYPE: DNA
<213> ORGANISM: Pseudomnas aeruginosa

<400> SEQUENCE: 3
atgtataaag acctcaaatt tcccgtcctc atcgtccatc gcgacatcaa ggccgacacc        60
gttgccggcg aacgcgtgcg gggcatcgcc cacgaactgg agcaggacgg cttcagcatt       120
ctctccaccg ccagctccgc cgaggggcgc atcgtcgctt ccacccacca cggcctggcc       180
tgcattctgg tcgccgccga aggtgccggg aaaaccagc gcctgctgca ggatgtggtc        240
gaactgatcc gcgtggcccg cgtgcgggcg ccgcaattgc cgatcttcgc cctcggcgag       300
caggtgacca tcgagaacgc gccggccgag tccatggccg acctgcacca gttgcgcggc       360
```

| | |
|---|---|
| atcctctacc tgttcgaaga caccgtgccg ttcctcgccc gccaggtcgc ccgggcggcg | 420 |
| cgcaactacc tggccgggct gctgccgcca ttcttccgtg cgctggtcga gcacaccgcg | 480 |
| cagtccaact attcctggca tacgccgggc acggcggcg tgtcgccta tcgcaagagt | 540 |
| ccggtgggac aggcgttcca ccagttcttc ggggagaaca cgctgcgttc cgacctgtcg | 600 |
| gtctcggtcc ccgagctggg atcgctgctc gaccataccg gcccctggc cgaggccgag | 660 |
| gaccgtgccg cgcgcaattt cggcgccgac cataccttct tcgtgatcaa tggcacttcc | 720 |
| accgcgaaca agatcgtctg gcactccatg gtcggtcgcg aagacctggt gctggtggac | 780 |
| cgcaactgcc acaagtcgat cctccactcg atcatcatga ccggggcgat accgctctac | 840 |
| ctgactccgg aacgcaacga actggggatc atcgggccga tcccgctgag cgaattcagc | 900 |
| aagcagtcga tcgccgcgaa gatcgccgcc agcccgctgg cgcgcggccg cgagccgaag | 960 |
| gtgaagctgg cggtggtgac taactccacc tacgacggcc tgtgctacaa cgccgagctg | 1020 |
| atcaagcaga ccctcggcga cagcgtcgag gtgttgcact cgacgaggc ttggtacgcc | 1080 |
| tatgccgcgt tccacgagtt ctacgacgga cgctatggca tgggcacctc gcgcagcgag | 1140 |
| gagggacccc tggtgttcgc cacccactcc acgcacaaga tgctcgccgc cttcagccag | 1200 |
| gcctcgatga tccacgtgca ggatggcggg acccggaagc tggacgtggc gcgcttcaac | 1260 |
| gaagccttca tgatgcacat ctcgacctcg ccgcagtacg gcatcatcgc ttcgctggac | 1320 |
| gtggcttcgg cgatgatgga agggcccgcc gggcgttcgc tgatccagga gccttcgac | 1380 |
| gaggccctca gcttccgccg ggccctggcc aacgtacggc agaacctgga ccggaacgac | 1440 |
| tggtggttcg gcgtctggca gccggagcag gtggagggca ccgaccaggt cggcacccat | 1500 |
| gactgggtgc tggagccgag cgccgactgg cacggcttcg gcgatatcgc gaagactac | 1560 |
| gtgctgctcg acccgatcaa ggtcaccctg accaccccgg gcctgagcgc tggcggcaag | 1620 |
| ctcagcgagc aggggattcc ggccgccatc gtcagccgct tcctctggga gcgcgggctg | 1680 |
| gtggtggaga aaaccggtct ctactccttc ctggtgctgt tctcgatggg catcaccaag | 1740 |
| ggcaagtgga gcaccctggt caccgaactg ctcgaattca gcgctgttta cgacgccaac | 1800 |
| ctgccgctgc ttgacgtctt gccctccgtg gcccaggccg cggcaagcg ctacaacgga | 1860 |
| gtgggcctgc gcgacctcag cgacgccatg cacgccagct accgcgacaa cgccacggcg | 1920 |
| aaggccatga gcgcatgta cacggtgctg ccggaggtcg cgatgcggcc gtccgaggcc | 1980 |
| tacgacaagc tggtgcgcgg cgaggtcgag gcggtaccga tcgctcggtt ggaagggcgc | 2040 |
| atcgcggccg tcatgctggt accctatccg ccgggtatcc cgctgatcat gccgggtgag | 2100 |
| cgcttcaccg aggcgacccg ctcgatcctc gactatctcg agttcgcgcg gaccttcgag | 2160 |
| cgcgccttcc ctggtttcga ctccgatgtg catggcctgc agcatcagga cggaccgtcc | 2220 |
| gggcgctgct ataccgttga atgcataaag gaatga | 2256 |

<210> SEQ ID NO 4
<211> LENGTH: 751
<212> TYPE: PRT
<213> ORGANISM: Pseudomonas aeruginosa

<400> SEQUENCE: 4

Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
            20                  25                  30

Leu Glu Gln Asp Gly Phe Ser Ile Leu Ser Thr Ala Ser Ser Ala Glu

```
                35                  40                  45
Gly Arg Ile Val Ala Ser Thr His His Gly Leu Ala Cys Ile Leu Val
 50                  55                  60

Ala Ala Glu Gly Ala Gly Glu Asn Gln Arg Leu Leu Gln Asp Val Val
 65                  70                  75                  80

Glu Leu Ile Arg Val Ala Arg Val Arg Ala Pro Gln Leu Pro Ile Phe
                 85                  90                  95

Ala Leu Gly Glu Gln Val Thr Ile Glu Asn Ala Pro Ala Glu Ser Met
                100                 105                 110

Ala Asp Leu His Gln Leu Arg Gly Ile Leu Tyr Leu Phe Glu Asp Thr
                115                 120                 125

Val Pro Phe Leu Ala Arg Gln Val Ala Arg Ala Arg Asn Tyr Leu
130                 135                 140

Ala Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Val Ala
                165                 170                 175

Tyr Arg Lys Ser Pro Val Gly Gln Ala Phe His Gln Phe Phe Gly Glu
                180                 185                 190

Asn Thr Leu Arg Ser Asp Leu Ser Val Ser Val Pro Glu Leu Gly Ser
                195                 200                 205

Leu Leu Asp His Thr Gly Pro Leu Ala Glu Ala Glu Asp Arg Ala Ala
210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Asn Cys His Lys Ser Ile Leu His Ser Ile Ile
                260                 265                 270

Met Thr Gly Ala Ile Pro Leu Tyr Leu Thr Pro Glu Arg Asn Glu Leu
                275                 280                 285

Gly Ile Ile Gly Pro Ile Pro Leu Ser Glu Phe Ser Lys Gln Ser Ile
                290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Thr Leu Gly Asp Ser Val Glu Val Leu
                340                 345                 350

His Phe Asp Glu Ala Trp Tyr Ala Tyr Ala Ala Phe His Glu Phe Tyr
                355                 360                 365

Asp Gly Arg Tyr Gly Met Gly Thr Ser Arg Ser Glu Glu Gly Pro Leu
                370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
                405                 410                 415

Ala Arg Phe Asn Glu Ala Phe Met Met His Ile Ser Thr Ser Pro Gln
                420                 425                 430

Tyr Gly Ile Ile Ala Ser Leu Asp Val Ala Ser Ala Met Met Glu Gly
                435                 440                 445

Pro Ala Gly Arg Ser Leu Ile Gln Glu Thr Phe Asp Glu Ala Leu Ser
450                 455                 460
```

-continued

```
Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
            485                 490                 495

Val Gly Thr His Asp Trp Val Leu Glu Pro Ser Ala Asp Trp His Gly
        500                 505                 510

Phe Gly Asp Ile Ala Glu Asp Tyr Val Leu Leu Asp Pro Ile Lys Val
    515                 520                 525

Thr Leu Thr Thr Pro Gly Leu Ser Ala Gly Gly Lys Leu Ser Glu Gln
530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
            565                 570                 575

Gly Ile Thr Lys Gly Lys Trp Ser Thr Leu Val Thr Glu Leu Leu Glu
        580                 585                 590

Phe Lys Arg Cys Tyr Asp Ala Asn Leu Pro Leu Leu Asp Val Leu Pro
    595                 600                 605

Ser Val Ala Gln Ala Gly Gly Lys Arg Tyr Asn Gly Val Gly Leu Arg
610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
            645                 650                 655

Pro Ser Glu Ala Tyr Asp Lys Leu Val Arg Gly Glu Val Glu Ala Val
        660                 665                 670

Pro Ile Ala Arg Leu Glu Gly Arg Ile Ala Ala Val Met Leu Val Pro
    675                 680                 685

Tyr Pro Pro Gly Ile Pro Leu Ile Met Pro Gly Glu Arg Phe Thr Glu
690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
            725                 730                 735

Asp Gly Pro Ser Gly Arg Cys Tyr Thr Val Glu Cys Ile Lys Glu
        740                 745                 750
```

<210> SEQ ID NO 5
<211> LENGTH: 38
<212> TYPE: DNA
<213> ORGANISM: artificial
<220> FEATURE:
<223> OTHER INFORMATION: synthetic, synthesized

<400> SEQUENCE: 5
agtttattct tgacatgtag tgagggggct ggtataat     38

<210> SEQ ID NO 6
<211> LENGTH: 751
<212> TYPE: PRT
<213> ORGANISM: artificial
<220> FEATURE:
<223> OTHER INFORMATION: synthetic, synthesized

<400> SEQUENCE: 6

```
Met Tyr Lys Asp Leu Lys Phe Pro Val Leu Ile Val His Arg Asp Ile
1               5                   10                  15
```

Lys Ala Asp Thr Val Ala Gly Glu Arg Val Arg Gly Ile Ala His Glu
            20                  25                  30

Leu Glu Gln Asp Gly Phe Ser Ile Leu Ser Thr Ala Ser Ser Ala Glu
        35                  40                  45

Gly Arg Ile Val Ala Ser Thr His His Gly Leu Ala Cys Ile Leu Val
50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Cys Met
            100                 105                 110

Ala Asp Leu His Gln Leu Arg Gly Ile Leu Tyr Leu Phe Glu Asp Thr
        115                 120                 125

Val Pro Phe Leu Ala Arg Gln Val Ala Arg Ala Arg Asn Tyr Leu
130                 135                 140

Ala Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Gly Val Ala
                165                 170                 175

Tyr Arg Lys Ser Pro Val Gly Gln Ala Phe His Gln Phe Phe Gly Glu
            180                 185                 190

Asn Thr Leu Arg Ser Asp Leu Ser Val Ser Val Pro Glu Leu Gly Ser
        195                 200                 205

Leu Leu Asp His Thr Gly Pro Leu Ala Glu Ala Glu Asp Arg Ala Ala
        210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Asn Cys His Lys Ser Ile Leu His Ser Ile Ile
            260                 265                 270

Met Thr Gly Ala Ile Pro Leu Tyr Leu Thr Pro Glu Arg Asn Glu Leu
        275                 280                 285

Gly Ile Ile Gly Pro Ile Pro Leu Ser Glu Phe Ser Lys Gln Ser Ile
290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Thr Leu Gly Asp Ser Val Glu Val Leu
            340                 345                 350

His Phe Asp Glu Ala Trp Tyr Ala Tyr Ala Ala Phe His Glu Phe Tyr
        355                 360                 365

Asp Gly Arg Tyr Gly Met Gly Thr Ser Arg Ser Glu Glu Gly Pro Leu
370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
                405                 410                 415

Ala Arg Phe Asn Glu Ala Phe Met Met His Ile Ser Thr Ser Pro Gln
            420                 425                 430

Tyr Gly Ile Ile Ala Ser Leu Asp Val Ala Ser Ala Met Met Glu Gly
            435                 440                 445

Pro Ala Gly Arg Ser Leu Ile Gln Glu Thr Phe Asp Glu Ala Leu Ser
    450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Gly Thr Asp Gln
                485                 490                 495

Val Gly Thr His Asp Trp Val Leu Glu Pro Ser Ala Asp Trp His Gly
            500                 505                 510

Phe Gly Asp Ile Ala Glu Asp Tyr Val Leu Leu Asp Pro Ile Lys Val
            515                 520                 525

Thr Leu Thr Thr Pro Gly Leu Ser Ala Gly Gly Lys Leu Ser Glu Gln
        530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Val Thr Glu Leu Leu Glu
            580                 585                 590

Phe Lys Arg Cys Tyr Asp Ala Asn Leu Pro Leu Leu Asp Val Leu Pro
        595                 600                 605

Ser Val Ala Gln Ala Gly Gly Lys Arg Tyr Asn Gly Val Gly Leu Arg
    610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Glu Val Glu Ala Val
            660                 665                 670

Pro Ile Ala Arg Leu Glu Gly Arg Ile Ala Ala Val Met Leu Val Pro
        675                 680                 685

Tyr Pro Pro Gly Ile Pro Leu Ile Met Pro Gly Glu Arg Phe Thr Glu
    690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
            740                 745                 750

<210> SEQ ID NO 7
<211> LENGTH: 1333
<212> TYPE: DNA
<213> ORGANISM: Hafnia alvei

<400> SEQUENCE: 7
ttgactttgt taaaagtcag gcataagatc aaaatactgt atatataaca atgtatttat     60
atacagtatt ttatactttt tatctaacgt cagagagggc aatattatga gtggtggaga    120
tggcaagggt cacaatagtg gagcacatga ttccggtggc agcattaatg gaacttctgg    180
gaaaggtggg ccatcaagcg gaggagcatc agataattct gggtggagtt cggaaaataa    240
cccgtggggc ggtggtaact cgggaatgat tggtggcagt caaggaggta acggagctaa    300
tcatggtggc gaaaatacat cttctaacta tggaaagat gtatcacgcc aaatcggtga    360

```
tgcgatagcc agaaaggaag gcatcaatcc gaaaatattc actgggtact ttatccgttc      420
agatggatat ttgatcggaa taacgccact tgtcagtggt gatgcctttg gcgttaatct      480
tggcctgttc aataacaatc aaaatagtag tagtgaaaat aagggatgga atggaaggaa      540
tggagatggc attaaaaata gtagccaagg tggatggaag attaaaacta atgaacttac      600
ttcaaaccaa gtagctgctg ctaaatccgt tccagaacct aaaaatagta aatattataa      660
gtccatgaga gaagctagcg atgaggttat taattctaat ttaaaccaag gcatggagt       720 tggtgaggca gctagagctg aaagagatta cagagaaaaa gtaaagaacg caatcaatga      780
taatagtccc aatgtgctac aggatgctat taaatttaca gcagattttt ataaggaagt      840 tttaacgct tacggagaaa aagccgaaaa actagccaag ttattagctg atcaagctaa       900
aggtaaaaag atccgcaatg tagaagatgc attgaaatct tatgaaaaac acaaggctaa      960
cattaacaaa aaaatcaatg cgaaagatcg cgaagctatc gccaaggctt ggagtctat      1020 ggatgtagaa aaagccgcaa aaatatatc caagttcagc aaaggactag gttgggttgg     1080
cccagctatc gatataactg attggtttac agaattatac aaagcagtga aaactgataa     1140
ttggagatct ctttatgtta aaactgaaac tattgcagta gggctagctg caacccatgt     1200
caccgcctta gcattcagtg ctgtcttggg tgggcctata ggtattttag gttatggttt     1260
gattatggct ggggttgggg cgttagttaa cgagacaata gttgacgagg caaataaggt     1320
cattgggatt taa                                                        1333

<210> SEQ ID NO 8
<211> LENGTH: 336
<212> TYPE: DNA
<213> ORGANISM: Hafnia alvei

<400> SEQUENCE: 8
ctatatttta gcggtcacat tttttatttc aaaacaaaca gaaagaacac caataggaat       60
tgatgtcata aaaataaaaa taaaatacaa agtcattaaa tatgttttg gcacaccatc       120 cttaaaaaaa cctgttttcc aaaattcttt tttcgtatat ctaagcgctg ctttctctat      180
tagaaaccga gagaaaggaa atagaatagc gctagccaaa ccaaagattc tgagcgcaat      240
tattttaggt tcgtcatcac cataactggc gtaaagaata caagcagcca taaagtatcc      300
ccaaaacata ttatgtatgt aatatttcct tgtcat                                336

<210> SEQ ID NO 9
<211> LENGTH: 1077
<212> TYPE: DNA
<213> ORGANISM: Hafnia alvei

<400> SEQUENCE: 9
atgagtggtg gagacggtaa aggtcacaat agtggagcac atgattccgg tggcagcatt       60
aatggaactt cggggaaagg tggacctgat tctggtggcg atattgggaa caaccatcca      120
catattacaa tcaccggtgg acgggaagta ggtcaagggg gagctggtat caactgggt       180 ggtggttctg gtcatggtaa cggcggggc tcagttgcca tccaagaata taacacgagt       240
aaatatccta acacgggagg atttcctcct cttggagacg ctagctggct gttaaatcct      300
ccaaaatggt cggttattga agtaaaatca gaaaactcag catggcgctc ttatattact      360
catgttcaag gtcatgttta caattgact tttgatggta cgggtaagct cattgatacc       420
gcgtatgtta attatgaacc cagtgatgat actcgttgga gcccgcttaa aagttttaaa      480
```

```
tataataaag gaaccgctga aaaacaggtt agggatgcca ttaacaatga aaagaagca          540 gttaaggacg ctgttaaatt tactgcagac ttctataaag aggttttaa ggtttacgga          600 gaaaaagccg agaagctcgc taagttatta gcagatcaag ctaaaggcaa aaggttcgc          660 aacgtagaaa atgccttgaa atcttatgaa aaatataaga ctaacattaa caaaaaaatc         720
aatgcgaaag atcgcgaagc tattgctaaa gccttggagt ctatggatgt aggaaaagcc        780
gcaaaaaata tagccaagtt cagtaaagga ctaggttggg ttggccctgc tatcgatata        840
actgattggt ttacagaatt atacaaggca gtggaaactg ataattggag atctttttat        900
gttaaaactg aaactattgc agtagggcta gctgcaaccc atgttgccgc cttggcattc        960
agcgctgtct tgggtgggcc tgtaggtatt ttgggttatg gtttgattat ggctggggtt       1020
ggggcgttag ttaatgagac aatagttgac gaggcaaata aggttattgg gctttaa          1077
```

<210> SEQ ID NO 10
<211> LENGTH: 336
<212> TYPE: DNA
<213> ORGANISM: Hafnia alvei

<400> SEQUENCE: 10

```
ctataattta gcggtcacat tttttatttc aaaaaaaaca gaaataacac ctataggaat          60
tgatgtcata aaataaaaa ttaaatacaa agtcattaaa tatgttttg gcacgccatc          120 cttaaaaaaa ccagtttccc aaaattcttt tttcgtatat ctaagcgcgg ttttctctat        180
taaaaaccga gagaaaggga ataggatagc actagccaaa ccaaagattc tgagcgcaat       240
tattttaggt tcgttatccc cataactggc gtaaagaata caaacagcca taaagtaccc       300
ccaaaacata ttatgtatat aatatttcct tgtcat                                   336
```

<210> SEQ ID NO 11
<211> LENGTH: 751
<212> TYPE: PRT
<213> ORGANISM: artificial
<220> FEATURE:
<223> OTHER INFORMATION: synthetic, synthesized

<400> SEQUENCE: 11

```
Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
            20                  25                  30

Leu Glu Gln Asp Gly Phe Ser Ile Leu Ser Thr Ala Ser Ser Ala Glu
        35                  40                  45

Gly Arg Ile Val Ala Ser Thr His His Gly Leu Ala Cys Ile Leu Val
    50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Ser Met
            100                 105                 110

Ala Asp Leu His Gln Leu Arg Gly Ile Leu Tyr Leu Phe Glu Asp Thr
        115                 120                 125

Val Pro Phe Leu Ala Arg Gln Val Ala Arg Ala Arg Asn Tyr Leu
    130                 135                 140

Ala Gly Leu Leu Pro Pro Phe Phe Arg Ala Leu Val Glu His Thr Ala
145                 150                 155                 160
```

```
Gln Ser Asn Tyr Ser Trp His Thr Pro Gly His Gly Gly Val Ala
                165                 170                 175

Tyr Arg Lys Ser Pro Val Gly Gln Ala Phe His Gln Phe Phe Gly Glu
            180                 185                 190

Asn Thr Leu Arg Ser Asp Leu Ser Val Ser Val Pro Glu Leu Gly Ser
                195                 200                 205

Leu Leu Asp His Thr Gly Pro Leu Ala Glu Ala Glu Asp Arg Ala Ala
        210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Thr Cys His Lys Ser Ile Leu His Ser Ile Ile
                260                 265                 270

Met Thr Gly Ala Ile Pro Leu Tyr Leu Thr Pro Glu Arg Asn Glu Leu
            275                 280                 285

Gly Ile Ile Gly Pro Ile Pro Leu Ser Glu Phe Ser Lys Gln Ser Ile
        290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Thr Leu Gly Asp Ser Val Glu Val Leu
            340                 345                 350

His Phe Asp Glu Ala Trp Tyr Ala Tyr Ala Ala Phe His Glu Phe Tyr
        355                 360                 365

Asp Gly Arg Tyr Gly Met Gly Thr Ser Arg Ser Glu Glu Gly Pro Leu
    370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
            405                 410                 415

Ala Arg Phe Asn Glu Ala Phe Met Met His Ile Ser Thr Ser Pro Gln
        420                 425                 430

Tyr Gly Ile Ile Ala Ser Leu Asp Val Ala Ser Ala Met Met Glu Gly
    435                 440                 445

Pro Ala Gly Arg Ser Leu Ile Gln Glu Thr Phe Asp Glu Ala Leu Ser
450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
            485                 490                 495

Val Gly Thr His Asp Trp Val Leu Glu Pro Ser Ala Asp Trp His Gly
        500                 505                 510

Phe Gly Asp Ile Ala Glu Asp Tyr Val Leu Leu Asp Pro Ile Lys Val
    515                 520                 525

Thr Leu Thr Thr Pro Gly Leu Ser Ala Gly Lys Leu Ser Glu Gln
530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575
```

```
Gly Ile Thr Lys Gly Lys Trp Ser Thr Leu Val Thr Glu Leu Leu Glu
            580                 585                 590

Phe Lys Arg Cys Tyr Asp Ala Asn Leu Pro Leu Leu Asp Val Leu Pro
        595                 600                 605

Ser Val Ala Gln Ala Gly Gly Lys Arg Tyr Asn Gly Val Gly Leu Arg
    610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Glu Val Glu Ala Val
            660                 665                 670

Pro Ile Ala Arg Leu Glu Gly Arg Ile Ala Ala Val Met Leu Val Pro
        675                 680                 685

Tyr Pro Pro Gly Ile Pro Leu Ile Met Pro Gly Glu Arg Phe Thr Glu
    690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
            740                 745                 750

<210> SEQ ID NO 12
<211> LENGTH: 751
<212> TYPE: PRT
<213> ORGANISM: artificial
<220> FEATURE:
<223> OTHER INFORMATION: synthetic, synthesized

<400> SEQUENCE: 12

Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
            20                  25                  30

Leu Glu Gln Asp Gly Phe Ser Ile Leu Ser Thr Ala Ser Ser Ala Glu
        35                  40                  45

Gly Arg Ile Val Ala Ser Thr His His Gly Leu Ala Cys Ile Leu Val
    50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Ser Met
            100                 105                 110

Ala Asp Leu His Gln Leu Arg Gly Ile Leu Tyr Leu Phe Glu Asp Thr
        115                 120                 125

Val Pro Phe Leu Ala Arg Gln Val Ala Arg Ala Arg Asn Tyr Leu
    130                 135                 140

Ala Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Val Ala
                165                 170                 175

Tyr Arg Lys Ser Pro Val Gly Gln Ala Phe His Gln Phe Phe Gly Glu
            180                 185                 190
```

```
Asn Thr Leu Arg Ser Asp Leu Ser Val Ser Val Pro Glu Leu Gly Ser
            195                 200                 205

Leu Leu Asp His Thr Gly Pro Leu Ala Glu Ala Glu Asp Arg Ala Ala
    210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Asn Cys His Asn Ser Ile Leu His Ser Ile Ile
            260                 265                 270

Met Thr Gly Ala Ile Pro Leu Tyr Leu Thr Pro Glu Arg Asn Glu Leu
        275                 280                 285

Gly Ile Ile Gly Pro Ile Pro Leu Ser Glu Phe Ser Lys Gln Ser Ile
    290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Thr Leu Gly Asp Ser Val Glu Val Leu
            340                 345                 350

His Phe Asp Glu Ala Trp Tyr Ala Tyr Ala Ala Phe His Glu Phe Tyr
        355                 360                 365

Asp Gly Arg Tyr Gly Met Gly Thr Ser Arg Ser Glu Gly Pro Leu
    370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
                405                 410                 415

Ala Arg Phe Asn Glu Ala Phe Met Met His Ile Ser Thr Ser Pro Gln
            420                 425                 430

Tyr Gly Ile Ile Ala Ser Leu Asp Val Ala Ser Ala Met Met Glu Gly
        435                 440                 445

Pro Ala Gly Arg Ser Leu Ile Gln Glu Thr Phe Asp Glu Ala Leu Ser
450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
                485                 490                 495

Val Gly Thr His Asp Trp Val Leu Glu Pro Ser Ala Asp Trp His Gly
            500                 505                 510

Phe Gly Asp Ile Ala Glu Asp Tyr Val Leu Leu Asp Pro Ile Lys Val
        515                 520                 525

Thr Leu Thr Thr Pro Gly Leu Ser Ala Gly Gly Lys Leu Ser Glu Gln
530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Val Thr Glu Leu Leu Glu
            580                 585                 590

Phe Lys Arg Cys Tyr Asp Ala Asn Leu Pro Leu Leu Asp Val Leu Pro
        595                 600                 605

Ser Val Ala Gln Ala Gly Gly Lys Arg Tyr Asn Gly Val Gly Leu Arg
```

```
            610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Glu Val Glu Ala Val
                660                 665                 670

Pro Ile Ala Arg Leu Glu Gly Arg Ile Ala Ala Val Met Leu Val Pro
                675                 680                 685

Tyr Pro Pro Gly Ile Pro Leu Ile Met Pro Gly Glu Arg Phe Thr Glu
            690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
                740                 745                 750

<210> SEQ ID NO 13
<211> LENGTH: 751
<212> TYPE: PRT
<213> ORGANISM: artificial
<220> FEATURE:
<223> OTHER INFORMATION: synthetic, synthesized

<400> SEQUENCE: 13

Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
                20                  25                  30

Leu Glu Gln Asp Gly Phe Ser Ile Leu Ser Thr Ala Ser Ser Ala Glu
            35                  40                  45

Gly Arg Ile Val Ala Ser Thr His His Gly Leu Ala Cys Ile Leu Val
    50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Cys Met
                100                 105                 110

Ala Asp Leu His Gln Leu Arg Gly Ile Leu Tyr Leu Phe Glu Asp Thr
            115                 120                 125

Val Pro Phe Leu Ala Arg Gln Val Ala Arg Ala Arg Asn Tyr Leu
    130                 135                 140

Ala Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Gly Val Ala
                165                 170                 175

Tyr Arg Lys Ser Pro Val Gly Gln Ala Phe His Gln Phe Phe Gly Glu
                180                 185                 190

Asn Thr Leu Arg Ser Asp Leu Ser Val Ser Val Pro Glu Leu Gly Ser
            195                 200                 205

Leu Leu Asp His Thr Gly Pro Leu Ala Glu Ala Glu Asp Arg Ala Ala
    210                 215                 220

Arg Asn Phe Gly Ala Asp His Thr Phe Phe Val Ile Asn Gly Thr Ser
```

```
                225                 230                 235                 240
        Thr Ala Asn Lys Ile Val Trp His Ser Met Val Gly Arg Glu Asp Leu
                        245                 250                 255

Val Leu Val Asp Arg Thr Cys His Lys Ser Ile Leu His Ser Ile Ile
                        260                 265                 270

Met Thr Gly Ala Ile Pro Leu Tyr Leu Thr Pro Glu Arg Asn Glu Leu
                        275                 280                 285

Gly Ile Ile Gly Pro Ile Pro Leu Ser Glu Phe Ser Lys Gln Ser Ile
                        290                 295                 300

Ala Ala Lys Ile Ala Ala Ser Pro Leu Ala Arg Gly Arg Glu Pro Lys
        305                 310                 315                 320

Val Lys Leu Ala Val Val Thr Asn Ser Thr Tyr Asp Gly Leu Cys Tyr
                        325                 330                 335

Asn Ala Glu Leu Ile Lys Gln Thr Leu Gly Asp Ser Val Glu Val Leu
                        340                 345                 350

His Phe Asp Glu Ala Trp Tyr Ala Tyr Ala Ala Phe His Glu Phe Tyr
                        355                 360                 365

Asp Gly Arg Tyr Gly Met Gly Thr Ser Arg Ser Glu Glu Gly Pro Leu
                        370                 375                 380

Val Phe Ala Thr His Ser Thr His Lys Met Leu Ala Ala Phe Ser Gln
        385                 390                 395                 400

Ala Ser Met Ile His Val Gln Asp Gly Gly Thr Arg Lys Leu Asp Val
                        405                 410                 415

Ala Arg Phe Asn Glu Ala Phe Met Met His Ile Ser Thr Ser Pro Gln
                        420                 425                 430

Tyr Gly Ile Ile Ala Ser Leu Asp Val Ala Ser Ala Met Met Glu Gly
                        435                 440                 445

Pro Ala Gly Arg Ser Leu Ile Gln Glu Thr Phe Asp Glu Ala Leu Ser
                        450                 455                 460

Phe Arg Arg Ala Leu Ala Asn Val Arg Gln Asn Leu Asp Arg Asn Asp
        465                 470                 475                 480

Trp Trp Phe Gly Val Trp Gln Pro Glu Gln Val Glu Gly Thr Asp Gln
                        485                 490                 495

Val Gly Thr His Asp Trp Val Leu Glu Pro Ser Ala Asp Trp His Gly
                        500                 505                 510

Phe Gly Asp Ile Ala Glu Asp Tyr Val Leu Leu Asp Pro Ile Lys Val
                        515                 520                 525

Thr Leu Thr Thr Pro Gly Leu Ser Ala Gly Gly Lys Leu Ser Glu Gln
                        530                 535                 540

Gly Ile Pro Ala Ala Ile Val Ser Arg Phe Leu Trp Glu Arg Gly Leu
        545                 550                 555                 560

Val Val Glu Lys Thr Gly Leu Tyr Ser Phe Leu Val Leu Phe Ser Met
                        565                 570                 575

Gly Ile Thr Lys Gly Lys Trp Ser Thr Leu Val Thr Glu Leu Leu Glu
                        580                 585                 590

Phe Lys Arg Cys Tyr Asp Ala Asn Leu Pro Leu Leu Asp Val Leu Pro
                        595                 600                 605

Ser Val Ala Gln Ala Gly Gly Lys Arg Tyr Asn Gly Val Gly Leu Arg
                        610                 615                 620

Asp Leu Ser Asp Ala Met His Ala Ser Tyr Arg Asp Asn Ala Thr Ala
        625                 630                 635                 640

Lys Ala Met Lys Arg Met Tyr Thr Val Leu Pro Glu Val Ala Met Arg
                        645                 650                 655
```

```
Pro Ser Glu Ala Tyr Asp Lys Leu Val Arg Gly Glu Ala Val
            660                 665                 670

Pro Ile Ala Arg Leu Glu Gly Arg Ile Ala Ala Val Met Leu Val Pro
            675                 680                 685

Tyr Pro Pro Gly Ile Pro Leu Ile Met Pro Gly Glu Arg Phe Thr Glu
            690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
                740                 745                 750

<210> SEQ ID NO 14
<211> LENGTH: 751
<212> TYPE: PRT
<213> ORGANISM: artificial
<220> FEATURE:
<223> OTHER INFORMATION: synthetic, synthesized

<400> SEQUENCE: 14

Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
                20                  25                  30

Leu Glu Gln Asp Gly Phe Ser Ile Leu Ser Thr Ala Ser Ser Ala Glu
            35                  40                  45

Gly Arg Ile Val Ala Ser Thr His His Gly Leu Ala Cys Ile Leu Val
        50                  55                  60

Ala Ala Glu Gly Ala Gly Glu Asn Gln Arg Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Cys Met
            100                 105                 110

Ala Asp Leu His Gln Leu Arg Gly Ile Leu Tyr Leu Phe Glu Asp Thr
        115                 120                 125

Val Pro Phe Leu Ala Arg Gln Val Ala Arg Ala Arg Asn Tyr Leu
    130                 135                 140

Ala Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Gly Val Ala
                165                 170                 175

Tyr Arg Lys Ser Pro Val Gly Gln Ala Phe His Gln Phe Phe Gly Glu
            180                 185                 190

Asn Thr Leu Arg Ser Asp Leu Ser Val Ser Val Pro Glu Leu Gly Ser
        195                 200                 205

Leu Leu Asp His Thr Gly Pro Leu Ala Glu Ala Glu Asp Arg Ala Ala
    210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Asn Cys His Asn Ser Ile Leu His Ser Ile Ile
            260                 265                 270
```

-continued

```
Met Thr Gly Ala Ile Pro Leu Tyr Leu Thr Pro Glu Arg Asn Glu Leu
            275                 280                 285

Gly Ile Ile Gly Pro Ile Pro Leu Ser Glu Phe Ser Lys Gln Ser Ile
        290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Thr Leu Gly Asp Ser Val Glu Val Leu
                340                 345                 350

His Phe Asp Glu Ala Trp Tyr Ala Tyr Ala Ala Phe His Glu Phe Tyr
            355                 360                 365

Asp Gly Arg Tyr Gly Met Gly Thr Ser Arg Ser Glu Glu Gly Pro Leu
        370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
                405                 410                 415

Ala Arg Phe Asn Glu Ala Phe Met Met His Ile Ser Thr Ser Pro Gln
            420                 425                 430

Tyr Gly Ile Ile Ala Ser Leu Asp Val Ala Ser Ala Met Met Glu Gly
        435                 440                 445

Pro Ala Gly Arg Ser Leu Ile Gln Glu Thr Phe Asp Glu Ala Leu Ser
450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
                485                 490                 495

Val Gly Thr His Asp Trp Val Leu Glu Pro Ser Ala Asp Trp His Gly
            500                 505                 510

Phe Gly Asp Ile Ala Glu Asp Tyr Val Leu Leu Asp Pro Ile Lys Val
        515                 520                 525

Thr Leu Thr Thr Pro Gly Leu Ser Ala Gly Gly Lys Leu Ser Glu Gln
530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Val Thr Glu Leu Leu Glu
            580                 585                 590

Phe Lys Arg Cys Tyr Asp Ala Asn Leu Pro Leu Leu Asp Val Leu Pro
        595                 600                 605

Ser Val Ala Gln Ala Gly Gly Lys Arg Tyr Asn Gly Val Gly Leu Arg
610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Glu Val Glu Ala Val
            660                 665                 670

Pro Ile Ala Arg Leu Glu Gly Arg Ile Ala Ala Val Met Leu Val Pro
        675                 680                 685
```

```
Tyr Pro Pro Gly Ile Pro Leu Ile Met Pro Gly Glu Arg Phe Thr Glu
    690             695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
            740                 745                 750
```

<210> SEQ ID NO 15
<211> LENGTH: 751
<212> TYPE: PRT
<213> ORGANISM: artificial
<220> FEATURE:
<223> OTHER INFORMATION: synthetic, synthesized

<400> SEQUENCE: 15

```
Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
            20                  25                  30

Leu Glu Gln Asp Gly Phe Ser Ile Leu Ser Thr Ala Ser Ser Ala Glu
        35                  40                  45

Gly Arg Ile Val Ala Ser Thr His His Gly Leu Ala Cys Ile Leu Val
    50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Ser Met
            100                 105                 110

Ala Asp Leu His Gln Leu Arg Gly Ile Leu Tyr Leu Phe Glu Asp Thr
        115                 120                 125

Val Pro Phe Leu Ala Arg Gln Val Ala Arg Ala Ala Arg Asn Tyr Leu
    130                 135                 140

Ala Gly Leu Leu Pro Pro Phe Arg Ala Leu Val Glu His Thr Ala
145                 150                 155                 160

Gln Ser Asn Tyr Ser Trp His Thr Pro Gly His Gly Gly Gly Val Ala
                165                 170                 175

Tyr Arg Lys Ser Pro Val Gly Gln Ala Phe His Gln Phe Phe Gly Glu
            180                 185                 190

Asn Thr Leu Arg Ser Asp Leu Ser Val Ser Val Pro Glu Leu Gly Ser
        195                 200                 205

Leu Leu Asp His Thr Gly Pro Leu Ala Glu Ala Glu Asp Arg Ala Ala
    210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Thr Cys His Asn Ser Ile Leu His Ser Ile Ile
            260                 265                 270

Met Thr Gly Ala Ile Pro Leu Tyr Leu Thr Pro Glu Arg Asn Glu Leu
        275                 280                 285

Gly Ile Ile Gly Pro Ile Pro Leu Ser Glu Phe Ser Lys Gln Ser Ile
    290                 295                 300
```

```
Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Thr Leu Gly Asp Ser Val Glu Val Leu
            340                 345                 350

His Phe Asp Glu Ala Trp Tyr Ala Tyr Ala Ala Phe His Glu Phe Tyr
        355                 360                 365

Asp Gly Arg Tyr Gly Met Gly Thr Ser Arg Ser Glu Gly Pro Leu
    370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
                405                 410                 415

Ala Arg Phe Asn Glu Ala Phe Met Met His Ile Ser Thr Ser Pro Gln
            420                 425                 430

Tyr Gly Ile Ile Ala Ser Leu Asp Val Ala Ser Ala Met Met Glu Gly
        435                 440                 445

Pro Ala Gly Arg Ser Leu Ile Gln Glu Thr Phe Asp Glu Ala Leu Ser
450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
                485                 490                 495

Val Gly Thr His Asp Trp Val Leu Glu Pro Ser Ala Asp Trp His Gly
                500                 505                 510

Phe Gly Asp Ile Ala Glu Asp Tyr Val Leu Leu Asp Pro Ile Lys Val
            515                 520                 525

Thr Leu Thr Thr Pro Gly Leu Ser Ala Gly Gly Lys Leu Ser Glu Gln
530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Val Thr Glu Leu Leu Glu
            580                 585                 590

Phe Lys Arg Cys Tyr Asp Ala Asn Leu Pro Leu Leu Asp Val Leu Pro
        595                 600                 605

Ser Val Ala Gln Ala Gly Gly Lys Arg Tyr Asn Gly Val Gly Leu Arg
610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Glu Val Glu Ala Val
            660                 665                 670

Pro Ile Ala Arg Leu Glu Gly Arg Ile Ala Ala Val Met Leu Val Pro
        675                 680                 685

Tyr Pro Pro Gly Ile Pro Leu Ile Met Pro Gly Glu Arg Phe Thr Glu
        690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
```

```
                        725                 730                 735
Asp Gly Pro Ser Gly Arg Cys Tyr Thr Val Glu Cys Ile Lys Glu
            740                 745                 750

<210> SEQ ID NO 16
<211> LENGTH: 751
<212> TYPE: PRT
<213> ORGANISM: artificial
<220> FEATURE:
<223> OTHER INFORMATION: synthetic, synthesized

<400> SEQUENCE: 16

Met Tyr Lys Asp Leu Lys Phe Pro Val Leu Ile Val His Arg Asp Ile
1               5                   10                  15

Lys Ala Asp Thr Val Ala Gly Glu Arg Val Arg Gly Ile Ala His Glu
            20                  25                  30

Leu Glu Gln Asp Gly Phe Ser Ile Leu Ser Thr Ala Ser Ser Ala Glu
        35                  40                  45

Gly Arg Ile Val Ala Ser Thr His His Gly Leu Ala Cys Ile Leu Val
    50                  55                  60

Ala Ala Glu Gly Ala Gly Glu Asn Gln Arg Leu Leu Gln Asp Val Val
65                  70                  75                  80

Glu Leu Ile Arg Val Ala Arg Val Arg Ala Pro Gln Leu Pro Ile Phe
                85                  90                  95

Ala Leu Gly Glu Gln Val Thr Ile Glu Asn Ala Pro Ala Glu Cys Met
            100                 105                 110

Ala Asp Leu His Gln Leu Arg Gly Ile Leu Tyr Leu Phe Glu Asp Thr
        115                 120                 125

Val Pro Phe Leu Ala Arg Gln Val Ala Arg Ala Arg Asn Tyr Leu
    130                 135                 140

Ala Gly Leu Leu Pro Pro Phe Phe Arg Ala Leu Val Glu His Thr Ala
145                 150                 155                 160

Gln Ser Asn Tyr Ser Trp His Thr Pro Gly His Gly Gly Gly Val Ala
                165                 170                 175

Tyr Arg Lys Ser Pro Val Gly Gln Ala Phe His Gln Phe Phe Gly Glu
            180                 185                 190

Asn Thr Leu Arg Ser Asp Leu Ser Val Ser Val Pro Glu Leu Gly Ser
        195                 200                 205

Leu Leu Asp His Thr Gly Pro Leu Ala Glu Ala Glu Asp Arg Ala Ala
    210                 215                 220

Arg Asn Phe Gly Ala Asp His Thr Phe Phe Val Ile Asn Gly Thr Ser
225                 230                 235                 240

Thr Ala Asn Lys Ile Val Trp His Ser Met Val Gly Arg Glu Asp Leu
                245                 250                 255

Val Leu Val Asp Arg Thr Cys His Asn Ser Ile Leu His Ser Ile Ile
            260                 265                 270

Met Thr Gly Ala Ile Pro Leu Tyr Leu Thr Pro Glu Arg Asn Glu Leu
        275                 280                 285

Gly Ile Ile Gly Pro Ile Pro Leu Ser Glu Phe Ser Lys Gln Ser Ile
    290                 295                 300

Ala Ala Lys Ile Ala Ala Ser Pro Leu Ala Arg Gly Arg Glu Pro Lys
305                 310                 315                 320

Val Lys Leu Ala Val Val Thr Asn Ser Thr Tyr Asp Gly Leu Cys Tyr
                325                 330                 335

Asn Ala Glu Leu Ile Lys Gln Thr Leu Gly Asp Ser Val Glu Val Leu
```

His Phe Asp Glu Ala Trp Tyr Ala Tyr Ala Ala Phe His Glu Phe Tyr
355                 360                 365

Asp Gly Arg Tyr Gly Met Gly Thr Ser Arg Ser Glu Glu Gly Pro Leu
370                 375                 380

Val Phe Ala Thr His Ser Thr His Lys Met Leu Ala Ala Phe Ser Gln
385                 390                 395                 400

Ala Ser Met Ile His Val Gln Asp Gly Gly Thr Arg Lys Leu Asp Val
            405                 410                 415

Ala Arg Phe Asn Glu Ala Phe Met Met His Ile Ser Thr Ser Pro Gln
        420                 425                 430

Tyr Gly Ile Ile Ala Ser Leu Asp Val Ala Ser Ala Met Met Glu Gly
    435                 440                 445

Pro Ala Gly Arg Ser Leu Ile Gln Glu Thr Phe Asp Glu Ala Leu Ser
450                 455                 460

Phe Arg Arg Ala Leu Ala Asn Val Arg Gln Asn Leu Asp Arg Asn Asp
465                 470                 475                 480

Trp Trp Phe Gly Val Trp Gln Pro Glu Gln Val Glu Gly Thr Asp Gln
                485                 490                 495

Val Gly Thr His Asp Trp Val Leu Glu Pro Ser Ala Asp Trp His Gly
            500                 505                 510

Phe Gly Asp Ile Ala Glu Asp Tyr Val Leu Leu Asp Pro Ile Lys Val
        515                 520                 525

Thr Leu Thr Thr Pro Gly Leu Ser Ala Gly Gly Lys Leu Ser Glu Gln
    530                 535                 540

Gly Ile Pro Ala Ala Ile Val Ser Arg Phe Leu Trp Glu Arg Gly Leu
545                 550                 555                 560

Val Val Glu Lys Thr Gly Leu Tyr Ser Phe Leu Val Leu Phe Ser Met
                565                 570                 575

Gly Ile Thr Lys Gly Lys Trp Ser Thr Leu Val Thr Glu Leu Leu Glu
            580                 585                 590

Phe Lys Arg Cys Tyr Asp Ala Asn Leu Pro Leu Leu Asp Val Leu Pro
        595                 600                 605

Ser Val Ala Gln Ala Gly Gly Lys Arg Tyr Asn Gly Val Gly Leu Arg
    610                 615                 620

Asp Leu Ser Asp Ala Met His Ala Ser Tyr Arg Asp Asn Ala Thr Ala
625                 630                 635                 640

Lys Ala Met Lys Arg Met Tyr Thr Val Leu Pro Glu Val Ala Met Arg
                645                 650                 655

Pro Ser Glu Ala Tyr Asp Lys Leu Val Arg Gly Val Glu Ala Val
            660                 665                 670

Pro Ile Ala Arg Leu Glu Gly Arg Ile Ala Ala Val Met Leu Val Pro
        675                 680                 685

Tyr Pro Pro Gly Ile Pro Leu Ile Met Pro Gly Glu Arg Phe Thr Glu
    690                 695                 700

Ala Thr Arg Ser Ile Leu Asp Tyr Leu Glu Phe Ala Arg Thr Phe Glu
705                 710                 715                 720

Arg Ala Phe Pro Gly Phe Asp Ser Asp Val His Gly Leu Gln His Gln
                725                 730                 735

Asp Gly Pro Ser Gly Arg Cys Tyr Thr Val Glu Cys Ile Lys Glu
            740                 745                 750

<210> SEQ ID NO 17

<211> LENGTH: 2256
<212> TYPE: DNA
<213> ORGANISM: artificial
<220> FEATURE:
<223> OTHER INFORMATION: synthetic, synthesized

<400> SEQUENCE: 17

| | | | | | |
|---|---|---|---|---|---|
| atgtacaaag | atctgaaatt | ccctgttctg | attgtacacc | gcgatatcaa | ggcggacacg | 60 |
| gtagccggcg | agcgtgttcg | cggtattgcc | cacgaactcg | aacaagacgg | ctttagcatt | 120 |
| ctctctacgg | cgtcttctgc | ggaaggccgc | attgtggcta | gcacgcacca | cggtctcgcc | 180 |
| tgcatcctcg | tggcagctga | gggtgcgggt | gagaatcagc | gtctgctcca | agacgtggtt | 240 |
| gagctgatcc | gtgtagctcg | cgtccgtgcg | ccacagctcc | cgatcttcgc | gctgggcgaa | 300 |
| caggtgacta | ttgaaaacgc | gcctgccgaa | tctatggccg | acctgcacca | gctccgcggc | 360 |
| attctgtatc | tcttcgagga | tactgtcccg | ttcctggcac | gtcaggttgc | acgcgcagcg | 420 |
| cgtaactacc | tcgctggcct | cctcccgcca | ttcttccgtg | cactcgtgga | gcacacggcc | 480 |
| caaagcaatt | actcttggca | caccccgggt | cacgtggtg | gtgtcgctta | ccgtaaatct | 540 |
| ccggtaggtc | aagctttcca | ccagttcttt | ggcgagaata | ccctccgctc | tgacctgtct | 600 |
| gttagcgttc | cagagctggg | cagcctgctg | gatcacactg | gccctctcgc | ggaagcagag | 660 |
| gatcgtgccg | ctcgcaattt | cggtgcggac | cacaccttct | tgtcatcaa | tggtacctct | 720 |
| actgcgaaca | aaatcgtttg | gcactctatg | gttggtcgcg | aggacctggt | gctggtcgat | 780 |
| cgtaactgtc | acaaatctat | tctgcactcc | attatcatga | cgggtgctat | cccactgtac | 840 |
| ctgactccgg | aacgcaacga | actgggtatt | atcggcccta | ttccactctc | cgagttttct | 900 |
| aaacaatcta | tcgcagcaaa | aattgccgcc | tccccactcg | cgcgtggtcg | tgaaccgaaa | 960 |
| gttaaactgg | ctgtcgttac | caactctacc | tatgacggtc | tgtgttacaa | cgcggaactg | 1020 |
| atcaaacaaa | ccctcggcga | ctctgtcgag | gtactgcatt | tcgacgaggc | ttggtatgct | 1080 |
| tatgcggcgt | tcacgagtt | ctacgacggc | cgctacggta | tgggcacttc | tcgttccgaa | 1140 |
| gagggtccgc | tggtctttgc | tacccattct | acccacaaga | tgctcgcggc | ttttcccaa | 1200 |
| gctagcatga | ttcacgttca | ggatggtggt | acgcgcaagc | tggacgtcgc | ccgctttaac | 1260 |
| gaagccttta | tgatgcacat | cagcacctct | ccacagtacg | gcatcattgc | gtctctcgat | 1320 |
| gtcgcaagcg | ctatgatgga | aggtcctgcc | ggtcgtagcc | tgatccaaga | gacgttcgat | 1380 |
| gaggcgctgt | ccttccgtcg | tgctctggcg | aatgtccgtc | agaacctgga | ccgtaatgat | 1440 |
| tggtggttcg | gtgtctggca | accggagcag | gttgagggca | ccgaccaggt | aggtactcac | 1500 |
| gactgggttc | tcgagcctag | cgcggactgg | catggtttg | gtgacattgc | ggaggattac | 1560 |
| gttctcctcg | atcctatcaa | agttaccctg | accaccccag | gtctgagcgc | tggcggtaaa | 1620 |
| ctctctgaac | aaggcatccc | ggcagctatc | gttagccgtt | cctgtggga | acgtggtctg | 1680 |
| gtggtcgaga | aaacgggtct | gtactctttc | ctggttctgt | tctccatggg | tatcacgaaa | 1740 |
| ggcaaatggt | ctactctggt | taccgagctg | ctcgaattca | aacgctgtta | cgacgcgaat | 1800 |
| ctgccactcc | tggatgtgct | gccttctgta | gcgcaggcgg | gtggtaaacg | ctataacggt | 1860 |
| gtaggtctgc | gtgatctgtc | cgatgccatg | cacgcttctt | atcgtgacaa | tgccacggcg | 1920 |
| aaggccatga | agcgtatgta | tacggtgctc | ccggaagtag | ccatgcgccc | gtccgaagct | 1980 |
| tatgataagc | tcgtacgcgg | tgaagtcgaa | gctgttccta | ttgcacgtct | cgagggtcgt | 2040 |
| attgcggcgg | ttatgctggt | tccgtacccg | ccaggtatcc | cgctcattat | gccgggtgaa | 2100 |
| cgttttactg | aagctacccg | ctccattctg | gactatctgg | agtttgcccg | taccttcgag | 2160 |

```
cgcgcgttcc cgggctttga ctctgatgtt cacggcctcc aacatcaaga tggcccgtct    2220
ggccgttgtt ataccgttga atgcatcaag gaataa                              2256
```

<210> SEQ ID NO 18
<211> LENGTH: 2256
<212> TYPE: DNA
<213> ORGANISM: artificial
<220> FEATURE:
<223> OTHER INFORMATION: synthetic, synthesized

<400> SEQUENCE: 18

```
atgtacaaag atctgaaatt ccctgttctg attgtacacc gcgatatcaa ggcggacacg      60
gtagccggcg agcgtgttcg cggtattgcc cacgaactcg aacaagacgg ctttagcatt     120
ctctctacgg cgtcttctgc ggaaggccgc attgtggcta gcacgcacca cggtctcgcc     180
tgcatcctcg tggcagctga gggtgcgggt gagaatcagc gtctgctcca agacgtggtt     240
gagctgatcc gtgtagctcg cgtccgtgcg ccacagctcc cgatcttcgc gctgggcgaa     300
caggtgacta ttgaaaacgc gcctgccgaa tgtatggccg acctgcacca gctccgcggc     360
attctgtatc tcttcgagga tactgtcccg ttcctggcac gtcaggttgc acgcgcagcg     420
cgtaactacc tcgctggcct cctcccgcca ttcttccgtg cactcgtgga gcacacggcc     480
caaagcaatt actcttggca caccccgggt cacgtggtg gtgtcgctta ccgtaaatct     540
ccggtaggtc aagctttcca ccagttcttt ggcgagaata ccctccgctc tgacctgtct     600
gttagcgttc cagagctggg cagcctgctg atcacactg gccctctcgc ggaagcagag     660
gatcgtgccg ctcgcaattt cggtgcggac cacaccttct ttgtcatcaa tggtacctct     720
actgcgaaca aaatcgtttg gcactctatg gttggtcgcg aggacctggt gctggtcgat     780
cgtaactgtc acaaatctat tctgcactcc attatcatga cgggtgctat cccactgtac     840
ctgactccgg aacgcaacga actgggtatt atcggcccta ttccactctc cgagttttct     900
aaacaatcta tcgcagcaaa aattgccgcc tccccactcg cgcgtggtcg tgaaccgaaa     960
gttaaactgg ctgtcgttac caactctacc tatgacggtc tgtgttacaa cgcggaactg    1020
atcaaacaaa ccctcggcga ctctgtcgag gtactgcatt tcgacgaggc ttggtatgct    1080
tatgcggcgt ttcacgagtt ctacgacggc cgctacggta tgggcacttc tcgttccgaa    1140
gagggtccgc tggtctttgc taccattct acccacaaga tgctcgcggc ttttttcccaa    1200 gctagcatga ttcacgttca ggatggtggt acgcgcaagc tggacgtcgc ccgctttaac    1260
gaagccttta tgatgcacat cagcacctct ccacagtacg gcatcattgc gtctctcgat    1320
gtcgcaagcg ctatgatgga aggtcctgcc ggtcgtagcc tgatccaaga gacgttcgat    1380
gaggcgctgt ccttccgtcg tgctctggcg aatgtccgtc agaacctgga ccgtaatgat    1440
tggtggttcg gtgtctggca accggagcag gttgagggca ccgaccaggt aggtactcac    1500
gactgggttc tcgagcctag cgcggactgg catggttttg gtgacattgc ggaggattac    1560
gttctcctcg atcctatcaa agttaccctg accacccag gtctgagcgc tggcggtaaa    1620
ctctctgaac aaggcatccc ggcagctatc gttagccgtt cctgtgggga acgtggtctg    1680
gtggtcgaga aaacgggtct gtactctttc ctggttctgt tctccatggg tatcacgaaa    1740
ggcaaatggt ctactctggt taccgagctg ctcgaattca aacgctgtta cgacgcgaat    1800
ctgccactcc tggatgtgct gccttctgta gcgcaggcgg tggtaaacg ctataacggt    1860 gtaggtctgc gtgatctgtc cgatgccatg cacgcttctt atcgtgacaa tgccacggcg    1920
```

| | |
|---|---:|
| aaggccatga agcgtatgta tacggtgctc ccggaagtag ccatgcgccc gtccgaagct | 1980 |
| tatgataagc tcgtacgcgg tgaagtcgaa gctgttccta ttgcacgtct cgagggtcgt | 2040 |
| attgcggcgg ttatgctggt tccgtacccg ccaggtatcc cgctcattat gccgggtgaa | 2100 |
| cgttttactg aagctacccg ctccattctg gactatctgg agtttgcccg taccttcgag | 2160 |
| cgcgcgttcc cgggctttga ctctgatgtt cacggcctcc aacatcaaga tggcccgtct | 2220 |
| ggccgttgtt ataccgttga atgcatcaag gaataa | 2256 |

<210> SEQ ID NO 19
<211> LENGTH: 2256
<212> TYPE: DNA
<213> ORGANISM: artificial
<220> FEATURE:
<223> OTHER INFORMATION: synthetic, synthesized

<400> SEQUENCE: 19

| | |
|---|---:|
| atgtacaaag atctgaaatt ccctgttctg attgtacacc gcgatatcaa ggcggacacg | 60 |
| gtagccggcg agcgtgttcg cggtattgcc cacgaactcg aacaagacgg ctttagcatt | 120 |
| ctctctacgg cgtcttctgc ggaaggccgc attgtggcta gcacgcacca cggtctcgcc | 180 |
| tgcatcctcg tggcagctga gggtgcgggt gagaatcagc gtctgctcca agacgtggtt | 240 |
| gagctgatcc gtgtagctcg cgtccgtgcg ccacagctcc cgatcttcgc gctgggcgaa | 300 |
| caggtgacta ttgaaaacgc gcctgccgaa tctatggccg acctgcacca gctccgcggc | 360 |
| attctgtatc tcttcgagga tactgtcccg ttcctggcac gtcaggttgc acgcgcagcg | 420 |
| cgtaactacc tcgctggcct cctcccgcca ttcttccgtg cactcgtgga gcacacggcc | 480 |
| caaagcaatt actcttggca caccccgggt cacggtggtg gtgtcgctta ccgtaaatct | 540 |
| ccggtaggtc aagcttttcca ccagttcttt ggcgagaata ccctccgctc tgacctgtct | 600 |
| gttagcgttc cagagctggg cagcctgctg gatcacactg gccctctcgc ggaagcagag | 660 |
| gatcgtgccg ctcgcaattt cggtgcggac cacaccttct tgtcatcaa tggtacctct | 720 |
| actgcgaaca aaatcgtttg gcactctatg gttggtcgcg aggacctggt gctggtcgat | 780 |
| cgtacctgtc acaaatctat tctgcactcc attatcatga cgggtgctat cccactgtac | 840 |
| ctgactccgg aacgcaacga actgggtatt atcggcccta ttccactctc cgagttttct | 900 |
| aaacaatcta tcgcagcaaa aattgccgcc tccccactcg cgcgtggtcg tgaaccgaaa | 960 |
| gttaaactgg ctgtcgttac caactctacc tatgacggtc tgtgttacaa cgcggaactg | 1020 |
| atcaaacaaa ccctcggcga ctctgtcgag gtactgcatt tcgacgaggc ttggtatgct | 1080 |
| tatgcggcgt ttcacgagtt ctacgacggc cgctacggta tgggcacttc tcgttccgaa | 1140 |
| gagggtccgc tggtcttttgc tacccattct acccacaaga tgctcgcggc ttttccccaa | 1200 |
| gctagcatga ttcacgttca ggatggtggt acgcgcaagc tggacgtcgc ccgctttaac | 1260 |
| gaagccttta tgatgcacat cagcacctct ccacagtacg gcatcattgc gtctctcgat | 1320 |
| gtcgcaagcg ctatgatgga aggtcctgcc ggtcgtagcc tgatccaaga gacgttcgat | 1380 |
| gaggcgctgt ccttccgtcg tgctctggcg aatgtccgtc agaacctgga ccgtaatgat | 1440 |
| tggtggttcg tgtctggca accggagcag gttgagggca ccgaccaggt aggtactcac | 1500 |
| gactgggttc tcgagcctag cgcggactgg catggttttg gtgacattgc ggaggattac | 1560 |
| gttctcctcg atcctatcaa agttacccctg accaccccag gtctgagcgc tggcggtaaa | 1620 |
| ctctctgaac aaggcatccc ggcagctatc gttagccgtt cctgtgggga acgtggtctg | 1680 |
| gtggtcgaga aaacgggtct gtactctttc ctggttctgt tctccatggg tatcacgaaa | 1740 |

| | |
|---|---|
| ggcaaatggt ctactctggt taccgagctg ctcgaattca aacgctgtta cgacgcgaat | 1800 |
| ctgccactcc tggatgtgct gccttctgta gcgcaggcgg gtggtaaacg ctataacggt | 1860 |
| gtaggtctgc gtgatctgtc cgatgccatg cacgcttctt atcgtgacaa tgccacggcg | 1920 |
| aaggccatga agcgtatgta tacggtgctc ccggaagtag ccatgcgccc gtccgaagct | 1980 |
| tatgataagc tcgtacgcgg tgaagtcgaa gctgttccta ttgcacgtct cgagggtcgt | 2040 |
| attgcggcgg ttatgctggt tccgtacccg ccaggtatcc cgctcattat gccgggtgaa | 2100 |
| cgttttactg aagctacccg ctccattctg gactatctgg agtttgcccg taccttcgag | 2160 |
| cgcgcgttcc cgggctttga ctctgatgtt cacggcctcc aacatcaaga tggcccgtct | 2220 |
| ggccgttgtt ataccgttga atgcatcaag gaataa | 2256 |

<210> SEQ ID NO 20
<211> LENGTH: 2256
<212> TYPE: DNA
<213> ORGANISM: artificial
<220> FEATURE:
<223> OTHER INFORMATION: synthetic, synthesized

<400> SEQUENCE: 20

| | |
|---|---|
| atgtacaaag atctgaaatt ccctgttctg attgtacacc gcgatatcaa ggcggacacg | 60 |
| gtagccggcg agcgtgttcg cggtattgcc cacgaactcg aacaagacgg ctttagcatt | 120 |
| ctctctacgg cgtcttctgc ggaaggccgc attgtggcta gcacgcacca cggtctcgcc | 180 |
| tgcatcctcg tggcagctga gggtgcgggt gagaatcagc gtctgctcca agacgtggtt | 240 |
| gagctgatcc gtgtagctcg cgtccgtgcg ccacagctcc cgatcttcgc gctgggcgaa | 300 |
| caggtgacta ttgaaaacgc gcctgccgaa tctatggccg acctgcacca gctccgcggc | 360 |
| attctgtatc tcttcgagga tactgtcccg ttcctggcac gtcaggttgc acgcgcagcg | 420 |
| cgtaactacc tcgctggcct cctcccgcca ttcttccgtg cactcgtgga gcacacggcc | 480 |
| caaagcaatt actcttggca caccccgggt cacggtggtg gtgtcgctta ccgtaaatct | 540 |
| ccggtaggtc aagctttcca ccagttcttt ggcgagaata ccctccgctc tgacctgtct | 600 |
| gttagcgttc cagagctggg cagcctgctg atcacactg gccctctcgc ggaagcagag | 660 |
| gatcgtgccg ctcgcaattt cggtgcggac cacaccttct ttgtcatcaa tggtacctct | 720 |
| actgcgaaca aaatcgtttg gcactctatg gttggtcgcg aggacctggt gctggtcgat | 780 |
| cgtaactgtc acaactctat tctgcactcc attatcatga cgggtgctat cccactgtac | 840 |
| ctgactccgg aacgcaacga actgggtatt atcggcccta ttccactctc cgagttttct | 900 |
| aaacaatcta tcgcagcaaa aattgccgcc tccccactcg cgcgtggtcg tgaaccgaaa | 960 |
| gttaaactgg ctgtcgttac caactctacc tatgacggtc tgtgttacaa cgcggaactg | 1020 |
| atcaaacaaa ccctcggcga ctctgtcgag gtactgcatt cgacgaggc ttggtatgct | 1080 |
| tatgcggcgt tcacgagtt ctacgacggc cgctacggta tgggcacttc tcgttccgaa | 1140 |
| gagggtccgc tggtctttgc tacccattct acccacaaga tgctcgcggc tttttcccaa | 1200 |
| gctagcatga ttcacgttca ggatggtggt acgcgcaagc tggacgtcgc ccgctttaac | 1260 |
| gaagccttta tgatgcacat cagcacctct ccacagtacg gcatcattgc gtctctcgat | 1320 |
| gtcgcaagcg ctatgatgga aggtcctgcc ggtcgtagcc tgatccaaga gacgttcgat | 1380 |
| gaggcgctgt ccttccgtcg tgctctggcg aatgtccgtc agaacctgga ccgtaatgat | 1440 |
| tggtggttcg gtgtctggca accggagcag gttgagggca ccgaccaggt aggtactcac | 1500 |

-continued

| | |
|---|---|
| gactgggttc tcgagcctag cgcggactgg catggttttg gtgacattgc ggaggattac | 1560 |
| gttctcctcg atcctatcaa agttaccctg accaccccag gtctgagcgc tggcggtaaa | 1620 |
| ctctctgaac aaggcatccc ggcagctatc gttagccgtt tcctgtggga acgtggtctg | 1680 |
| gtggtcgaga aaacgggtct gtactctttc ctggttctgt tctccatggg tatcacgaaa | 1740 |
| ggcaaatggt ctactctggt taccgagctg ctcgaattca aacgctgtta cgacgcgaat | 1800 |
| ctgccactcc tggatgtgct gccttctgta gcgcaggcgg gtggtaaacg ctataacggt | 1860 |
| gtaggtctgc gtgatctgtc cgatgccatg cacgcttctt atcgtgacaa tgccacggcg | 1920 |
| aaggccatga agcgtatgta tacggtgctc ccggaagtag ccatgcgccc gtccgaagct | 1980 |
| tatgataagc tcgtacgcgg tgaagtcgaa gctgttccta ttgcacgtct cgagggtcgt | 2040 |
| attgcggcgg ttatgctggt tccgtacccg ccaggtatcc cgctcattat gccgggtgaa | 2100 |
| cgttttactg aagctacccg ctccattctg gactatctgg agtttgcccg taccttcgag | 2160 |
| cgcgcgttcc cgggctttga ctctgatgtt cacggcctcc aacatcaaga tggcccgtct | 2220 |
| ggccgttgtt ataccgttga atgcatcaag gaataa | 2256 |

<210> SEQ ID NO 21
<211> LENGTH: 2256
<212> TYPE: DNA
<213> ORGANISM: artificial
<220> FEATURE:
<223> OTHER INFORMATION: synthetic, synthesized

<400> SEQUENCE: 21

| | |
|---|---|
| atgtacaaag atctgaaatt ccctgttctg attgtacacc gcgatatcaa ggcggacacg | 60 |
| gtagccggcg agcgtgttcg cggtattgcc cacgaactcg aacaagacgg ctttagcatt | 120 |
| ctctctacgg cgtcttctgc ggaaggccgc attgtggcta gcacgcacca cggtctcgcc | 180 |
| tgcatcctcg tggcagctga gggtgcgggt gagaatcagc gtctgctcca agacgtggtt | 240 |
| gagctgatcc gtgtagctcg cgtccgtgcg ccacagctcc cgatcttcgc gctgggcgaa | 300 |
| caggtgacta ttgaaaacgc gcctgccgaa tgtatggccg acctgcacca gctccgcggc | 360 |
| attctgtatc tcttcgagga tactgtcccg ttcctggcac gtcaggttgc acgcgcagcg | 420 |
| cgtaactacc tcgctggcct cctcccgcca ttcttccgtg cactcgtgga gcacacggcc | 480 |
| caaagcaatt actcttggca caccccgggt cacggtggtg gtgtcgctta ccgtaaatct | 540 |
| ccggtaggtc aagctttcca ccagttcttt ggcgagaata ccctccgctc tgacctgtct | 600 |
| gttagcgttc cagagctggg cagcctgctg atcacactg gccctctcgc ggaagcagag | 660 |
| gatcgtgccg ctcgcaattt cggtgcggac cacaccttct ttgtcatcaa tggtacctct | 720 |
| actgcgaaca aaatcgtttg gcactctatg gttggtcgcg aggacctggt gctggtcgat | 780 |
| cgtacctgtc acaaatctat tctgcactcc attatcatga cgggtgctat cccactgtac | 840 |
| ctgactccgg aacgcaacga actgggtatt atcggcccta ttccactctc cgagttttct | 900 |
| aaacaatcta tcgcagcaaa aattgccgcc tccccactcg cgcgtggtcg tgaaccgaaa | 960 |
| gttaaactgg ctgtcgttac caactctacc tatgacggtc tgtgttacaa cgcggaactg | 1020 |
| atcaaacaaa ccctcggcga ctctgtcgag gtactgcatt tcgacgaggc ttggtatgct | 1080 |
| tatgcggcgt tcacgagtt ctacgacggc cgctacggta tgggcacttc tcgttccgaa | 1140 |
| gagggtccgc tggtctttgc tacccattct acccacaaga tgctcgcggc ttttcccaa | 1200 |
| gctagcatga ttcacgttca ggatggtggt acgcgcaagc tggacgtcgc ccgctttaac | 1260 |
| gaagccttta tgatgcacat cagcacctct ccacagtacg gcatcattgc gtctctcgat | 1320 |

| | |
|---|---|
| gtcgcaagcg ctatgatgga aggtcctgcc ggtcgtagcc tgatccaaga gacgttcgat | 1380 |
| gaggcgctgt ccttccgtcg tgctctggcg aatgtccgtc agaacctgga ccgtaatgat | 1440 |
| tggtggttcg gtgtctggca accggagcag gttgagggca ccgaccaggt aggtactcac | 1500 |
| gactgggttc tcgagcctag cgcggactgg catggttttg gtgacattgc ggaggattac | 1560 |
| gttctcctcg atcctatcaa agttaccctg accaccccag gtctgagcgc tggcggtaaa | 1620 |
| ctctctgaac aaggcatccc ggcagctatc gttagccgtt cctgtgggda acgtggtctg | 1680 |
| gtggtcgaga aaacgggtct gtactctttc ctggttctgt tctccatggg tatcacgaaa | 1740 |
| ggcaaatggt ctactctggt taccgagctg ctcgaattca aacgctgtta cgacgcgaat | 1800 |
| ctgccactcc tggatgtgct gccttctgta gcgcaggcgg tggtaaacg ctataacggt | 1860 |
| gtaggtctgc gtgatctgtc cgatgccatg cacgcttctt atcgtgacaa tgccacggcg | 1920 |
| aaggccatga agcgtatgta tacggtgctc ccggaagtag ccatgcgccc gtccgaagct | 1980 |
| tatgataagc tcgtacgcgg tgaagtcgaa gctgttccta ttgcacgtct cgagggtcgt | 2040 |
| attgcggcgg ttatgctggt tccgtacccg ccaggtatcc cgctcattat gccgggtgaa | 2100 |
| cgttttactg aagctacccg ctccattctg gactatctgg agtttgcccg taccttcgag | 2160 |
| cgcgcgttcc cgggctttga ctctgatgtt cacggcctcc aacatcaaga tggcccgtct | 2220 |
| ggccgttgtt ataccgttga atgcatcaag gaataa | 2256 |

<210> SEQ ID NO 22
<211> LENGTH: 2256
<212> TYPE: DNA
<213> ORGANISM: artificial
<220> FEATURE:
<223> OTHER INFORMATION: synthetic, synthesized

<400> SEQUENCE: 22

| | |
|---|---|
| atgtacaaag atctgaaatt ccctgttctg attgtacacc gcgatatcaa ggcggacacg | 60 |
| gtagccggcg agcgtgttcg cggtattgcc cacgaactcg aacaagacgg ctttagcatt | 120 |
| ctctctacgg cgtcttctgc ggaaggccgc attgtggcta gcacgcacca cggtctcgcc | 180 |
| tgcatcctcg tggcagctga gggtgcgggt gagaatcagc gtctgctcca agacgtggtt | 240 |
| gagctgatcc gtgtagctcg cgtccgtgcg ccacagctcc cgatcttcgc gctgggcgaa | 300 |
| caggtgacta ttgaaaacgc gcctgccgaa tgtatggccg acctgcacca gctccgcggc | 360 |
| attctgtatc tcttcgagga tactgtcccg ttcctggcac gtcaggttgc acgcgcagcg | 420 |
| cgtaactacc tcgctggcct cctcccgcca ttcttccgtg cactcgtgga gcacacggcc | 480 |
| caaagcaatt actcttggca caccccgggt cacggtggtg gtgtcgctta ccgtaaatct | 540 |
| ccggtaggtc aagcttttcca ccagttcttt ggcgagaata ccctccgctc tgacctgtct | 600 |
| gttagcgttc cagagctggg cagcctgctg atcacactg gccctctcgc ggaagcagag | 660 |
| gatcgtgccg ctcgcaattt cggtgcggac cacaccttct ttgtcatcaa tggtacctct | 720 |
| actgcgaaca aaatcgtttg gcactctatg ttggtcgcg aggacctggt gctggtcgat | 780 |
| cgtaactgtc acaactctat tctgcactcc attatcatga cgggtgctat cccactgtac | 840 |
| ctgactccgg aacgcaacga actgggtatt atcggcccta ttccactctc cgagttttct | 900 |
| aaacaatcta tcgcagcaaa aattgccgcc tccccactcg cgcgtggtcg tgaaccgaaa | 960 |
| gttaaactgg ctgtcgttac caactctacc tatgacggtc tgtgttacaa cgcggaactg | 1020 |
| atcaaacaaa ccctcggcga ctctgtcgag gtactgcatt tcgacgaggc ttggtatgct | 1080 |

```
tatgcggcgt ttcacgagtt ctacgacggc cgctacggta tgggcacttc tcgttccgaa    1140
gagggtccgc tggtctttgc tacccattct acccacaaga tgctcgcggc ttttcccaa    1200 gctagcatga ttcacgttca ggatggtggt acgcgcaagc tggacgtcgc ccgctttaac    1260
gaagccttta tgatgcacat cagcacctct ccacagtacg gcatcattgc gtctctcgat    1320
gtcgcaagcg ctatgatgga aggtcctgcc ggtcgtagcc tgatccaaga gacgttcgat    1380
gaggcgctgt ccttccgtcg tgctctggcg aatgtccgtc agaacctgga ccgtaatgat    1440
tggtggttcg gtgtctggca accggagcag gttgagggca ccgaccaggt aggtactcac    1500
gactgggttc tcgagcctag cgcggactgg catggttttg gtgacattgc ggaggattac    1560
gttctcctcg atcctatcaa agttaccctg accaccccag gtctgagcgc tggcggtaaa    1620
ctctctgaac aaggcatccc ggcagctatc gttagccgtt tcctgtggga acgtggtctg    1680
gtggtcgaga aaacgggtct gtactctttc ctggttctgt tctccatggg tatcacgaaa    1740
ggcaaatggt ctactctggt taccgagctg ctcgaattca aacgctgtta cgacgcgaat    1800
ctgccactcc tggatgtgct gccttctgta gcgcaggcgg gtggtaaacg ctataacggt    1860
gtaggtctgc gtgatctgtc cgatgccatg cacgcttctt atcgtgacaa tgccacggcg    1920
aaggccatga agcgtatgta tacggtgctc ccggaagtag ccatgcgccc gtccgaagct    1980
tatgataagc tcgtacgcgg tgaagtcgaa gctgttccta ttgcacgtct cgagggtcgt    2040 attgcgcgg ttatgctggt tccgtacccg ccaggtatcc cgctcattat gccgggtgaa    2100
cgttttactg aagctacccg ctccattctg gactatctgg agtttgcccg taccttcgag    2160
cgcgcgttcc cgggctttga ctctgatgtt cacggcctcc aacatcaaga tggcccgtct    2220
ggccgttgtt ataccgttga atgcatcaag gaataa                              2256
```

<210> SEQ ID NO 23
<211> LENGTH: 2256
<212> TYPE: DNA
<213> ORGANISM: artificial
<220> FEATURE:
<223> OTHER INFORMATION: synthetic, synthesized

<400> SEQUENCE: 23

```
atgtacaaag atctgaaatt ccctgttctg attgtacacc gcgatatcaa ggcggacacg     60
gtagccggcg agcgtgttcg cggtattgcc cacgaactcg aacaagacgg ctttagcatt    120
ctctctacgg cgtcttctgc ggaaggccgc attgtggcta gcacgcacca cggtctcgcc    180
tgcatcctcg tggcagctga gggtgcgggt gagaatcagc gtctgctcca agacgtggtt    240
gagctgatcc gtgtagctcg cgtccgtgcg ccacagctcc gatcttcgc gctgggcgaa    300 caggtgacta ttgaaaacgc gcctgccgaa tctatggccg acctgcacca gctccgcggc    360
attctgtatc tcttcgagga tactgtcccg ttcctggcac gtcaggttgc acgcgcagcg    420
cgtaactacc tcgctggcct cctcccgcca ttcttccgtg cactcgtgga gcacacggcc    480
caaagcaatt actcttggca caccccgggt cacgtggtg gtgtcgctta ccgtaaatct    540
ccggtaggtc aagctttcca ccagttcttt ggcgagaata ccctccgctc tgacctgtct    600
gttagcgttc cagagctggg cagcctgctg atcacactg ccctctcgc ggaagcagag    660 gatcgtgccg ctcgcaattt cggtgcggac cacaccttct tgtcatcaa tggtacctct    720 actgcgaaca aaatcgtttg gcactctatg gttggtcgcg aggacctggt gctggtcgat    780
cgtacctgtc acaactctat tctgcactcc attatcatga cgggtgctat cccactgtac    840
ctgactccgg aacgcaacga actgggtatt atcggcccta ttccactctc cgagttttct    900
```

```
aaacaatcta tcgcagcaaa aattgccgcc tccccactcg cgcgtggtcg tgaaccgaaa    960
gttaaactgg ctgtcgttac caactctacc tatgacggtc tgtgttacaa cgcggaactg   1020
atcaaacaaa ccctcggcga ctctgtcgag gtactgcatt tcgacgaggc ttggtatgct   1080
tatgcggcgt ttcacgagtt ctacgacggc cgctacggta tgggcacttc tcgttccgaa   1140
gagggtccgc tggtctttgc tacccattct acccacaaga tgctcgcggc ttttccccaa   1200
gctagcatga ttcacgttca ggatggtggt acgcgcaagc tggacgtcgc ccgctttaac   1260
gaagccttta tgatgcacat cagcacctct ccacagtacg gcatcattgc gtctctcgat   1320
gtcgcaagcg ctatgatgga aggtcctgcc ggtcgtagcc tgatccaaga cgttcgat    1380 gaggcgctgt ccttccgtcg tgctctggcg aatgtccgtc agaacctgga ccgtaatgat   1440
tggtggttcg gtgtctggca accggagcag gttgagggca ccgaccaggt aggtactcac   1500
gactgggttc tcgagcctag cgcggactgg catggttttg gtgacattgc ggaggattac   1560
gttctcctcg atcctatcaa agttaccctg accaccccag gtctgagcgc tggcggtaaa   1620
ctctctgaac aaggcatccc ggcagctatc gttagccgtt cctgtggga acgtggtctg    1680 gtggtcgaga aaacgggtct gtactctttc ctggttctgt tctccatggg tatcacgaaa   1740
ggcaaatggt ctactctggt taccgagctg ctcgaattca aacgctgtta cgacgcgaat   1800
ctgccactcc tggatgtgct gccttctgta gcgcaggcgg gtggtaaacg ctataacggt   1860
gtaggtctgc gtgatctgtc cgatgccatg cacgcttctt atcgtgacaa tgccacggcg   1920
aaggccatga agcgtatgta tacggtgctc ccggaagtag ccatgcgccc gtccgaagct   1980
tatgataagc tcgtacgcgg tgaagtcgaa gctgttccta ttgcacgtct cgagggtcgt   2040
attgcggcgg ttatgctggt tccgtacccg ccaggtatcc cgctcattat gccgggtgaa   2100
cgttttactg aagctacccg ctccattctg gactatctgg agtttgcccg taccttcgag   2160
cgcgcgttcc cgggctttga ctctgatgtt cacggcctcc aacatcaaga tggcccgtct   2220
ggccgttgtt ataccgttga atgcatcaag gaataa                             2256
```

<210> SEQ ID NO 24
<211> LENGTH: 2256
<212> TYPE: DNA
<213> ORGANISM: artificial
<220> FEATURE:
<223> OTHER INFORMATION: synthetic, synthesized

<400> SEQUENCE: 24

```
atgtacaaag atctgaaatt ccctgttctg attgtacacc gcgatatcaa ggcggacacg     60
gtagccggcg agcgtgttcg cggtattgcc cacgaactcg aacaagacgg ctttagcatt    120
ctctctacgg cgtcttctgc ggaaggccgc attgtggcta gcacgcacca cggtctcgcc    180
tgcatcctcg tggcagctga gggtgcgggt gagaatcagc gtctgctcca agacgtggtt    240
gagctgatcc gtgtagctcg cgtccgtgcg ccacagctcc cgatcttcgc gctgggcgaa    300
caggtgacta ttgaaaacgc gcctgccgaa tgtatggccg acctgcacca gctccgcggc    360
attctgtatc tcttcgagga tactgtcccg ttcctggcac gtcaggttgc acgcgcagcg    420
cgtaactacc tcgctggcct cctcccgcca ttcttccgtg cactcgtgga gcacacggcc    480
caaagcaatt actcttggca caccccgggt cacggtggtg gtgtcgctta ccgtaaatct    540
ccggtaggtc aagcttttcca ccagttcttt ggcgagaata ccctccgctc tgacctgtct    600
gttagcgttc cagagctggg cagcctgctg gatcacactg gccctctcgc ggaagcagag    660
```

```
gatcgtgccg ctcgcaattt cggtgcggac cacaccttct ttgtcatcaa tggtacctct      720
actgcgaaca aaatcgtttg gcactctatg gttggtcgcg aggacctggt gctggtcgat      780
cgtacctgtc acaactctat tctgcactcc attatcatga cgggtgctat cccactgtac      840
ctgactccgg aacgcaacga actgggtatt atcggcccta ttccactctc cgagttttct      900
aaacaatcta tcgcagcaaa aattgccgcc tccccactcg cgcgtggtcg tgaaccgaaa      960
gttaaactgg ctgtcgttac caactctacc tatgacggtc tgtgttacaa cgcggaactg     1020
atcaaacaaa ccctcggcga ctctgtcgag gtactgcatt tcgacgaggc ttggtatgct     1080
tatgcggcgt ttcacgagtt ctacgacggc cgctacggta tgggcacttc tcgttccgaa     1140
gagggtccgc tggtctttgc tacccattct acccacaaga tgctcgcggc ttttttcccaa    1200 gctagcatga ttcacgttca ggatggtggt acgcgcaagc tggacgtcgc ccgctttaac     1260
gaagccttta tgatgcacat cagcacctct ccacagtacg gcatcattgc gtctctcgat     1320
gtcgcaagcg ctatgatgga aggtcctgcc ggtcgtagcc tgatccaaga cgcttcgat     1380 gaggcgctgt ccttccgtcg tgctctggcg aatgtccgtc agaacctgga ccgtaatgat     1440
tggtggttcg gtgtctggca accggagcag gttgagggca ccgaccaggt aggtactcac     1500
gactgggttc tcgagcctag cgcggactgg catggttttg gtgacattgc ggaggattac     1560
gttctcctcg atcctatcaa agttaccctg accaccccag gtctgagcgc tggcggtaaa     1620
ctctctgaac aaggcatccc ggcagctatc gttagccgtt tcctgtggga acgtggtctg     1680
gtggtcgaga aaacgggtct gtactctttc ctggttctgt tctccatggg tatcacgaaa     1740
ggcaaatggt ctactctggt taccgagctg ctcgaattca aacgctgtta cgacgcgaat     1800
ctgccactcc tggatgtgct gccttctgta gcgcaggcgg gtggtaaacg ctataacggt     1860
gtaggtctgc gtgatctgtc cgatgccatg cacgcttctt atcgtgacaa tgccacggcg     1920
aaggccatga agcgtatgta tacggtgctc ccggaagtag ccatgcgccc gtccgaagct     1980
tatgataagc tcgtacgcgg tgaagtcgaa gctgttccta ttgcacgtct cgagggtcgt     2040
attgcggcgg ttatgctggt tccgtacccg ccaggtatcc cgctcattat gccgggtgaa     2100
cgttttactg aagctacccg ctccattctg gactatctgg agtttgcccg taccttcgag     2160
cgcgcgttcc cgggctttga ctctgatgtt cacggcctcc aacatcaaga tggcccgtct     2220
ggccgttgtt ataccgttga atgcatcaag gaataa                               2256
```

<210> SEQ ID NO 25
<211> LENGTH: 44
<212> TYPE: DNA
<213> ORGANISM: Artificial Sequence
<220> FEATURE:
<223> OTHER INFORMATION: PRIMER

<400> SEQUENCE: 25
ggcgagctca cacaggaaac agaccatgcc ctacgaagcc gatg                44

<210> SEQ ID NO 26
<211> LENGTH: 28
<212> TYPE: DNA
<213> ORGANISM: Artificial Sequence
<220> FEATURE:
<223> OTHER INFORMATION: PRIMER

<400> SEQUENCE: 26
ggctctagat cagtcccagt tttccggc                                  28

<210> SEQ ID NO 27
<211> LENGTH: 50
<212> TYPE: DNA
<213> ORGANISM: Artificial Sequence
<220> FEATURE:
<223> OTHER INFORMATION: PRIMER

<400> SEQUENCE: 27
ggcgagctca cacaggaaac agaccatgta taaagacctc aaatttcccg         50

<210> SEQ ID NO 28
<211> LENGTH: 32
<212> TYPE: DNA
<213> ORGANISM: Artificial Sequence
<220> FEATURE:
<223> OTHER INFORMATION: PRIMER

<400> SEQUENCE: 28
ggctctagat cattccttta tgcattcaac gg         32

<210> SEQ ID NO 29
<211> LENGTH: 66
<212> TYPE: DNA
<213> ORGANISM: Artificial Sequence
<220> FEATURE:
<223> OTHER INFORMATION: PRIMER

<400> SEQUENCE: 29
ggcgaattca gtttattctt gacatgtagt gaggggctg gtataatgag ctcggtaccc         60
ggggat         66

<210> SEQ ID NO 30
<211> LENGTH: 34
<212> TYPE: DNA
<213> ORGANISM: Artificial Sequence
<220> FEATURE:
<223> OTHER INFORMATION: PRIMER

<400> SEQUENCE: 30
ggcagtactc aaccaagtca ttctgagaat agtg         34

<210> SEQ ID NO 31
<211> LENGTH: 49
<212> TYPE: PRT
<213> ORGANISM: Escherichia coli

<400> SEQUENCE: 31

Ile Asn Thr His Ser Thr Met Asp Val Ser Val Gln Asp Met Arg Met
1               5                   10                  15

Ala Leu Trp Phe Phe Glu Tyr Ala Leu Gly Gln Ala Glu Asp Ile Ala
            20                  25                  30

Ile Arg Met Arg Gln Tyr Thr Asp Glu Tyr Leu Asp Asn Ile Thr Pro
        35                  40                  45

Pro

<210> SEQ ID NO 32
<211> LENGTH: 49
<212> TYPE: PRT
<213> ORGANISM: Shigella sonnei

<400> SEQUENCE: 32

Ile Asn Thr His Ser Thr Met Asp Val Ser Val Gln Asp Met Arg Met
1               5                   10                  15

```
Ala Leu Trp Phe Phe Glu Tyr Ala Leu Gly Gln Ala Glu Asp Ile Ala
            20                  25                  30

Ile Arg Met Arg Gln Tyr Thr Asn Glu Tyr Leu Asp Asn Ile Thr Pro
        35                  40                  45

Pro

<210> SEQ ID NO 33
<211> LENGTH: 49
<212> TYPE: PRT
<213> ORGANISM: Salmonella enterica

<400> SEQUENCE: 33

Ile Asn Thr Asn Ser Thr Leu Asp Val Ser Val His Asp Met Arg Met
1               5                   10                  15

Ala Leu Trp Phe Phe Glu Tyr Ala Leu Gly Leu Ala Glu Asp Ile Ala
            20                  25                  30

Thr Arg Ile His Gln Tyr Thr Asn Glu Tyr Leu Asp Asn Ile Thr Pro
        35                  40                  45

Pro

<210> SEQ ID NO 34
<211> LENGTH: 49
<212> TYPE: PRT
<213> ORGANISM: Escherichia coli

<400> SEQUENCE: 34

Ala Asn Thr Tyr Ser Thr Leu Asp Val Ser Leu Asn Asp Leu Arg Leu
1               5                   10                  15

Gln Ile Ser Phe Phe Glu Tyr Ala Leu Gly Ala Ala Glu Asp Ile Ala
            20                  25                  30

Asn Lys Ile Lys Gln Thr Thr Asp Glu Tyr Ile Asn Thr Ile Leu Pro
        35                  40                  45

Pro

<210> SEQ ID NO 35
<211> LENGTH: 50
<212> TYPE: PRT
<213> ORGANISM: Pseudomonas aeruginosa

<400> SEQUENCE: 35

Gln Val Thr Ile Glu Asn Ala Pro Ala Glu Ser Met Ala Asp Leu His
1               5                   10                  15

Gln Leu Arg Gly Ile Leu Tyr Leu Phe Glu Asp Thr Val Pro Phe Leu
            20                  25                  30

Ala Arg Gln Val Ala Arg Ala Ala Arg Asn Tyr Leu Ala Gly Leu Leu
        35                  40                  45

Pro Pro
    50

<210> SEQ ID NO 36
<211> LENGTH: 50
<212> TYPE: PRT
<213> ORGANISM: Escherichia coli

<400> SEQUENCE: 36

Ala Pro Ser Gly Ser Thr Leu Leu Ile Asp Arg Asn Cys His Lys Ser
1               5                   10                  15

Leu Ala His Leu Leu Met Met Asn Asp Val Val Pro Val Trp Leu Lys
            20                  25                  30
```

-continued

```
Pro Thr Arg Asn Ala Leu Gly Ile Leu Gly Gly Ile Pro Arg Arg Glu
        35                  40                  45

Phe Thr
    50

<210> SEQ ID NO 37
<211> LENGTH: 50
<212> TYPE: PRT
<213> ORGANISM: Shigella sonnei

<400> SEQUENCE: 37

Ala Pro Ser Gly Ser Thr Leu Leu Ile Asp Arg Asn Cys His Lys Ser
1               5                   10                  15

Leu Ala His Leu Leu Met Met Asn Asp Val Val Pro Val Trp Leu Lys
            20                  25                  30

Pro Thr Arg Asn Ala Leu Gly Ile Leu Gly Gly Ile Pro Arg Arg Glu
        35                  40                  45

Phe Thr
    50

<210> SEQ ID NO 38
<211> LENGTH: 50
<212> TYPE: PRT
<213> ORGANISM: Salmonella enterica

<400> SEQUENCE: 38

Ala Pro Ala Gly Ser Thr Leu Leu Ile Asp Arg Asn Cys His Lys Ser
1               5                   10                  15

Leu Ala His Leu Leu Met Met Ser Asp Val Val Pro Leu Trp Leu Lys
            20                  25                  30

Pro Thr Arg Asn Ala Leu Gly Ile Leu Gly Gly Ile Pro Arg Arg Glu
        35                  40                  45

Phe Thr
    50

<210> SEQ ID NO 39
<211> LENGTH: 50
<212> TYPE: PRT
<213> ORGANISM: Escherichia coli

<400> SEQUENCE: 39

Ala Pro Ala Gly Ser Thr Ile Leu Ile Asp Arg Asn Cys His Lys Ser
1               5                   10                  15

Leu Thr His Leu Met Met Met Ser Asp Val Thr Pro Ile Tyr Phe Arg
            20                  25                  30

Pro Thr Arg Asn Ala Tyr Gly Ile Leu Gly Gly Ile Pro Gln Ser Glu
        35                  40                  45

Phe Gln
    50

<210> SEQ ID NO 40
<211> LENGTH: 50
<212> TYPE: PRT
<213> ORGANISM: Pseudomonas aeruginosa

<400> SEQUENCE: 40

Val Gly Arg Glu Asp Leu Val Leu Val Asp Arg Asn Cys His Lys Ser
1               5                   10                  15

Ile Leu His Ser Ile Ile Met Thr Gly Ala Ile Pro Leu Tyr Leu Thr
```

-continued

```
            20                  25                  30
Pro Glu Arg Asn Glu Leu Gly Ile Ile Gly Pro Ile Pro Leu Ser Glu
        35                  40                  45
Phe Ser
    50
```